US005621075A

United States Patent [19]
Kahn et al.

[11] Patent Number: 5,621,075
[45] Date of Patent: Apr. 15, 1997

[54] INSULIN RECEPTOR SUBSTRATE

[75] Inventors: C. Ronald Kahn, West Newton; Morris F. White, West Roxbury, both of Mass.; Paul L. Rothenberg, Narberth, Pa.

[73] Assignee: Joslin Diabetes Center, Inc., Boston, Mass.

[21] Appl. No.: 94,948

[22] Filed: Jul. 21, 1993

Related U.S. Application Data

[62] Division of Ser. No. 962,023, Oct. 15, 1992, Pat. No. 5,260,200, which is a continuation of Ser. No. 643,982, Jan. 18, 1991, abandoned.

[51] Int. Cl.$^6$ .................................................. C07K 14/47
[52] U.S. Cl. ............................... 530/350; 530/352; 514/2
[58] Field of Search ..................................... 530/350, 352; 514/2

[56] References Cited

U.S. PATENT DOCUMENTS 5,260,200  11/1993  Kahn et al. .............................. 435/68.1

OTHER PUBLICATIONS

Avruch et al., "Insulin–Stimulated Tyrosine Phosphorylation of the Insulin Receptor in Detergent Extracts of Human Placental membranes", *J. Biol. Chem.* 256:15162–15169, 1982.

Beguinot et al., "Differentiation–Dependent Phosphorylation of a 175,000 Molecular Weight Protein in Response to Insulin and Insulin–Like Growth Factor–1 in L6 Skeletal Muscle Cells", *Endocrinology*, vol. 125, No. 3, pp. 1599–1605, 1989.

Beguinot et al., "Phosphorylation of Insulin–Like Growth Factor I Receptor by Insulin Receptor Tyrosine Kinase in Intact Cultured Skeletal Muscle Cells", *Biochem.* 1988, 27, 3222–3228.

Bernier et al., "Insulin–Activated Tyrosine Phosphorylation of a 15-Kilodalton Protein in Intact 3T3–L 1 Adipocytes", *Proc. Natl. Acad. Sci. USA*, vol. 84, pp. 1844–1848, Apr. 1987.

Chou et al., "Human Insulin Receptors Mutated at the ATP–Binding Site Lack Protein Tyrosine Kinase Activity and Fail to Mediate Postreceptor Effects of Insulin", *J. Biol. Chem.*, vol. 262, No. 4, pp. 1842–1847, Feb. 5, 1987.

Condorelli et al., "Insulin and Insulin–Like Growth Factor I (IGF I) Stimulate Phosphorylation of A M $_r$ 175,000 Cytoskeleton–Associated Protein in Intact FRTL5 Cells", *J. Biol. Chem.*, vol. 264, No. 21, pp. 12633–12638, Jul. 25, 1989.

Cunningham et al., "The Complete Amino Acid Sequence of a $\beta_2$–Microglobulin", *Biochem.*, vol. 12, No. 24, Nov. 20, 1973.

Cuatrecasas, "Affinity Chromatography and Purification of the Insulin Receptor of Liver Cell Membranes", *Proc. Natl. Acad. Sci. USA*, vol. 69, No. 5, pp. 1277–1281, May 1972.

Ellis et al., "Replacement of Insulin Receptor Tyrosine Residues 1162 and 1163 Compromises Insulin–Stimulated Kinase Activity and uptake of 2–Deoxyglucose", *Cell*, vol. 45, pp. 721–732, Jun. 6, 1986.

Freychet et al., "Insulin Receptors in the Liver: Specific Binding of [$^{125}$I] Insulin to the Plasma Membrane and its Relation to Insulin Bioactivity", *Proc. Natl. Acad. Sci. USA*, vol. 68, No. 8, pp. 1833–1837, Aug. 1971.

Goren et al., "The 180,000 Molecular Weight Plasma membrane Insulin Receptor Substrate is a Protein Tyrosine Phosphatase and is Elevated in Diabetic Plasma Membranes", vol. 180, pp. 463–469.

Heffetz et al., "$H_2O_2$ Potentiates Phosphorylation of Novel Putative Substrates for the Insulin Receptor Kinase in intact Fao Cells", *J. Biol. Chem.*, vol. 264, No. 17, pp. 10126–10132, Jun. 15, 1989.

Izumi et al., "Insulin–Like Growth Factor I Rapidly Stimulates Tyrosine Phosphorylation of a $M_r$ 185,000 Protein in Intact Cells", *J. Biol. Chem.*, vol. 262, No. 3, pp. 1282–1287, Jan. 25, 1987.

Jacobs et al., "Isolation and Characterization of Genomic and cDNA Clones of Human Erythropoietin", *Nature*, vol. 313, No. 6005, pp. 806–810, Feb. 28, 1985.

Kadowaki et al., "Tyrosine Phosphorylation of Common and Specific Sets of Cellular Proteins Rapidly Induced by Insulin, Insulin–Like Growth Factor I, and Epidermal Growth Factor in an Intact Cell", *J. Biol. Chem.*, vol. 262, No. 15, pp. 7342–7350, May 25, 1987.

Kahn et al., "The Insulin Receptor and the Molecular Mechanism of Insulin Action", *J. Clin. Invest.*, vol. 82, pp. 1151–1156, Oct. 1988.

Kamps et al., "Identification of Multiple Novel Polypeptide Substrates of the v–src, v–yes, v–fps, v–ros, and v–erb B Oncogenic Tyrosine Protein Kinases Utilizing Antisera Against Phosphotyrosine", *Oncogene*, vol. 2, pp. 305–315, 1988.

Kaplan et al., "Common Elements in Growth Factor Stimulation and Oncogenic Transformation: 85 kd Phosphoprotein and Phosphatidylinositol Kinase Activity", *Cell*, vol. 50, pp. 1021–1029, Sep. 25, 1987.

Kasuga et al., "Insulin Stimulates the Phosphorylation of the 95,000–Dalton Subunit of its Own Receptor", *Science*, vol. 215, pp. 185–186; Jan. 8, 1982.

Kasuga et al., "Insulin Stimulates Tyrosine Phosphorylation of the Insulin Receptor in a Cell–Free System", *Nature*, vol. 298, pp. 667–669; Aug. 12, 1982.

Lau et al., "Phosphotyrosyl Protein Phosphatases", *Biochem. J.*, vol. 257, pp. 23–36, 1989.

Levenson et al., "Insulin–Stimulated Protein Tyrosine Phosphorylation of Intact Cells Evaluated by Faint Two–Dimensional Gel Electrophoresis", *J. Biol. Chem.*, vol. 264, No. 33, pp. 19984–19993, Nov. 25, 1989.

(List continued on next page.)

Primary Examiner—John Ulm
Attorney, Agent, or Firm—Louis Myers, Esq.; Lahive & Cockfield

[57] ABSTRACT

A purified protein that is identified herein as insulin receptor substrate 1 (IRS-1) is disclosed, as well as a method of purifying IRS-1 and a recombinant nucleic acid encoding it.

4 Claims, 17 Drawing Sheets

OTHER PUBLICATIONS

Madoff et al., "Insulin and Insulin–Like Growth Factor I Stimulate the Phosphorylation on Tyrosine of a 160 kDa Cytostolic Protein in 3T3–1 Adipocytes", *Biochem. J.*, vol. 252, pp. 7–15, 1988.

Macgawa et al., "Insulin Receptors with Defective Tyrosine Kinase Inhibit Normal Receptor Function at the Level of Substrate Phosphorylation", *J. Biol. Chem.*, vol. 263, No. 25, pp. 12629–12637, Sep. 5, 1988.

Meisenhelder et al., "Phospholipase C–γ is a Substrate for the PDGF and EGF Receptor Protein–Tyrosine Kinases in vivo and in vitro", *Cell*, vol. 57, pp. 1109–1122, Jun. 30, 1989.

Moller et al., "A Naturally occurring Mutation of Insulin Receptor Alanine 1134 Impairs Tyrosine Kinase Function and is Associated with Dominantly Inherited Insulin Resistance", *J. Biol. Chem.*, vol. 265, No. 25, pp. 14979–14985, Sep. 5, 1990.

Moller et al., "Detection of an Alteration in the Insulin–Receptor Gene in a Patient with Insulin Resistance, Acanthosis Nigricans, and the Polycystic Ovary Syndrome (Type A Insulin Resistance)", *New Engl. J. Med.*, vol. 319, pp. 1526–1529, 1988.

Moller et al., "Insulin Resistance—Mechanisms, Syndromes, and Implications", *The New England Journal of Medicine*, vol. 325, pp. 938–948, 1991.

Morgan et al., "Acute Insulin Action Requires Insulin Receptor Kinase Activity: Introduction of an Inhibitory Monoclonal Antibody into Mammalian Cells Blocks the Rapid Effects of Insulin", *PNAS*, vol. 84, pp. 41–45, 1987.

Morrison et al., "Direct Activation of the Serine/Theonine Kinase Activity of Raf–1 Through Tyrosine Phosphorylation by the PDGF β–Receptor", *Cell*, vol. 58, pp. 649–657, Aug. 25, 1989.

Odawara et al., "Human Diabetes Associated with a Mutation in the Tyrosine Kinase Domain of the Insulin Receptor", *Science*, vol. 245, pp. 66–68, Jul. 7, 1989.

Pang et al., "Purification of the Catalytically Active Phosphorylated Form of Insulin Receptor Kinase by Affinity Chromatography with O–Phosphotyrosyl–Binding Antibodies", *Arch. of Biochem. and Biophysics*, vol. 242, No. 1, pp. 176–186, Oct. 1985.

Rees–Jones et al., "An Endogenous Substrate for the Insulin Receptor–Associated Tyrosine Kinase", *J. Biol. Chem.*, vol. 260, No. 7, pp. 4461–4467, Apr. 10, 1985.

Rosen et al., "Phosphorylation Activates the Insulin Receptor Tyrosine Protein Kinase", *Proc. Natl. Adac. Sci. USA*, vol. 80, pp. 3237–3240, Jun. 1983.

Rothenberg et al., "Purification and Partial Sequence Analysis of pp 185, the Major Cellular Substrate of the Insulin Receptor Tyrosine Kinase", Purification and Partial Sequence Analysis of PP185, The Major Cellular Substrate of the Insulin Receptor Tyrosine Kinase, vol. 266, pp. 8302–8311; 1991.

Shemer et al., "Insulin and Insulin–Like Growth Factor–I Stimulate a Common Endogenous Phosphoprotein Substrate (pp 185) in Intact Neuroblastoma Cells", *J. Biol. Chem.* vol. 262, No. 32, pp. 15476–15482, Nov. 15, 1987.

Suggs et al., "Use of Synthetic Oligonucleotides as Hybridization Probes: Isolation of Cloned cDNA Sequences for Human $\beta_2$–Microglobulin", *Proc. Natl. Acad. Sci. USA*, vol. 78, No. 11, pp. 6613–6617; Nov. 1981.

Sun et al., "Structure of the Insulin Receptor Substrate IRS–1 Defines a Unique Signal Transduction Protein", *Nature*, 352:73–77, 1991.

Taira et al., "Human Diabetes Associated with a Deletion of the Tyrosine Kinase Domain of the Insulin Receptor" *Science* 245:63–66, 1989.

White et al., "Characterization of an Endogenous Substrate of the Insulin Receptor in Cultured Cells", *J. Biological Chemistry* 262:9769–9777, 1987.

White et al., "Insulin Rapidly Stimulates Tyrosine Phosphorylation of a $M_r$ 185,000 Protein in Intact Cells" *Nature* 318:183–186 1985.

White et al., "Mutation of the Insulin Receptor at Tyrosine 960 Inhibits Signal Transmission But Does Not Affect its Tyrosine Kinase Activity" *Cell* 54:641–649, 1988.

Wilden et al., "The Insulin Receptor with Phenylalanine Replacing Tyrosine–1146 Provides Evidence for Separate Signals Regulating Cellular Metabolism and Growth" *PNAS USA* 87:3358–3362, 1990.

White et al, Cells 54:641–649, 26 Aug. 1988.

Hunkapiller et al., Methods in Enzymology, 41:227–236, 1983.

```
GGAATTCCCT GGTATTTGGG CGGCTGGTGG CGGCGGGGAC TGTTGGAGGG TGGGAGGAGG      60

CAGAGGAGGA GGAGGAGAAG GAGGAGGAGG GAGAACCCCG TGCAACGTTG GGACTTGGCA     120

GCCCGCCTCC CCCTGCCCAA GGATATTTAA TTTGCCTGGG GAATCGCTAC TTCCAGAGGG     180

GAACTCGGGA GGGAAGGAGC GCGCGCCTGG AGGGCCAAGC GGGGACTCCT CCGGTCGTCT     240

CTGCCTCCCT GCATCGGACT CTACCAGGGG CGGCAAGGGA TGCACCATAG CTCCTTCTCT     300

GCTGCAAGGA CTGGGGGAGA CTTAGTCCTC GGAAGATTGC GGCTGCACTC ACCCTAGACC     360

CACTGCCTTT CCCTCTGGGC ATGAAACGCC CTTAAACTCG GATCAGGCTA TCTTCCTTTG     420

GCGCAGCTAC CTCGTCCTTC GGCTGCCCCT CCCCAGCGCC AGGAACGGCG TGAATTTCGG     480

AGTCAGGATT TCTGCTTGCT TCCTCCAGCC CGGAGTGCAT GTGCGGGGCC GCACCGAGAA     540

GCCACCCCTC ACCCAGTTTT TCGACACCTC CCTCTGCTCC GCAGCAGC ATG GCG AGC CCT 600
                                                    Met Ala Ser Pro
                                                      1
```

| | | | | | | | | | | | | | | | | |
|---|---|---|---|---|---|---|---|---|---|---|---|---|---|---|---|---|
| CCG | GAT | ACC | GAT | GGC | TTC | TCA | GAC | GTG | CGC | AAG | GTG | GGT | TAC | CTG | CGC | 648 |
| Pro | Asp | Thr | Asp | Gly | Phe | Ser | Asp | Val | Arg | Lys | Val | Gly | Tyr | Leu | Arg | |
| 5 | | | | 10 | | | | | 15 | | | | | 20 | | |
| AAA | CCC | AAG | AGT | ATG | CAT | AAG | CGC | TTT | TTC | GTG | CTG | CGG | GCG | GCC | AGC | 696 |
| Lys | Pro | Lys | Ser | Met | His | Lys | Arg | Phe | Phe | Val | Leu | Arg | Ala | Ala | Ser | |
| | | | | 25 | | | | | 30 | | | | | 35 | | |
| GAG | GCC | GGG | GGC | CCG | GCG | CGC | CTG | GAG | TAT | TAT | GAG | AAC | GAG | AAG | AAG | 744 |
| Glu | Ala | Gly | Gly | Pro | Ala | Arg | Leu | Glu | Tyr | Tyr | Glu | Asn | Glu | Lys | Lys | |
| | | | 40 | | | | | 45 | | | | | 50 | | | |
| TGG | CGG | CAC | AAG | TCG | AGC | GCC | CCC | AAA | CGC | TCG | ATC | CCC | CTC | GAG | AGC | 792 |
| Trp | Arg | His | Lys | Ser | Ser | Ala | Pro | Lys | Arg | Ser | Ile | Pro | Leu | Glu | Ser | |
| | | | 55 | | | | | 60 | | | | | 65 | | | |
| TGT | TTC | AAC | ATC | AAC | AAG | CGG | GCT | GAC | TCC | AAG | AAC | AAG | CAC | CTG | GTG | 840 |
| Cys | Phe | Asn | Ile | Asn | Lys | Arg | Ala | Asp | Ser | Lys | Asn | Lys | His | Leu | Val | |
| | | 70 | | | | | 75 | | | | | 80 | | | | |
| GCT | CTC | TAC | ACC | CGA | GAC | GAA | CAC | TTT | GCC | ATT | GCG | GCG | GAT | ACG | GAG | 888 |
| Ala | Leu | Tyr | Thr | Arg | Asp | Glu | His | Phe | Ala | Ile | Ala | Ala | Asp | Ser | Glu | |
| | 85 | | | | | 90 | | | | | 95 | | | | 100 | |

FIG. 12

```
GCT GAA CAA GAC ACG TGG TAC CAG GCT CTT CTG CAG CTG CAT AAT CGG      936
Ala Glu Gln Asp Ser Trp Tyr Gln Ala Leu Leu Gln Leu His Asn Arg
            105                 110                 115

GCA AAG GCC CAC CAT GAC GGG GCT GGA GGA GGC TGC GGT GGT AGC TGC      984
Ala Lys Ala His His Asp Gly Ala Gly Gly Gly Cys Gly Gly Ser Cys
            120                 125                 130

AGC GGC AGC TCT GGC GTC GGA GAG GCA GGG GAG GAC TTG AGC TAT GAC     1032
Ser Gly Ser Ser Gly Val Gly Glu Ala Gly Glu Asp Leu Ser Tyr Asp
            135                 140                 145

ACG GGC CCA GGA CCC GCG TTC AAG GAG GTC TGG CAG GTT ATC CTG AAA     1080
Thr Gly Pro Gly Pro Ala Phe Lys Glu Val Trp Gln Val Ile Leu Lys
            150                 155                 160

CCC AAG GGC TTA GGT CAG ACA AAG AAC TTG ATT GGT ATC TAC CGC CTC     1128
Pro Lys Gly Leu Gly Gln Thr Lys Asn Leu Ile Gly Ile Tyr Arg Leu
165                 170                 175                 180

TCG CTG ACC AGC AAG ACC ATC AGC TTT GTG AAG CTC AAC TCT GAG GCT     1176
Cys Leu Thr Ser Lys Thr Ile Ser Phe Val Lys Leu Asn Ser Glu Ala
            185                 190                 195

GCC GCT GTG GTG CTG CAG CTG ATG AAC ATC AGA CGC TGT GGC CAC TCA     1224
Ala Ala Val Val Leu Gln Leu Met Asn Ile Arg Arg Cys Gly His Ser
            200                 205                 210

CGG GCC ATG AGC CAT GAG TTT CGC CCG CGC ACG AAA AGC CAA TCT TCA     1272
Arg Ala Met Ser Asp Glu Phe Arg Pro Arg Thr Lys Ser Gln Ser Ser
            215                 220                 225

TCC AGT TGC TCC AAC CCC ATC AGT GTT CCC CTG CGC AGG CAC CAT CTC     1320
Ser Ser Cys Ser Asn Pro Ile Ser Val Pro Leu Arg Arg His His Leu
            230                 235                 240

AAC AAT CCT CCG CCC AGC CAA GTG GGG CTG ACT CGG AGA TCT CGA ACT     1368
Asn Asn Pro Pro Pro Ser Gln Val Gly Leu Thr Arg Arg Ser Arg Thr
245                 250                 255                 260

GAG AGC ATC ACT GCC ACC TCC CCT GCC AGT ATG GTG GGT GGG AAA CCA     1416
Glu Ser Ile Thr Ala Thr Ser Pro Ala Ser Met Val Gly Gly Lys Pro
            265                 270                 275

GGT TCC TTC AGG GTG CGT GCC TCC AGC GAT GGC GAA GGC ACC ATG TCC     1464
Gly Ser Phe Arg Val Arg Ala Ser Ser Asp Gly Glu Gly Thr Met Ser
            280                 285                 290

CGT CCA GCA TCA GTG GAT GGC AGT CCT GTG AGC CCT AGC ACC AAC AGG     1512
Arg Pro Ala Ser Val Asp Gly Ser Pro Val Ser Pro Ser Thr Asn Arg
            295                 300                 305
```

FIG. 12

```
ACC CAC GCC CAT CGG CAT CGA GGC AGC TCC AGG TTG CAC CCC CCA CTC          1560
Thr His Ala His Arg His Arg Gly Ser Ser Arg Leu His Pro Pro Leu
    310             315                 320

AAC CAC AGC CGC TCC ATC CCT ATG CCT TCT TCA CGA TGC TCC CCT TCA          1608
Asn His Ser Arg Ser Ile Pro Met Pro Ser Ser Arg Cys Ser Pro Ser
325             330                 335                 340

GCC ACC AGC CCA GTG AGC CTG TCA TCC AGT AGT ACC AGT GGC CAC GGC          1656
Ala Thr Ser Pro Val Ser Leu Ser Ser Ser Ser Thr Ser Gly His Gly
            345                 350                 355

TCC ACT TCA GAC TGT CTC TTC CCG AGG CGC TCT AGT GCT TCC GTG TCC          1704
Ser Thr Ser Asp Cys Leu Phe Pro Arg Arg Ser Ser Ala Ser Val Ser
        360                 365                 370

GGT TCT CCT AGC GAT GGC GGT TTC ATC TCT TCT GAT GAG TAT GGC TCT          1752
Gly Ser Pro Ser Asp Gly Gly Phe Ile Ser Ser Asp Glu Tyr Gly Ser
    375                 380                 385

AGT CCC TGC GAT TTC CGA AGT TCC TTC CGC AGT GTC ACC CCA GAT TCC          1800
Ser Pro Cys Asp Phe Arg Ser Ser Phe Arg Ser Val Thr Pro Asp Ser
390             395                 400

CTG GGC CAC ACC CCA CCA GCC AGG GGT GAG GAG GAG CTG AGC AAC TAT          1848
Leu Gly His Thr Pro Pro Ala Arg Gly Glu Glu Glu Leu Ser Asn Tyr
405             410                 415                 420

ATC TGC ATG GGT GGC AAG GGA GCC TCC ACC TTG ACA GCT CCC AAT GGT          1896
Ile Cys Met Gly Gly Lys Gly Ala Ser Thr Leu Thr Ala Pro Asn Gly
            425                 430                 435

CAC TAC ATT TTG TCT AGG GGT GGC AAC GGC CAT CGC TAC ATC CCA GGT          1944
His Tyr Ile Leu Ser Arg Gly Gly Asn Gly His Arg Tyr Ile Pro Gly
        440                 445                 450

GCT ACC ATG GGG ACA AGC CCG GCG CTG ACT GGA GAC GAA GCC GCT GGT          1992
Ala Thr Met Gly Thr Ser Pro Ala Leu Thr Gly Asp Glu Ala Ala Gly
    455                 460                 465

GCA GCA GAT CTG GAT AAC CGG TTT CGG AAG AGA ACT CAC TCG GCT GGC          2040
Ala Ala Asp Leu Asp Asn Arg Phe Arg Lys Arg Thr His Ser Ala Gly
470             475                 480

ACG TCC CCC ACC ATA TCC CAC CAG AAG ACC CCC TCG CAG TCC TCA GTG          2088
Thr Ser Pro Thr Ile Ser His Gln Lys Thr Pro Ser Gln Ser Ser Val
485             490                 495                 500

GTT TCT ATT GAG GAA TAT ACA GAG ATG ATG CCC GCT GCC TAC CCA CCA          2136
Val Ser Ile Glu Glu Tyr Thr Glu Met Met Pro Ala Ala Tyr Pro Pro
            505                 510                 515
```

FIG. 12

```
GGA GGT GGC AGT GGA GGC CGA CTG CCC GGC TAC CGG CAT TCC GCC TTC       2184
Gly Gly Gly Ser Gly Gly Arg Leu Pro Gly Tyr Arg His Ser Ala Phe
            520             525                 530

GTG CCC ACC CAC TCC TAT CCC GAG GAG GGT CTA GAG ATG CAC CAC TTG       2232
Val Pro Thr His Ser Tyr Pro Glu Glu Gly Leu Glu Met His His Leu
            535             540                 545

GAA CGT CGT GGG GGC CAC CAC CGT CCA GAC TCC TCC AAC CTC CAC ACC       2280
Glu Arg Arg Gly Gly His His Arg Pro Asp Ser Ser Asn Leu His Thr
    550                 555             560

GAT GAT GGC TAC ATG CCC ATG TCT CCC GGA GTG GCT CCA GTG CCC AGC       2328
Asp Asp Gly Tyr Met Pro Met Ser Pro Gly Val Ala Pro Val Pro Ser
565             570                 575                 580

AAC CGC AAA GGA AAT GGG GAC TAT ATG CCC ATG AGC CCC AAG AGT GTA       2376
Asn Arg Lys Gly Asn Gly Asp Tyr Met Pro Met Ser Pro Lys Ser Val
                585             590                 595

TCT GCC CCC CAG CAG ATC ATT AAC CCC ATC AGG CGC CAC CCA CAG AGA       2424
Ser Ala Pro Gln Gln Ile Ile Asn Pro Ile Arg Arg His Pro Gln Arg
            600             605                 610

GTG GAC CCC AAT GGC TAC ATG ATG ATG TCT CCC AGT GGT AGT TGC TCT       2472
Val Asp Pro Asn Gly Tyr Met Met Met Ser Pro Ser Gly Ser Cys Ser
            615             620                 625

CCT GAC ATT GGA GGT GGG TCT TGC AGC AGT AGC AGC ATC AGC GCA GCC       2520
Pro Asp Ile Gly Gly Gly Ser Cys Ser Ser Ser Ser Ile Ser Ala Ala
            630             635                 640

CCT TCT GGG AGC AGC TAT GGG AAG CCA TGG ACA AAC GGA GTA GGG GGG       2568
Pro Ser Gly Ser Ser Tyr Gly Lys Pro Trp Thr Asn Gly Val Gly Gly
645             650                 655                 660

CAC CAT ACC CAT GCC CTT CCC CAT GCC AAA CCT CCT GTT GAG AGC GGT       2616
His His Thr His Ala Leu Pro His Ala Lys Pro Pro Val Glu Ser Gly
            665             670                 675

GGT GGT AAG CTC TTG CCT TGC ACT GGT GAC TAC ATG AAC ATG TCG CCA       2664
Gly Gly Lys Leu Leu Pro Cys Thr Gly Asp Tyr Met Asn Met Ser Pro
            680             685                 690

GTG GGA GAT TCC AAC ACC AGC AGC CCC TCA GAA TGC TAC TAT GGC CCA       2712
Val Gly Asp Ser Asn Thr Ser Ser Pro Ser Glu Cys Tyr Tyr Gly Pro
            695             700                 705

GAA GAT CCC CAG CAC AAG CCT GTC CTC TCC TAC TAC TCA TTA CCA AGG       2760
Glu Asp Pro Gln His Lys Pro Val Leu Ser Tyr Tyr Ser Leu Pro Arg
            710             715                 720

TCC TTT AAG CAC ACC CAG CGC CCT GGG GAG CCA GAG GAG GGT GCC AGG       2808
```

FIG. 12

```
Ser Phe Lys His Thr Gln Arg Pro Gly Glu Pro Glu Glu Gly Ala Arg
725             730             735                 740

CAC CAG CAT CTT CGT CTC TCT TCA AGC TCT GGA CGC CTT CGC TAT ACC    2856
His Gln His Leu Arg Leu Ser Ser Ser Ser Gly Arg Leu Arg Tyr Thr
            745             750                 755

GCA ACT GCC GAA GAT TCC TCC TCT TCC ACC AGC AGC GAC AGC CTG GGT    2904
Ala Thr Ala Glu Asp Ser Ser Ser Ser Thr Ser Ser Asp Ser Leu Gly
            760             765                 770

GGG GGT TAC TGT GGG GCT AGG CCA GAG TCT AGC GTC ACA CAT CCC CAC    2952
Gly Gly Tyr Cys Gly Ala Arg Pro Glu Ser Ser Val Thr His Pro His
            775             780                 785

CAC CAT GCC TTG CAG CCC CAT CTG CCT CGA AAG GTA GAC ACA GCT GCA    3000
His His Ala Leu Gln Pro His Leu Pro Arg Lys Val Asp Thr Ala Ala
            790             795                 800

CAG ACC AAC AGC CGC CTG GCT CGA CCC ACA AGG CTG TCC TTG GGG GAT    3048
Gln Thr Asn Ser Arg Leu Ala Arg Pro Thr Arg Leu Ser Leu Gly Asp
805             810             815                 820

CCC AAG GCA AGC ACT TTA CCC CGG GTA CGA GAG CAA CAG CAG CAG CAG    3096
Pro Lys Ala Ser Thr Leu Pro Arg Val Arg Glu Gln Gln Gln Gln Gln
            825             830                 835

CAA CAG CAG CAG CAG TCT TCC CTG CAC CCT CCC GAG CCC AAA AGC CCA    3144
Gln Gln Gln Gln Gln Ser Ser Leu His Pro Pro Glu Pro Lys Ser Pro
            840             845                 850

GGA GAA TAT GTG AAT ATT GAA TTC GGG AGT GGC CAG CCA GGC TAT TTA    3192
Gly Glu Tyr Val Asn Ile Glu Phe Gly Ser Gly Gln Pro Gly Tyr Leu
            855             860                 865

GCT GGC CCT GCA ACT TCC CGT AGC TCC CCT TCA GTT CGA TGT CTA CCC    3240
Ala Gly Pro Ala Thr Ser Arg Ser Ser Pro Ser Val Arg Cys Leu Pro
    870             875                 880

CAG CTC CAC CCA GCT CCC AGA GAA GAG ACT GGC TCG GAA GAG TAC ATG    3288
Gln Leu His Pro Ala Pro Arg Glu Glu Thr Gly Ser Glu Glu Tyr Met
885             890             895                 900

AAC ATG GAC TTG GGG CCA GGC CGG AGG GCA ACC TGG CAG GAG AGT GGT    3336
Asn Met Asp Leu Gly Pro Gly Arg Arg Ala Thr Trp Gln Glu Ser Gly
            905             910                 915

GGA GTT GAG TTG GGC AGA GTA GGC CCT GCA CCT CCA GGG GCT GCT TCC    3384
Gly Val Glu Leu Gly Arg Val Gly Pro Ala Pro Pro Gly Ala Ala Ser
            920             925                 930

ATT TGT AGG CCA ACC CGG TCG GTG CCA AAT AGC CGT GGT GAT TAC ATG    3432
Ile Cys Arg Pro Thr Arg Ser Val Pro Asn Ser Arg Gly Asp Tyr Met
```

FIG. 12

|     |     |     |     |     |     |     |     |     |     |     |     |     |     |     |     |      |
|---|---|---|---|---|---|---|---|---|---|---|---|---|---|---|---|---|
| | | | 935 | | | | 940 | | | | | 945 | | | | |
| ACC | ATG | CAG | ATA | GGT | TGT | CCT | CGT | CAA | AGC | TAT | GTG | GAT | ACC | TCA | CCA | 3480 |
| Thr | Met | Gln | Ile | Gly | Cys | Pro | Arg | Gln | Ser | Tyr | Val | Asp | Thr | Ser | Pro | |
| | | | 950 | | | | 955 | | | | | 960 | | | | |
| GTG | GCC | CCA | GTC | AGC | TAT | GCT | GAC | ATG | CGG | ACA | GGC | ATT | GCT | GCA | GAG | 3528 |
| Val | Ala | Pro | Val | Ser | Tyr | Ala | Asp | Met | Arg | Thr | Gly | Ile | Ala | Ala | Glu | |
| 965 | | | | | 970 | | | | | 975 | | | | | 980 | |
| AAG | GTG | AGC | CTG | CCC | AGA | ACC | ACA | GGA | GCT | GCC | CCC | CCT | CCA | TCC | TCC | 3576 |
| Lys | Val | Ser | Leu | Pro | Arg | Thr | Thr | Gly | Ala | Ala | Pro | Pro | Pro | Ser | Ser | |
| | | | | 985 | | | | | 990 | | | | | 995 | | |
| ACA | GCC | TCT | GCT | TCT | GCT | TCT | GTT | AAA | GTG | ATT | CGT | GCA | GAC | ACT | CAA | 3624 |
| Thr | Ala | Ser | Ala | Ser | Ala | Ser | Val | Lys | Val | Ile | Arg | Ala | Asp | Thr | Gln | |
| | | | | 1000 | | | | | 1005 | | | | | 1010 | | |
| GGC | TGC | CGG | AGG | AGG | CAC | AGC | TCC | GAG | ACC | TTC | TCG | GCG | CCT | ACG | CGG | 3672 |
| Gly | Cys | Arg | Arg | Arg | His | Ser | Ser | Glu | Thr | Phe | Ser | Ala | Pro | Thr | Arg | |
| | | | 1015 | | | | | 1020 | | | | | 1025 | | | |
| GCT | GCC | AAC | ACA | GTG | TCT | TTT | GGA | GCA | GGG | GCT | GCA | GGA | GGG | GGC | AGC | 3720 |
| Ala | Ala | Asn | Thr | Val | Ser | Phe | Gly | Ala | Gly | Ala | Ala | Gly | Gly | Gly | Ser | |
| | | | 1030 | | | | | 1035 | | | | | 1040 | | | |
| GGT | GGT | GGC | AGT | GAG | GAT | GTG | AAA | CGC | CAC | AGC | TCT | GCA | TCC | TTT | GAG | 3768 |
| Gly | Gly | Gly | Ser | Glu | Asp | Val | Lys | Arg | His | Ser | Ser | Ala | Ser | Phe | Glu | |
| 1045 | | | | | 1050 | | | | | 1055 | | | | | 1060 | |
| AAT | GTG | TGG | CTG | AGA | CCC | GGG | GAT | CTA | GGG | GGA | GCA | TCC | AAG | GAG | TCG | 3816 |
| Asn | Val | Trp | Leu | Arg | Pro | Gly | Asp | Leu | Gly | Gly | Ala | Ser | Lys | Glu | Ser | |
| | | | | 1065 | | | | | 1070 | | | | | 1075 | | |
| GCT | CCA | GGG | TGC | GGG | GCT | GCC | GGG | GGA | TTG | GAG | AAG | AGT | CTT | AAC | TAT | 3864 |
| Ala | Pro | Gly | Cys | Gly | Ala | Ala | Gly | Gly | Leu | Glu | Lys | Ser | Leu | Asn | Tyr | |
| | | | | 1080 | | | | | 1085 | | | | | 1090 | | |
| ATA | GAC | TTG | GAT | TTG | GTC | AAG | GAT | GTT | AAG | CAG | CAC | CCT | CAA | GAC | TGC | 3912 |
| Ile | Asp | Leu | Asp | Leu | Val | Lys | Asp | Val | Lys | Gln | His | Pro | Gln | Asp | Cys | |
| | | | 1095 | | | | | 2000 | | | | | 2005 | | | |
| CCC | TCT | CAA | CAG | CAG | TCC | CTG | CCA | CCC | CCT | CCC | CCT | CAC | CAA | CCC | TTA | 3960 |
| Pro | Ser | Gln | Gln | Gln | Ser | Leu | Pro | Pro | Pro | Pro | Pro | His | Gln | Pro | Leu | |
| | | | 2010 | | | | | 2015 | | | | | 2020 | | | |
| GGC | AGC | AAT | GAG | GGC | AGC | TCC | CCA | AGA | CGC | TCC | AGT | GAG | GAT | TTA | AGC | 4008 |
| Gly | Ser | Asn | Glu | Gly | Ser | Ser | Pro | Arg | Arg | Ser | Ser | Glu | Asp | Leu | Ser | |
| 2025 | | | | | 2030 | | | | | 2035 | | | | | 2040 | |
| ACC | TAT | GCC | AGC | ATC | AAC | TTC | CAG | AAG | CAA | CCA | GAG | GAC | CGT | CAA | | 4053 |
| Thr | Tyr | Ala | Ser | Ile | Asn | Phe | Gln | Lys | Gln | Pro | Glu | Asp | Arg | Gln | | |
| | | | 2040 | | | | | 2045 | | | | | 2050 | | | |

FIG. 12

```
TAGCTTAACT GGACGTCACA GGCAGAATGA AAGACCTAAA TGACCTCAGC AATCCTCCTT    4113

TTTAACTCAT GGGTACCCAG ACTCGAACTC TTTCACGATT CACAACCAGG ACCTCACGTC    4173

TTCCTCCTCA GTAGATGGTA CGATGCATCC CTTACAGTTT GTTTACTTTG TACAATCCTC    4233

AGGAGTTCAT TGACTGAACT GCACGTTCTT TATTGTGCCA AGCAACAAGA AAGCACTGTG    4293

ACACCGGAAC AATGAGTGTG CATAAACTTC ATCTTGAACT TTAAGGACAG CTGGCCACGA    4353

AGAGCCAGTG TGCTCCCTGC CACGCCGAAA GAGGATGGGT TTACTCTCGT CAAATTTACA    4413

AGCATACGGT TCCTCTGCTC TGAAACCGTG TTCCATGACA CGCCGCTGTA AATTATTTCA    4473

TATGGAACTG TTCGCGTTGG GTGGAGAGAG TATTAAATAT TTAACATAGG TCTTCATTTA    4533

TATATGTAAT TTTTTAATGA AAATGTAACT TTCCTCACAG CACATTTTTT TTCTCTTGGA    4593

ATGTGGAACT GAGGTATTCA ATGTTTGTT TTAAAGAGTG GGAAGAATAC TTAAAACAAG    4653

GCTAAAAAGA GTAGACTAGG AGATGATCCT TGTTTTAAGA TTCTAATTCA GAAAAATAAT    4713

ATAATATGAA TCATAGTGCC ATAGAAGGTT CTGGACTGTA TAGTTGTACT TGCTGATGCT    4773

GTCTCTTGTA ATATAAACTT GATGTCGAGC TGAGTTCCTT TTAAGAATTA AGCTAAGTTT    4833

TGTAATTTTT TTTTTTTCCA AACCGAAGGA GGATGTATTC TACTGGGGTG TTTTCAAGTG    4893

TCGGCTTAGA ATTGGAAGTT GAATGGAAGC AAAGTTCAAC AAAGAGAGGA AGCCACAGAC    4953

TTCCATTGTA AATACTGTAG AGAGAGACAT GAGCGATCCC TTCAAGTCAA AAATCTCTCT    5013

TTGGAATGAA GAATGTGGGT GTTTATAAAT TCTGAAAATG TCTTTCTGTT CATAATAAAC    5073

TAGACACTGT TGGTCCCTCC CCACCCCCAC TTCTATAAGC CTTTCCCCCG GA            5125
```

FIG. 12

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

Tyr Met Xaa Met
               4

( 2 ) INFORMATION FOR SEQ ID NO:2:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
TCTGCTGTGA CAGGCCCCGG CGAGTTCTGG ATGCAGGTGG ATGACTCTGT GGTGGCCCAG        60

AACATG                                                                  66
```

(2) INFORMATION FOR SEQ ID NO:3:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (xi) SEQUENCE DESCRIPTION: SEQ ID NO:3:

```
TACATCCCTG GCGCCACCAT GGGCACCTCC CCTGCCCTGA CAGGCGATGA GGCC        54
```

(2) INFORMATION FOR SEQ ID NO:4:

(i) SEQUENCE CHARACTERISTICS:
    (A) LENGTH: 5125 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 589..4053

(xi) SEQUENCE DESCRIPTION: SEQ ID NO:4:

```
GGAATTCCCT GGTATTTGGG CGGCTGGTGG CGGCGGGGAC TGTTGGAGGG TGGGAGGAGG       60

CAGAGGAGGA GGAGGAGAAG GAGGAGGAGG GAGAACCCCG TGCAACGTTG GGACTTGGCA      120

GCCCGCCTCC CCTGCCCAA  GGATATTTAA TTTGCCTGGG GAATCGCTAC TTCCAGAGGG      180

GAACTCGGGA GGGAAGGAGC GCGCGCCTGG AGGGCCAAGC GGGGACTCCT CCGGTCGTCT      240

CTGCCTCCCT GCATCGGACT CTACCAGGGG CGGCAAGGGA TGCACCATAG CTCCTTCTCT      300

GCTGCAAGGA CTGGGGGAGA CTTAGTCCTC GGAAGATTGC GGCTGCACTC ACCCTAGACC      360

CACTGCCTTT CCCTCTGGGC ATGAAACGCC CTTAAACTCG GATCAGGCTA TCTTCCTTTG      420

GCGCAGCTAC CTCGTCCTTC GGCTGCCCCT CCCCAGCGCC AGGAACGGCG TGAATTTCGG      480

AGTCAGGATT TCTGCTTGCT TCCTCCAGCC CGGAGTGCAT GTGCGGGGCC GCACCGAGAA      540

GCCACCCCTC ACCCAGTTTT TCGACACCTC CCTCTGCTCC GCAGCAGC ATG GCG AGC      597
                                                   Met Ala Ser
                                                    1
```

```
CCT CCG GAT ACC GAT GGC TTC TCA GAC GTG CGC AAG GTG GGT TAC CTG      645
Pro Pro Asp Thr Asp Gly Phe Ser Asp Val Arg Lys Val Gly Tyr Leu
     5              10                  15

CGC AAA CCC AAG AGT ATG CAT AAG CGC TTT TTC GTG CTG CGG GCG GCC      693
Arg Lys Pro Lys Ser Met His Lys Arg Phe Phe Val Leu Arg Ala Ala
 20              25                  30                  35

AGC GAG GCC GGG GGC CCG GCG CGC CTG GAG TAT TAT GAG AAC GAG AAG      741
Ser Glu Ala Gly Gly Pro Ala Arg Leu Glu Tyr Tyr Glu Asn Glu Lys
         40                  45                  50

AAG TGG CGG CAC AAG TCG AGC GCC CCC AAA CGC TCG ATC CCC CTC GAG      789
Lys Trp Arg His Lys Ser Ser Ala Pro Lys Arg Ser Ile Pro Leu Glu
             55                  60                  65

AGC TGT TTC AAC ATC AAC AAG CGG GCT GAC TCC AAG AAC AAG CAC CTG      837
Ser Cys Phe Asn Ile Asn Lys Arg Ala Asp Ser Lys Asn Lys His Leu
         70                  75                  80

GTG GCT CTC TAC ACC CGA GAC GAA CAC TTT GCC ATT GCG GCG GAT ACG      885
Val Ala Leu Tyr Thr Arg Asp Glu His Phe Ala Ile Ala Ala Asp Thr
     85                  90                  95

GAG GCT GAA CAA GAC ACG TGG TAC CAG GCT CTT CTG CAG CTG CAT AAT      933
Glu Ala Glu Gln Asp Thr Trp Tyr Gln Ala Leu Leu Gln Leu His Asn
100                 105                 110                 115

CGG GCA AAG GCC CAC CAT GAC GGG GCT GGA GGA GGC TGC GGT GGT AGC      981
```

|     |     |     |     |     |     |     |     |     |     |     |     |     |     |     |     |
| --- | --- | --- | --- | --- | --- | --- | --- | --- | --- | --- | --- | --- | --- | --- | --- |
| Arg | Ala | Lys | Ala | His | His | Asp | Gly | Ala | Gly | Gly | Gly | Cys | Gly | Gly | Ser |
|     |     |     |     | 120 |     |     |     |     | 125 |     |     |     |     | 130 |     |

| TGC | AGC | GGC | AGC | TCT | GGC | GTC | GGA | GAG | GCA | GGG | GAG | GAC | TTG | AGC | TAT | 1029 |
|-----|-----|-----|-----|-----|-----|-----|-----|-----|-----|-----|-----|-----|-----|-----|-----|------|
| Cys | Ser | Gly | Ser | Ser | Gly | Val | Gly | Glu | Ala | Gly | Glu | Asp | Leu | Ser | Tyr |      |
|     |     |     | 135 |     |     |     |     | 140 |     |     |     |     | 145 |     |     |      |

| GAC | ACG | GGC | CCA | GGA | CCC | GCG | TTC | AAG | GAG | GTC | TGG | CAG | GTT | ATC | CTG | 1077 |
| Asp | Thr | Gly | Pro | Gly | Pro | Ala | Phe | Lys | Glu | Val | Trp | Gln | Val | Ile | Leu |      |
|     |     | 150 |     |     |     |     | 155 |     |     |     |     | 160 |     |     |     |      |

| AAA | CCC | AAG | GGC | TTA | GGT | CAG | ACA | AAG | AAC | TTG | ATT | GGT | ATC | TAC | CGC | 1125 |
| Lys | Pro | Lys | Gly | Leu | Gly | Gln | Thr | Lys | Asn | Leu | Ile | Gly | Ile | Tyr | Arg |      |
|     | 165 |     |     |     |     | 170 |     |     |     |     | 175 |     |     |     |     |      |

| CTC | TCG | CTG | ACC | AGC | AAG | ACC | ATC | AGC | TTT | GTG | AAG | CTC | AAC | TCT | GAG | 1173 |
| Leu | Ser | Leu | Thr | Ser | Lys | Thr | Ile | Ser | Phe | Val | Lys | Leu | Asn | Ser | Glu |      |
| 180 |     |     |     |     | 185 |     |     |     |     | 190 |     |     |     |     | 195 |      |

| GCT | GCC | GCT | GTG | GTG | CTG | CAG | CTG | ATG | AAC | ATC | AGA | CGC | TGT | GGC | CAC | 1221 |
| Ala | Ala | Ala | Val | Val | Leu | Gln | Leu | Met | Asn | Ile | Arg | Arg | Cys | Gly | His |      |
|     |     |     |     | 200 |     |     |     |     | 205 |     |     |     |     | 210 |     |      |

| TCA | CGG | GCC | ATG | AGC | CAT | GAG | TTT | CGC | CCG | CGC | ACG | AAA | AGC | CAA | TCT | 1269 |
| Ser | Arg | Ala | Met | Ser | His | Glu | Phe | Arg | Pro | Arg | Thr | Lys | Ser | Gln | Ser |      |
|     |     |     | 215 |     |     |     |     | 220 |     |     |     |     | 225 |     |     |      |

| TCA | TCC | AGT | TGC | TCC | AAC | CCC | ATC | AGT | GTT | CCC | CTG | CGC | AGG | CAC | CAT | 1317 |
| Ser | Ser | Ser | Cys | Ser | Asn | Pro | Ile | Ser | Val | Pro | Leu | Arg | Arg | His | His |      |
|     |     | 230 |     |     |     |     | 235 |     |     |     |     | 240 |     |     |     |      |

| CTC | AAC | AAT | CCT | CCG | CCC | AGC | CAA | GTG | GGG | CTG | ACT | CGG | AGA | TCT | CGA | 1365 |
| Leu | Asn | Asn | Pro | Pro | Pro | Ser | Gln | Val | Gly | Leu | Thr | Arg | Arg | Ser | Arg |      |
| 245 |     |     |     |     | 250 |     |     |     |     | 255 |     |     |     |     |     |      |

| ACT | GAG | AGC | ATC | ACT | GCC | ACC | TCC | CCT | GCC | AGT | ATG | GTG | GGT | GGG | AAA | 1413 |
| Thr | Glu | Ser | Ile | Thr | Ala | Thr | Ser | Pro | Ala | Ser | Met | Val | Gly | Gly | Lys |      |
| 260 |     |     |     |     | 265 |     |     |     |     | 270 |     |     |     |     | 275 |      |

| CCA | GGT | TCC | TTC | AGG | GTG | CGT | GCC | TCC | AGC | GAT | GGC | GAA | GGC | ACC | ATG | 1461 |
| Pro | Gly | Ser | Phe | Arg | Val | Arg | Ala | Ser | Ser | Asp | Gly | Glu | Gly | Thr | Met |      |
|     |     |     |     | 280 |     |     |     |     | 285 |     |     |     |     | 290 |     |      |

| TCC | CGT | CCA | GCA | TCA | GTG | GAT | GGC | AGT | CCT | GTG | AGC | CCT | AGC | ACC | AAC | 1509 |
| Ser | Arg | Pro | Ala | Ser | Val | Asp | Gly | Ser | Pro | Val | Ser | Pro | Ser | Thr | Asn |      |
|     |     |     | 295 |     |     |     |     | 300 |     |     |     |     | 305 |     |     |      |

| AGG | ACC | CAC | GCC | CAT | CGG | CAT | CGA | GGC | AGC | TCC | AGG | TTG | CAC | CCC | CCA | 1557 |
| Arg | Thr | His | Ala | His | Arg | His | Arg | Gly | Ser | Ser | Arg | Leu | His | Pro | Pro |      |
|     |     | 310 |     |     |     |     | 315 |     |     |     |     | 320 |     |     |     |      |

| CTC | AAC | CAC | AGC | CGC | TCC | ATC | CCT | ATG | CCT | TCT | TCA | CGA | TGC | TCC | CCT | 1605 |
| Leu | Asn | His | Ser | Arg | Ser | Ile | Pro | Met | Pro | Ser | Ser | Arg | Cys | Ser | Pro |      |
| 325 |     |     |     |     | 330 |     |     |     |     | 335 |     |     |     |     |     |      |

| TCA | GCC | ACC | AGC | CCA | GTG | AGC | CTG | TCA | TCC | AGT | AGT | ACC | AGT | GGC | CAC | 1653 |
| Ser | Ala | Thr | Ser | Pro | Val | Ser | Leu | Ser | Ser | Ser | Ser | Thr | Ser | Gly | His |      |
| 340 |     |     |     |     | 345 |     |     |     |     | 350 |     |     |     |     | 355 |      |

| GGC | TCC | ACT | TCA | GAC | TGT | CTC | TTC | CCG | AGG | CGC | TCT | AGT | GCT | TCC | GTG | 1701 |
| Gly | Ser | Thr | Ser | Asp | Cys | Leu | Phe | Pro | Arg | Arg | Ser | Ser | Ala | Ser | Val |      |
|     |     |     |     | 360 |     |     |     |     | 365 |     |     |     |     | 370 |     |      |

| TCC | GGT | TCT | CCT | AGC | GAT | GGC | GGT | TTC | ATC | TCT | TCT | GAT | GAG | TAT | GGC | 1749 |
| Ser | Gly | Ser | Pro | Ser | Asp | Gly | Gly | Phe | Ile | Ser | Ser | Asp | Glu | Tyr | Gly |      |
|     |     |     | 375 |     |     |     |     | 380 |     |     |     |     | 385 |     |     |      |

| TCT | AGT | CCC | TGC | GAT | TTC | CGA | AGT | TCC | TTC | CGC | AGT | GTC | ACC | CCA | GAT | 1797 |
| Ser | Ser | Pro | Cys | Asp | Phe | Arg | Ser | Ser | Phe | Arg | Ser | Val | Thr | Pro | Asp |      |
|     |     | 390 |     |     |     |     | 395 |     |     |     |     | 400 |     |     |     |      |

| TCC | CTG | GGC | CAC | ACC | CCA | CCA | GCC | AGG | GGT | GAG | GAG | GAG | CTG | AGC | AAC | 1845 |
| Ser | Leu | Gly | His | Thr | Pro | Pro | Ala | Arg | Gly | Glu | Glu | Glu | Leu | Ser | Asn |      |
|     | 405 |     |     |     |     | 410 |     |     |     |     | 415 |     |     |     |     |      |

| TAT | ATC | TGC | ATG | GGT | GGC | AAG | GGA | GCC | TCC | ACC | TTG | ACA | GCT | CCC | AAT | 1893 |
| Tyr | Ile | Cys | Met | Gly | Gly | Lys | Gly | Ala | Ser | Thr | Leu | Thr | Ala | Pro | Asn |      |
| 420 |     |     |     |     | 425 |     |     |     |     | 430 |     |     |     |     | 435 |      |

| GGT | CAC | TAC | ATT | TTG | TCT | AGG | GGT | GGC | AAC | GGC | CAT | CGC | TAC | ATC | CCA | 1941 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Gly | His | Tyr | Ile | Leu | Ser | Arg | Gly | Gly | Asn | Gly | His | Arg | Tyr | Ile | Pro |      |
|     |     |     |     | 440 |     |     |     | 445 |     |     |     |     |     | 450 |     |      |
| GGT | GCT | ACC | ATG | GGG | ACA | AGC | CCG | GCG | CTG | ACT | GGA | GAC | GAA | GCC | GCT | 1989 |
| Gly | Ala | Thr | Met | Gly | Thr | Ser | Pro | Ala | Leu | Thr | Gly | Asp | Glu | Ala | Ala |      |
|     |     |     | 455 |     |     |     |     | 460 |     |     |     |     | 465 |     |     |      |
| GGT | GCA | GCA | GAT | CTG | GAT | AAC | CGG | TTT | CGG | AAG | AGA | ACT | CAC | TCG | GCT | 2037 |
| Gly | Ala | Ala | Asp | Leu | Asp | Asn | Arg | Phe | Arg | Lys | Arg | Thr | His | Ser | Ala |      |
|     |     | 470 |     |     |     |     | 475 |     |     |     |     | 480 |     |     |     |      |
| GGC | ACG | TCC | CCC | ACC | ATA | TCC | CAC | CAG | AAG | ACC | CCC | TCG | CAG | TCC | TCA | 2085 |
| Gly | Thr | Ser | Pro | Thr | Ile | Ser | His | Gln | Lys | Thr | Pro | Ser | Gln | Ser | Ser |      |
|     | 485 |     |     |     |     | 490 |     |     |     |     | 495 |     |     |     |     |      |
| GTG | GTT | TCT | ATT | GAG | GAA | TAT | ACA | GAG | ATG | ATG | CCC | GCT | GCC | TAC | CCA | 2133 |
| Val | Val | Ser | Ile | Glu | Glu | Tyr | Thr | Glu | Met | Met | Pro | Ala | Ala | Tyr | Pro |      |
| 500 |     |     |     |     | 505 |     |     |     | 510 |     |     |     |     |     | 515 |      |
| CCA | GGA | GGT | GGC | AGT | GGA | GGC | CGA | CTG | CCC | GGC | TAC | CGG | CAT | TCC | GCC | 2181 |
| Pro | Gly | Gly | Gly | Ser | Gly | Gly | Arg | Leu | Pro | Gly | Tyr | Arg | His | Ser | Ala |      |
|     |     |     |     | 520 |     |     |     |     | 525 |     |     |     |     | 530 |     |      |
| TTC | GTG | CCC | ACC | CAC | TCC | TAT | CCC | GAG | GAG | GGT | CTA | GAG | ATG | CAC | CAC | 2229 |
| Phe | Val | Pro | Thr | His | Ser | Tyr | Pro | Glu | Glu | Gly | Leu | Glu | Met | His | His |      |
|     |     |     | 535 |     |     |     |     | 540 |     |     |     |     | 545 |     |     |      |
| TTG | GAA | CGT | CGT | GGG | GGC | CAC | CAC | CGT | CCA | GAC | TCC | TCC | AAC | CTC | CAC | 2277 |
| Leu | Glu | Arg | Arg | Gly | Gly | His | His | Arg | Pro | Asp | Ser | Ser | Asn | Leu | His |      |
|     || 550 |     |     |     |     | 555 |     |     |     |     | 560 |     |     |     |      |
| ACC | GAT | GAT | GGC | TAC | ATG | CCC | ATG | TCT | CCC | GGA | GTG | GCT | CCA | GTG | CCC | 2325 |
| Thr | Asp | Asp | Gly | Tyr | Met | Pro | Met | Ser | Pro | Gly | Val | Ala | Pro | Val | Pro |      |
|     | 565 |     |     |     |     | 570 |     |     |     |     | 575 |     |     |     |     |      |
| AGC | AAC | CGC | AAA | GGA | AAT | GGG | GAC | TAT | ATG | CCC | ATG | AGC | CCC | AAG | AGT | 2373 |
| Ser | Asn | Arg | Lys | Gly | Asn | Gly | Asp | Tyr | Met | Pro | Met | Ser | Pro | Lys | Ser |      |
| 580 |     |     |     |     | 585 |     |     |     |     | 590 |     |     |     |     | 595 |      |
| GTA | TCT | GCC | CCC | CAG | CAG | ATC | ATT | AAC | CCC | ATC | AGG | CGC | CAC | CCA | CAG | 2421 |
| Val | Ser | Ala | Pro | Gln | Gln | Ile | Ile | Asn | Pro | Ile | Arg | Arg | His | Pro | Gln |      |
|     |     |     |     | 600 |     |     |     |     | 605 |     |     |     |     | 610 |     |      |
| AGA | GTG | GAC | CCC | AAT | GGC | TAC | ATG | ATG | ATG | TCT | CCC | AGT | GGT | AGT | TGC | 2469 |
| Arg | Val | Asp | Pro | Asn | Gly | Tyr | Met | Met | Met | Ser | Pro | Ser | Gly | Ser | Cys |      |
|     |     |     | 615 |     |     |     |     | 620 |     |     |     |     | 625 |     |     |      |
| TCT | CCT | GAC | ATT | GGA | GGT | GGG | TCT | TGC | AGC | AGT | AGC | AGC | ATC | AGC | GCA | 2517 |
| Ser | Pro | Asp | Ile | Gly | Gly | Gly | Ser | Cys | Ser | Ser | Ser | Ser | Ile | Ser | Ala |      |
|     |     | 630 |     |     |     |     | 635 |     |     |     |     | 640 |     |     |     |      |
| GCC | CCT | TCT | GGG | AGC | AGC | TAT | GGG | AAG | CCA | TGG | ACA | AAC | GGA | GTA | GGG | 2565 |
| Ala | Pro | Ser | Gly | Ser | Ser | Tyr | Gly | Lys | Pro | Trp | Thr | Asn | Gly | Val | Gly |      |
|     | 645 |     |     |     |     | 650 |     |     |     |     | 655 |     |     |     |     |      |
| GGG | CAC | CAT | ACC | CAT | GCC | CTT | CCC | CAT | GCC | AAA | CCT | CCT | GTT | GAG | AGC | 2613 |
| Gly | His | His | Thr | His | Ala | Leu | Pro | His | Ala | Lys | Pro | Pro | Val | Glu | Ser |      |
| 660 |     |     |     |     | 665 |     |     |     |     | 670 |     |     |     |     | 675 |      |
| GGT | GGT | GGT | AAG | CTC | TTG | CCT | TGC | ACT | GGT | GAC | TAC | ATG | AAC | ATG | TCG | 2661 |
| Gly | Gly | Gly | Lys | Leu | Leu | Pro | Cys | Thr | Gly | Asp | Tyr | Met | Asn | Met | Ser |      |
|     |     |     |     | 680 |     |     |     |     | 685 |     |     |     |     | 690 |     |      |
| CCA | GTG | GGA | GAT | TCC | AAC | ACC | AGC | AGC | CCC | TCA | GAA | TGC | TAC | TAT | GGC | 2709 |
| Pro | Val | Gly | Asp | Ser | Asn | Thr | Ser | Ser | Pro | Ser | Glu | Cys | Tyr | Tyr | Gly |      |
|     |     |     | 695 |     |     |     |     | 700 |     |     |     |     | 705 |     |     |      |
| CCA | GAA | GAT | CCC | CAG | CAC | AAG | CCT | GTC | CTC | TCC | TAC | TAC | TCA | TTA | CCA | 2757 |
| Pro | Glu | Asp | Pro | Gln | His | Lys | Pro | Val | Leu | Ser | Tyr | Tyr | Ser | Leu | Pro |      |
|     |     | 710 |     |     |     |     | 715 |     |     |     |     | 720 |     |     |     |      |
| AGG | TCC | TTT | AAG | CAC | ACC | CAG | CGC | CCT | GGG | GAG | CCA | GAG | GAG | GGT | GCC | 2805 |
| Arg | Ser | Phe | Lys | His | Thr | Gln | Arg | Pro | Gly | Glu | Pro | Glu | Glu | Gly | Ala |      |
|     | 725 |     |     |     |     | 730 |     |     |     |     | 735 |     |     |     |     |      |
| AGG | CAC | CAG | CAT | CTT | CGT | CTC | TCT | TCA | AGC | TCT | GGA | CGC | CTT | CGC | TAT | 2853 |
| Arg | His | Gln | His | Leu | Arg | Leu | Ser | Ser | Ser | Ser | Gly | Arg | Leu | Arg | Tyr |      |
| 740 |     |     |     |     | 745 |     |     |     |     | 750 |     |     |     |     | 755 |      |
| ACC | GCA | ACT | GCC | GAA | GAT | TCC | TCC | TCT | TCC | ACC | AGC | AGC | GAC | AGC | CTG | 2901 |

|  |  |  |  |  |  |  |  |  |  |  |  |  |  |  |  |
|---|---|---|---|---|---|---|---|---|---|---|---|---|---|---|---|
| Thr | Ala | Thr | Ala | Glu | Asp | Ser | Ser | Ser | Ser | Thr | Ser | Ser | Asp | Ser | Leu |
|  |  |  |  | 760 |  |  |  | 765 |  |  |  |  | 770 |  |  |

| GGT | GGG | GGT | TAC | TGT | GGG | GCT | AGG | CCA | GAG | TCT | AGC | GTC | ACA | CAT | CCC | 2949 |
|---|---|---|---|---|---|---|---|---|---|---|---|---|---|---|---|---|
| Gly | Gly | Gly | Tyr | Cys | Gly | Ala | Arg | Pro | Glu | Ser | Ser | Val | Thr | His | Pro |  |
|  |  |  | 775 |  |  |  | 780 |  |  |  |  |  | 785 |  |  |  |

| CAC | CAC | CAT | GCC | TTG | CAG | CCC | CAT | CTG | CCT | CGA | AAG | GTA | GAC | ACA | GCT | 2997 |
|---|---|---|---|---|---|---|---|---|---|---|---|---|---|---|---|---|
| His | His | His | Ala | Leu | Gln | Pro | His | Leu | Pro | Arg | Lys | Val | Asp | Thr | Ala |  |
|  |  | 790 |  |  |  |  | 795 |  |  |  |  | 800 |  |  |  |  |

| GCA | CAG | ACC | AAC | AGC | CGC | CTG | GCT | CGA | CCC | ACA | AGG | CTG | TCC | TTG | GGG | 3045 |
|---|---|---|---|---|---|---|---|---|---|---|---|---|---|---|---|---|
| Ala | Gln | Thr | Asn | Ser | Arg | Leu | Ala | Arg | Pro | Thr | Arg | Leu | Ser | Leu | Gly |  |
|  | 805 |  |  |  |  | 810 |  |  |  |  | 815 |  |  |  |  |  |

| GAT | CCC | AAG | GCA | AGC | ACT | TTA | CCC | CGG | GTA | CGA | GAG | CAG | CAG | CAG | CAG | 3093 |
|---|---|---|---|---|---|---|---|---|---|---|---|---|---|---|---|---|
| Asp | Pro | Lys | Ala | Ser | Thr | Leu | Pro | Arg | Val | Arg | Glu | Gln | Gln | Gln | Gln |  |
| 820 |  |  |  |  | 825 |  |  |  |  | 830 |  |  |  |  | 835 |  |

| CAG | CAA | CAG | CAG | CAG | CAG | TCT | TCC | CTG | CAC | CCT | CCC | GAG | CCC | AAA | AGC | 3141 |
|---|---|---|---|---|---|---|---|---|---|---|---|---|---|---|---|---|
| Gln | Gln | Gln | Gln | Gln | Gln | Ser | Ser | Leu | His | Pro | Pro | Glu | Pro | Lys | Ser |  |
|  |  |  |  | 840 |  |  |  |  | 845 |  |  |  |  | 850 |  |  |

| CCA | GGA | GAA | TAT | GTG | AAT | ATT | GAA | TTC | GGG | AGT | GGC | CAG | CCA | GGC | TAT | 3189 |
|---|---|---|---|---|---|---|---|---|---|---|---|---|---|---|---|---|
| Pro | Gly | Glu | Tyr | Val | Asn | Ile | Glu | Phe | Gly | Ser | Gly | Gln | Pro | Gly | Tyr |  |
|  |  |  | 855 |  |  |  |  | 860 |  |  |  |  | 865 |  |  |  |

| TTA | GCT | GGC | CCT | GCA | ACT | TCC | CGT | AGC | TCC | CCT | TCA | GTT | CGA | TGT | CTA | 3237 |
|---|---|---|---|---|---|---|---|---|---|---|---|---|---|---|---|---|
| Leu | Ala | Gly | Pro | Ala | Thr | Ser | Arg | Ser | Ser | Pro | Ser | Val | Arg | Cys | Leu |  |
|  |  | 870 |  |  |  |  | 875 |  |  |  |  | 880 |  |  |  |  |

| CCC | CAG | CTC | CAC | CCA | GCT | CCC | AGA | GAA | GAG | ACT | GGC | TCG | GAA | GAG | TAC | 3285 |
|---|---|---|---|---|---|---|---|---|---|---|---|---|---|---|---|---|
| Pro | Gln | Leu | His | Pro | Ala | Pro | Arg | Glu | Glu | Thr | Gly | Ser | Glu | Glu | Tyr |  |
|  | 885 |  |  |  |  | 890 |  |  |  |  | 895 |  |  |  |  |  |

| ATG | AAC | ATG | GAC | TTG | GGG | CCA | GGC | CGG | AGG | GCA | ACC | TGG | CAG | GAG | AGT | 3333 |
|---|---|---|---|---|---|---|---|---|---|---|---|---|---|---|---|---|
| Met | Asn | Met | Asp | Leu | Gly | Pro | Gly | Arg | Arg | Ala | Thr | Trp | Gln | Glu | Ser |  |
| 900 |  |  |  |  | 905 |  |  |  |  | 910 |  |  |  |  | 915 |  |

| GGT | GGA | GTT | GAG | TTG | GGC | AGA | GTA | GGC | CCT | GCA | CCT | CCA | GGG | GCT | GCT | 3381 |
|---|---|---|---|---|---|---|---|---|---|---|---|---|---|---|---|---|
| Gly | Gly | Val | Glu | Leu | Gly | Arg | Val | Gly | Pro | Ala | Pro | Pro | Gly | Ala | Ala |  |
|  |  |  |  | 920 |  |  |  |  | 925 |  |  |  |  | 930 |  |  |

| TCC | ATT | TGT | AGG | CCA | ACC | CGG | TCG | GTG | CCA | AAT | AGC | CGT | GGT | GAT | TAC | 3429 |
|---|---|---|---|---|---|---|---|---|---|---|---|---|---|---|---|---|
| Ser | Ile | Cys | Arg | Pro | Thr | Arg | Ser | Val | Pro | Asn | Ser | Arg | Gly | Asp | Tyr |  |
|  |  |  | 935 |  |  |  |  | 940 |  |  |  |  | 945 |  |  |  |

| ATG | ACC | ATG | CAG | ATA | GGT | TGT | CCT | CGT | CAA | AGC | TAT | GTG | GAT | ACC | TCA | 3477 |
|---|---|---|---|---|---|---|---|---|---|---|---|---|---|---|---|---|
| Met | Thr | Met | Gln | Ile | Gly | Cys | Pro | Arg | Gln | Ser | Tyr | Val | Asp | Thr | Ser |  |
|  |  |  | 950 |  |  |  |  | 955 |  |  |  |  | 960 |  |  |  |

| CCA | GTG | GCC | CCA | GTC | AGC | TAT | GCT | GAC | ATG | CGG | ACA | GGC | ATT | GCT | GCA | 3525 |
|---|---|---|---|---|---|---|---|---|---|---|---|---|---|---|---|---|
| Pro | Val | Ala | Pro | Val | Ser | Tyr | Ala | Asp | Met | Arg | Thr | Gly | Ile | Ala | Ala |  |
|  | 965 |  |  |  |  | 970 |  |  |  |  | 975 |  |  |  |  |  |

| GAG | AAG | GTG | AGC | CTG | CCC | AGA | ACC | ACA | GGA | GCT | GCC | CCC | CCT | CCA | TCC | 3573 |
|---|---|---|---|---|---|---|---|---|---|---|---|---|---|---|---|---|
| Glu | Lys | Val | Ser | Leu | Pro | Arg | Thr | Thr | Gly | Ala | Ala | Pro | Pro | Pro | Ser |  |
| 980 |  |  |  |  | 985 |  |  |  |  | 990 |  |  |  |  | 995 |  |

| TCC | ACA | GCC | TCT | GCT | TCT | GCT | TCT | GTT | AAA | GTG | ATT | CGT | GCA | GAC | ACT | 3621 |
|---|---|---|---|---|---|---|---|---|---|---|---|---|---|---|---|---|
| Ser | Thr | Ala | Ser | Ala | Ser | Ala | Ser | Val | Lys | Val | Ile | Arg | Ala | Asp | Thr |  |
|  |  |  |  | 1000 |  |  |  |  | 1005 |  |  |  |  | 1010 |  |  |

| CAA | GGC | TGC | CGG | AGG | AGG | CAC | AGC | TCC | GAG | ACC | TTC | TCG | GCG | CCT | ACG | 3669 |
|---|---|---|---|---|---|---|---|---|---|---|---|---|---|---|---|---|
| Gln | Gly | Cys | Arg | Arg | Arg | His | Ser | Ser | Glu | Thr | Phe | Ser | Ala | Pro | Thr |  |
|  |  |  | 1015 |  |  |  |  | 1020 |  |  |  |  | 1025 |  |  |  |

| CGG | GCT | GCC | AAC | ACA | GTG | TCT | TTT | GGA | GCA | GGG | GCT | GCA | GGA | GGG | GGC | 3717 |
|---|---|---|---|---|---|---|---|---|---|---|---|---|---|---|---|---|
| Arg | Ala | Ala | Asn | Thr | Val | Ser | Phe | Gly | Ala | Gly | Ala | Ala | Gly | Gly | Gly |  |
|  |  |  | 1030 |  |  |  |  | 1035 |  |  |  |  | 1040 |  |  |  |

| AGC | GGT | GGT | GGC | AGT | GAG | GAT | GTG | AAA | CGC | CAC | AGC | TCT | GCA | TCC | TTT | 3765 |
|---|---|---|---|---|---|---|---|---|---|---|---|---|---|---|---|---|
| Ser | Gly | Gly | Gly | Ser | Glu | Asp | Val | Lys | Arg | His | Ser | Ser | Ala | Ser | Phe |  |
|  | 1045 |  |  |  |  | 1050 |  |  |  |  | 1055 |  |  |  |  |  |

| GAG | AAT | GTG | TGG | CTG | AGA | CCC | GGG | GAT | CTA | GGG | GGA | GCA | TCC | AAG | GAG | 3813 |
|---|---|---|---|---|---|---|---|---|---|---|---|---|---|---|---|---|
| Glu | Asn | Val | Trp | Leu | Arg | Pro | Gly | Asp | Leu | Gly | Gly | Ala | Ser | Lys | Glu |  |
| 1060 |  |  |  |  | 1065 |  |  |  |  | 1070 |  |  |  |  | 1075 |  |

| TCG | GCT | CCA | GGG | TGC | GGG | GCT | GCC | GGG | GGA | TTG | GAG | AAG | AGT | CTT | AAC | 3861 |
|---|---|---|---|---|---|---|---|---|---|---|---|---|---|---|---|---|

| | | | | | | | | | | | | |
|---|---|---|---|---|---|---|---|---|---|---|---|---|
| Ser | Ala | Pro | Gly | Cys | Gly | Ala | Ala | Gly | Gly | Leu | Glu | Lys | Ser | Leu | Asn |
| | | | 1080 | | | | | 1085 | | | | 1090 |

```
TAT ATA GAC TTG GAT TTG GTC AAG GAT GTT AAG CAG CAC CCT CAA GAC      3909
Tyr Ile Asp Leu Asp Leu Val Lys Asp Val Lys Gln His Pro Gln Asp
            1095                1100            1105

TGC CCC TCT CAA CAG CAG TCC CTG CCA CCC CCT CCC CCT CAC CAA CCC      3957
Cys Pro Ser Gln Gln Gln Ser Leu Pro Pro Pro Pro Pro His Gln Pro
        1110                1115                1120

TTA GGC AGC AAT GAG GGC AGC TCC CCA AGA CGC TCC AGT GAG GAT TTA      4005
Leu Gly Ser Asn Glu Gly Ser Ser Pro Arg Arg Ser Ser Glu Asp Leu
        1125                1130                1135

AGC ACC TAT GCC AGC ATC AAC TTC CAG AAG CAA CCA GAG GAC CGT CAA      4053
Ser Thr Tyr Ala Ser Ile Asn Phe Gln Lys Gln Pro Glu Asp Arg Gln
1140                1145                1150                1155

TAGCTTAACT GGACGTCACA GGCAGAATGA AAGACCTAAA TGACCTCAGC AATCCTCCTT    4113
TTTAACTCAT GGGTACCCAG ACTCGAACTC TTTCACGATT CACAACCAGG ACCTCACGTC    4173
TTCCTCCTCA GTAGATGGTA CGATGCATCC CTTACAGTTT GTTTACTTTG TACAATCCTC    4233
AGGAGTTCAT TGACTGAACT GCACGTTCTT TATTGTGCCA AGCAACAAGA AAGCACTGTG    4293
ACACCGGAAC AATGAGTGTG CATAAACTTC ATCTTGAACT TTAAGGACAG CTGGCCACGA    4353
AGAGCCAGTG TGCTCCCTGC CACGCCGAAA GAGGATGGGT TTACTCTCGT CAAATTTACA    4413
AGCATACGGT TCCTCTGCTC TGAAACCGTG TTCCATGACA CGCCGCTGTA AATTATTTCA    4473
TATGGAACTG TTCGCGTTGG GTGGAGAGAG TATTAAATAT TAACATAGG TCTTCATTTA     4533
TATATGTAAT TTTTTAATGA AAATGTAACT TTCCTCACAG CACATTTTTT TTCTCTTGGA    4593
ATGTGGAACT GAGGTATTCA ATGTTTTGTT TTAAAGAGTG GGAAGAATAC TTAAAACAAG    4653
GCTAAAAAGA GTAGACTAGG AGATGATCCT TGTTTTAAGA TTCTAATTCA GAAAAATAAT    4713
ATAATATGAA TCATAGTGCC ATAGAAGGTT CTGGACTGTA TAGTTGTACT TGCTGATGCT    4773
GTCTCTTGTA ATATAAACTT GATGTCGAGC TGAGTTCCTT TTAAGAATTA AGCTAAGTTT    4833
TGTAATTTTT TTTTTTTCCA AACCGAAGGA GGATGTATTC TACTGGGGTG TTTTCAAGTG    4893
TCGGCTTAGA ATTGGAAGTT GAATGGAAGC AAAGTTCAAC AAAGAGAGGA AGCCACAGAC    4953
TTCCATTGTA AATACTGTAG AGAGAGACAT GAGCGATCCC TTCAAGTCAA AAATCTCTCT    5013
TTGGAATGAA GAATGTGGGT GTTTATAAAT TCTGAAAATG TCTTTCTGTT CATAATAAAC    5073
TAGACACTGT TGGTCCCTCC CCACCCCCAC TTCTATAAGC CTTTCCCCCG GA            5125
```

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

Leu Glu Tyr Tyr Glu Asn Glu Lys
                   5

( 2 ) INFORMATION FOR SEQ ID NO:6:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

Glu Gln Gln Gln Gln Gln Gln Gln Gln Gln Gln Ser Ile Leu Xaa Pro
                5                       10                      15
Pro Glu (2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:7:

Leu Ser Ser Glu Thr Phe Ser Ala Pro Xaa Pro
                5                       10

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:8:

Val Val Ala Val Asp Xaa Gly Ile Lys
                5

(2) INFORMATION FOR SEQ ID NO:9:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:9:

Glu Glu Thr Gly Ser Thr Xaa Tyr Met Asn Met Asp Leu Gly Pro Gly
                5                       10                      15
Glu Ala (2) INFORMATION FOR SEQ ID NO:10:

(i) SEQUENCE CHARACTERISTICS:
        (A) LENGTH: 14 amino acids
        (B) TYPE: amino acids
        (C) STRANDEDNESS: single
        (D) TOPOLOGY: linear (xi) SEQUENCE DESCRIPTION: SEQ ID NO:10:

Xaa Leu Pro Asp Ala Glu Met Gly Xaa Ser Pro Ala Xaa Thr
                5                       10

(2) INFORMATION FOR SEQ ID NO:11:

(i) SEQUENCE CHARACTERISTICS:
        (A) LENGTH: 12 amino acids
        (B) TYPE: amino acids
        (C) STRANDEDNESS: single
        (D) TOPOLOGY: linear (xi) SEQUENCE DESCRIPTION: SEQ ID NO:11:

Ser Val Ser Ala Pro Gln Gln Ile Ile Asn Pro Ile
                5                       10

(2) INFORMATION FOR SEQ ID NO:12:

( i ) SEQUENCE CHARACTERISTICS:
   ( A ) LENGTH: 6 amino acids
   ( B ) TYPE: amino acid
   ( C ) STRANDEDNESS: single
   ( D ) TOPOLOGY: linear ( x i ) SEQUENCE DESCRIPTION: SEQ ID NO:12:

Asn Leu Ile Gly Ile Tyr
                    5

( 2 ) INFORMATION FOR SEQ ID NO:13:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:13:

Gly Gln Xaa Leu Thr Met Ala Asn
                5

( 2 ) INFORMATION FOR SEQ ID NO:14:

( i ) SEQUENCE CHARACTERISTICS:
      ( A ) LENGTH: 19 amino acids
      ( B ) TYPE: amino acid
      ( C ) STRANDEDNESS: single
      ( D ) TOPOLOGY: linear ( x i ) SEQUENCE DESCRIPTION: SEQ ID NO:14:

Tyr Ile Pro Gly Ala Thr Met Thr Gly Ser Pro Ala Leu Thr Gly Asp
                    5                       1 0                     1 5

Glu Ala Arg ( 2 ) INFORMATION FOR SEQ ID NO:15:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( x i ) SEQUENCE DESCRIPTION: SEQ ID NO:15:

Ser Phe Ala Phe Val Ser
                    5

( 2 ) INFORMATION FOR SEQ ID NO:16:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( x i ) SEQUENCE DESCRIPTION: SEQ ID NO:16:

Xaa Ile Ser His Ala Ile Ser Glu His Val Glu Asp Ser Gly Val His
                    5                       1 0                     1 5

Ser ( 2 ) INFORMATION FOR SEQ ID NO:17:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( x i ) SEQUENCE DESCRIPTION: SEQ ID NO:17:

Xaa Leu Gly Ala Ser Pro Pro Asn Ala Xaa Thr Ala Pro Xaa Xaa Xaa
                  5                   10                  15
Arg ( 2 ) INFORMATION FOR SEQ ID NO:18:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( x i ) SEQUENCE DESCRIPTION: SEQ ID NO:18:

Xaa Pro Pro Xaa Thr Phe Gln Xaa Val Xaa Xaa Pro
                  5                   10

( 2 ) INFORMATION FOR SEQ ID NO:19:

( i ) SEQUENCE CHARACTERISTICS:
      ( A ) LENGTH: 24 amino acids
      ( B ) TYPE: amino acid
      ( C ) STRANDEDNESS: single
      ( D ) TOPOLOGY: linear ( x i ) SEQUENCE DESCRIPTION: SEQ ID NO:19:

Ser Ala Val Thr Gly Pro Gly Glu Phe Xaa Met Gln Val Asp Asp Ser
                  5                   10                  15
Val Val Ala Gln Asn Met Xaa Glu
                 20

( 2 ) INFORMATION FOR SEQ ID NO:20:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( x i ) SEQUENCE DESCRIPTION: SEQ ID NO:20:

Gln Ala Asp Ala Val Tyr Phe Leu Pro Ile Thr Pro Gln Phe Val Thr
                  5                   10                  15
Glu Val Ile Xaa
                 20

( 2 ) INFORMATION FOR SEQ ID NO:21:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:21:

Thr Phe Glu Glu Ser Phe Gln Lys
                  5

( 2 ) INFORMATION FOR SEQ ID NO:22:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( x i ) SEQUENCE DESCRIPTION: SEQ ID NO:22:

```
Leu Phe Ala Thr Glu Ala Thr Ser Asp Xaa
                 5                   10
```

( 2 ) INFORMATION FOR SEQ ID NO:23:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:23:

```
Thr Ala Asp Asp Ser Xaa Ile Xaa Leu Leu
                 5                   10
```

( 2 ) INFORMATION FOR SEQ ID NO:24:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:24:

```
Thr Arg Asp Ile Tyr Glu Thr Asp Tyr Tyr Arg Lys
                 5                   10
```

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:25:

```
Gly Xaa Gly Xaa Xaa Gly
                 5
```

( 2 ) INFORMATION FOR SEQ ID NO:26:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:26:

```
Glu Tyr Tyr Glu
             4
```

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:27:

```
Gly Val Gly Glu Ala Gly
                 5
```

( 2 ) INFORMATION FOR SEQ ID NO:28:

( i ) SEQUENCE CHARACTERISTICS:
        ( A ) LENGTH: 4 amino acids
        ( B ) TYPE: amino acid
        ( C ) STRANDEDNESS: single ( D ) TOPOLOGY: linear ( x i ) SEQUENCE DESCRIPTION: SEQ ID NO:28:

Ala Xaa Lys Ile
              4

( 2 ) INFORMATION FOR SEQ ID NO:29:

( i ) SEQUENCE CHARACTERISTICS:
        ( A ) LENGTH: 1155 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Met Ala Ser Pro Pro Asp Thr Asp Gly Phe Ser Asp Val Arg Lys Val
 1               5                  10                      15

Gly Tyr Leu Arg Lys Pro Lys Ser Met His Lys Arg Phe Phe Val Leu
             20              25                      30

Arg Ala Ala Ser Glu Ala Gly Gly Pro Ala Arg Leu Glu Tyr Tyr Glu
         35              40                  45

Asn Glu Lys Lys Trp Arg His Lys Ser Ser Ala Pro Lys Arg Ser Ile
     50              55                  60

Pro Leu Glu Ser Cys Phe Asn Ile Asn Lys Arg Ala Asp Ser Lys Asn
 65              70                  75                      80

Lys His Leu Val Ala Leu Tyr Thr Arg Asp Glu His Phe Ala Ile Ala
                 85                  90                      95

Ala Asp Thr Glu Ala Glu Gln Asp Thr Trp Tyr Gln Ala Leu Leu Gln
             100                 105                 110

Leu His Asn Arg Ala Lys Ala His His Asp Gly Ala Gly Gly Gly Cys
             115                 120                 125

Gly Gly Ser Cys Ser Gly Ser Ser Gly Val Gly Glu Ala Gly Glu Asp
     130                 135                 140

Leu Ser Tyr Asp Thr Gly Pro Gly Pro Ala Phe Lys Glu Val Trp Gln
145                 150                 155                 160

Val Ile Leu Lys Pro Lys Gly Leu Gly Gln Thr Lys Asn Leu Ile Gly
                 165                 170                 175

Ile Tyr Arg Leu Ser Leu Thr Ser Lys Thr Ile Ser Phe Val Lys Leu
             180                 185                 190

Asn Ser Glu Ala Ala Ala Val Val Leu Gln Leu Met Asn Ile Arg Arg
         195                 200                 205

Cys Gly His Ser Arg Ala Met Ser His Glu Phe Arg Pro Arg Thr Lys
     210                 215                 220

Ser Gln Ser Ser Ser Ser Cys Ser Asn Pro Ile Ser Val Pro Leu Arg
225                 230                 235                 240

Arg His His Leu Asn Asn Pro Pro Pro Ser Gln Val Gly Leu Thr Arg
                 245                 250                 255

Arg Ser Arg Thr Glu Ser Ile Thr Ala Thr Ser Pro Ala Ser Met Val
             260                 265                 270

Gly Gly Lys Pro Gly Ser Phe Arg Val Arg Ala Ser Ser Asp Gly Glu
         275                 280                 285

Gly Thr Met Ser Arg Pro Ala Ser Val Asp Gly Ser Pro Val Ser Pro
     290                 295                 300

Ser Thr Asn Arg Thr His Ala His Arg His Arg Gly Ser Ser Arg Leu
305                 310                 315                 320

His Pro Pro Leu Asn His Ser Arg Ser Ile Pro Met Pro Ser Ser Arg
```

|     |     |     |     |     |     | 325 |     |     |     |     | 330 |     |     |     |     | 335 |     |
|-----|-----|-----|-----|-----|-----|-----|-----|-----|-----|-----|-----|-----|-----|-----|-----|-----|-----|

Cys Ser Pro Ser Ala Thr Ser Pro Val Ser Leu Ser Ser Ser Ser Thr
               340              345              350

Ser Gly His Gly Ser Thr Ser Asp Cys Leu Phe Pro Arg Arg Ser Ser
           355              360              365

Ala Ser Val Ser Gly Ser Pro Ser Asp Gly Gly Phe Ile Ser Ser Asp
       370              375              380

Glu Tyr Gly Ser Ser Pro Cys Asp Phe Arg Ser Ser Phe Arg Ser Val
385              390              395              400

Thr Pro Asp Ser Leu Gly His Thr Pro Pro Ala Arg Gly Glu Glu Glu
               405              410              415

Leu Ser Asn Tyr Ile Cys Met Gly Gly Lys Gly Ala Ser Thr Leu Thr
               420              425              430

Ala Pro Asn Gly His Tyr Ile Leu Ser Arg Gly Gly Asn Gly His Arg
           435              440              445

Tyr Ile Pro Gly Ala Thr Met Gly Thr Ser Pro Ala Leu Thr Gly Asp
       450              455              460

Glu Ala Ala Gly Ala Ala Asp Leu Asp Asn Arg Phe Arg Lys Arg Thr
465              470              475              480

His Ser Ala Gly Thr Ser Pro Thr Ile Ser His Gln Lys Thr Pro Ser
               485              490              495

Gln Ser Ser Val Val Ser Ile Glu Glu Tyr Thr Glu Met Met Pro Ala
           500              505              510

Ala Tyr Pro Pro Gly Gly Gly Ser Gly Gly Arg Leu Pro Gly Tyr Arg
       515              520              525

His Ser Ala Phe Val Pro Thr His Ser Tyr Pro Glu Glu Gly Leu Glu
   530              535              540

Met His His Leu Glu Arg Arg Gly Gly His His Arg Pro Asp Ser Ser
545              550              555              560

Asn Leu His Thr Asp Asp Gly Tyr Met Pro Met Ser Pro Gly Val Ala
               565              570              575

Pro Val Pro Ser Asn Arg Lys Gly Asn Gly Asp Tyr Met Pro Met Ser
           580              585              590

Pro Lys Ser Val Ser Ala Pro Gln Gln Ile Ile Asn Pro Ile Arg Arg
       595              600              605

His Pro Gln Arg Val Asp Pro Asn Gly Tyr Met Met Met Ser Pro Ser
   610              615              620

Gly Ser Cys Ser Pro Asp Ile Gly Gly Gly Ser Cys Ser Ser Ser Ser
625              630              635              640

Ile Ser Ala Ala Pro Ser Gly Ser Ser Tyr Gly Lys Pro Trp Thr Asn
               645              650              655

Gly Val Gly Gly His His Thr His Ala Leu Pro His Ala Lys Pro Pro
           660              665              670

Val Glu Ser Gly Gly Gly Lys Leu Leu Pro Cys Thr Gly Asp Tyr Met
       675              680              685

Asn Met Ser Pro Val Gly Asp Ser Asn Thr Ser Ser Pro Ser Glu Cys
   690              695              700

Tyr Tyr Gly Pro Glu Asp Pro Gln His Lys Pro Val Leu Ser Tyr Tyr
705              710              715              720

Ser Leu Pro Arg Ser Phe Lys His Thr Gln Arg Pro Gly Glu Pro Glu
               725              730              735

Glu Gly Ala Arg His Gln His Leu Arg Leu Ser Ser Ser Ser Gly Arg
               740              745              750

```
Leu  Arg  Tyr  Thr  Ala  Thr  Ala  Glu  Asp  Ser  Ser  Ser  Thr  Ser  Ser
          755                 760                 765

Asp  Ser  Leu  Gly  Gly  Gly  Tyr  Cys  Gly  Ala  Arg  Pro  Glu  Ser  Ser  Val
          770                 775                 780

Thr  His  Pro  His  His  His  Ala  Leu  Gln  Pro  His  Leu  Pro  Arg  Lys  Val
785                      790                 795                           800

Asp  Thr  Ala  Ala  Gln  Thr  Asn  Ser  Arg  Leu  Ala  Arg  Pro  Thr  Arg  Leu
                    805                      810                 815

Ser  Leu  Gly  Asp  Pro  Lys  Ala  Ser  Thr  Leu  Pro  Arg  Val  Arg  Glu  Gln
               820                      825                      830

Gln  Gln  Gln  Gln  Gln  Gln  Gln  Gln  Gln  Ser  Ser  Leu  His  Pro  Pro  Glu
               835                      840                 845

Pro  Lys  Ser  Pro  Gly  Glu  Tyr  Val  Asn  Ile  Glu  Phe  Gly  Ser  Gly  Gln
          850                 855                      860

Pro  Gly  Tyr  Leu  Ala  Gly  Pro  Ala  Thr  Ser  Arg  Ser  Ser  Pro  Ser  Val
865                      870                 875                           880

Arg  Cys  Leu  Pro  Gln  Leu  His  Pro  Ala  Pro  Arg  Glu  Glu  Thr  Gly  Ser
               885                 890                      895

Glu  Glu  Tyr  Met  Asn  Met  Asp  Leu  Gly  Pro  Gly  Arg  Arg  Ala  Thr  Trp
               900                 905                      910

Gln  Glu  Ser  Gly  Gly  Val  Glu  Leu  Gly  Arg  Val  Gly  Pro  Ala  Pro  Pro
               915                 920                      925

Gly  Ala  Ala  Ser  Ile  Cys  Arg  Pro  Thr  Arg  Ser  Val  Pro  Asn  Ser  Arg
          930                 935                      940

Gly  Asp  Tyr  Met  Thr  Met  Gln  Ile  Gly  Cys  Pro  Arg  Gln  Ser  Tyr  Val
945                      950                      955                      960

Asp  Thr  Ser  Pro  Val  Ala  Pro  Val  Ser  Tyr  Ala  Asp  Met  Arg  Thr  Gly
               965                      970                      975

Ile  Ala  Ala  Glu  Lys  Val  Ser  Leu  Pro  Arg  Thr  Thr  Gly  Ala  Ala  Pro
               980                 985                      990

Pro  Pro  Ser  Ser  Thr  Ala  Ser  Ala  Ser  Ala  Ser  Val  Lys  Val  Ile  Arg
          995                 1000                     1005

Ala  Asp  Thr  Gln  Gly  Cys  Arg  Arg  Arg  His  Ser  Ser  Glu  Thr  Phe  Ser
          1010                1015                     1020

Ala  Pro  Thr  Arg  Ala  Ala  Asn  Thr  Val  Ser  Phe  Gly  Ala  Gly  Ala  Ala
1025                     1030                1035                          1040

Gly  Gly  Gly  Ser  Gly  Gly  Gly  Ser  Glu  Asp  Val  Lys  Arg  His  Ser  Ser
               1045                1050                     1055

Ala  Ser  Phe  Glu  Asn  Val  Trp  Leu  Arg  Pro  Gly  Asp  Leu  Gly  Gly  Ala
               1060                1065                     1070

Ser  Lys  Glu  Ser  Ala  Pro  Gly  Cys  Gly  Ala  Ala  Gly  Gly  Leu  Glu  Lys
          1075                1080                     1085

Ser  Leu  Asn  Tyr  Ile  Asp  Leu  Asp  Leu  Val  Lys  Asp  Val  Lys  Gln  His
          1090                1095                     1100

Pro  Gln  Asp  Cys  Pro  Ser  Gln  Gln  Gln  Ser  Leu  Pro  Pro  Pro  Pro  Pro
1105                     1110                1115                          1120

His  Gln  Pro  Leu  Gly  Ser  Asn  Glu  Gly  Ser  Ser  Pro  Arg  Arg  Ser  Ser
                    1125                1130                     1135

Glu  Asp  Leu  Ser  Thr  Tyr  Ala  Ser  Ile  Asn  Phe  Gln  Lys  Gln  Pro  Glu
               1140                1145                     1150

Asp  Arg  Gln
          1155
```

INSULIN RECEPTOR SUBSTRATE

This is a divisional of application Ser. No. 07/962,023, filed on Oct. 15, 1992 now U.S. Pat. No. 5,260,200, which is a continuation of application Ser. No. 07/643,982, filed Jan. 18, 1991, now abandoned.

BACKGROUND OF THE INVENTION

The invention relates to insulin metabolism and more specifically to the insulin receptor substrate (IRS-1) and the gene that encodes it.

Insulin initiates its metabolic and growth promoting effects upon binding to its tetrameric receptor (Kahn et al., 1988, J. Clin. Invest. 82:1151–1156, hereby incorporated by reference; Freychet et al., 1976, Proc. Natl. Acad. Sci. (USA), 68:1833–1837, hereby incorporated by reference; Cuatrecasas, 1972, Proc. Natl. Acad. Sci. (USA) 69:1277–1281, hereby incorporated by reference) thereby activating a kinase in the β-subunit to catalyze the intramolecular autophosphorylation of specific tyrosine residues of its own β-subunits (Roth, R. A., 1990, in Handbook of Experimental Pharmacology, Vol. 92, Cuatrecasas, P., and Jacobs, S., eds., Springer-Verlag, hereby incorporated by reference; Kasuga et al., 1982, Nature 298:667–669, hereby incorporated by reference; Kasuga et al., 1982, Science 215:185–189, hereby incorporated by reference). Autophosphorylation enhances receptor tyrosine kinase activity toward other protein substrates (Avruch et al., 1982, J. Biol. Chem. 256:15162–15169, hereby incorporated by reference; Roth et al., 1983, Science, 219:299–301, hereby incorporated by reference, Rosen et al., 1983, Proc. Natl. Acad. Sci. (USA) 80:3237–3240, hereby incorporated by reference). Considerable evidence demonstrates that insulin receptor tyrosine kinase activity is essential for many, if not all of the biological effects of insulin (Odawara et al., 1989, Science 245:66–68, hereby incorporated by reference; Taira et al., 1989, Science, 245:63–66, hereby incorporated by reference; Moller et al., 1988, New Engl. J. Med., 319:1526–1529, hereby incorporated by reference; Ellis et al., 1986, Cell, 45:721–732, hereby incorporated by reference; Chou et al., 1987, J. Biol. Chem. 262:1842–1846, hereby incorporated by reference; Ebina et al., 1987, Proc. Natl. Acad. Sci., (USA), 84:704–708, hereby incorporated by reference; Maegawa et al., 1988, J. Biol. Chem., 263:12629–2637, hereby incorporated by reference; Morgan et al., 1987, Proc. Natl. Acad. Sci. (USA) 84:41–45, hereby incorporated by reference). However, the exact biochemical mechanisms linking receptor kinase mediated tyrosine phosphorylation to the regulation of cellular metabolic pathways are undefined.

Tyrosine phosphorylation of several cellular proteins and enzymes has been observed during the initial cellular response to some receptor tyrosine kinase-linked polypeptide growth factors, e.g., PDGF-induced phosphorylation of phospholipase C (Meisenhelder et al., 1989, Cell 57:1109–1122, hereby incorporated by reference), 3'-phosphatidyl-inositol (PI-3) kinase (Kaplan et al., 1987 Cell 57:1021–1029, hereby incorporated by reference), and the raf–1 kinase (Morrison et al., 1989, Cell 58:649–657, hereby incorporated by reference). However, the nature of the physiologically relevant cellular protein substrates of the insulin receptor kinase has remained elusive. Although many purified proteins and synthetic peptides can be phosphorylated in vitro by isolated insulin receptors (reviewed in, Rothenberg et al., 1990a, in Handbook of Experimental Pharmacology, Vol 92, Cuatrecasas, P., Jacobs, S. eds., Springer-Verlag, hereby incorporated by reference), these reactions do not occur in vivo. When anti-phosphotyrosine antibodies are used to immunoprecipitate phosphotyrosine-containing proteins which appear in intact cultured cells during insulin stimulation, a protein of approximately $M_r=185$ kDa, designated pp185, appears in extracts of several cell types (White et al., 1987, J. Biol. Chem. 262:9769–9777, hereby incorporated by reference; White et al., 1985, Nature 318:183–186, hereby incorporated by reference; Izumi et al., 1987, J. Biol. Chem 262:1282–1287, hereby incorporated by reference; Beguinot et al., 1988, Biochemistry 27:3222–3228, hereby incorporated by reference; Kadowaki et al., 1987, J. Biol. Chem. 262:7342–7350, hereby incorporated by reference; Condorelli et al., 1989, J. Biol. Chem. 264:12633–12638, hereby incorporated by reference). Additional phosphotyrosyl proteins of lower $M_r$ have also been described in some cell lines (Rothenberg et al., 1990a, supra; Madoff et al., 1988, Biochem. J. 252:7–15, hereby incorporated by reference; Rees-Jones et al., 1985, J. Biol. Chem. 260:4461–4467, hereby incorporated by reference; Bernier et al, 1987, Proc. Natl. Acad. Sci. (USA) 84:1844–1848, hereby incorporated by reference; Heffetz et al., 1989, J. Biol. Chem 264:10126–10132, hereby incorporated by reference; Levenson et al., 1989, J. Biol. Chem. 264:19984–19993, hereby incorporated by reference). The majority of these putative substrates are unidentified, and of all such putative insulin receptor kinase substrates no clear role in insulin signalling has yet been assigned.

SUMMARY OF THE INVENTION

In general, the invention features a purified nucleic acid encoding IRS-1. In preferred embodiments the purified nucleic acid is from a mammal, e.g., a rat or a human, the purified nucleic acid is present in a vector, and the purified nucleic acid is present in a cell, the purified nucleic acid is under the transcriptional control of a heterologous promoter. The invention also includes a homogeneous population of cells, preferably eukaryotic cells, wherein each of the cells contains cloned nucleic acid encoding IRS-1.

In another aspect, the invention features a purified preparation of IRS-1, preferably produced from nucleic acid encoding IRS-1. The invention also includes a method of producing IRS-1, including the steps of: culturing a cell which contains purified nucleic acid which encodes IRS-1 in medium to form a population of cells which expresses IRS-1 and purifying IRS-1 from the cells or from the culture medium.

In another aspect the invention features a method of purifying a phosphoprotein including in the following order: (a) providing a sample containing the phosphoprotein in the phosphorylated state; (b) contacting the sample with denaturant and a reducing agent under conditions, e.g., heating, or boiling, that inhibit the removal of phosphate groups from the phosphoprotein; (c) decreasing the concentration of the denaturant sufficiently to allow an antiphospho-amino antibody e.g., an anti-phosptyrosive antibody, to bind to the phosphoprotein; and (d) contacting the phosphoprotein with an anti-phosphoamino antibody and purifying the phosphoprotein by virtue of its affinity for the antibody. In preferred embodiments, in step (d), the antibody is bound to a substrate, the sample is contacted with the bound antibody, and the phosphoprotein is eluted from the bound antibody.

In another aspect the invention features a method of diagnosing a disease, e.g., insulin-related disease, e.g., an insulin resistant insulin-related disease, e.g., Type II diabetes, in a mammal, e.g., in a human. In preferred embodiments the disease is characterized by an abnormality in IRS-1 structure or metabolism. The method includes measuring an aspect of IRS-1 metabolism in the mammal, an abnormal level of IRS-1 metabolism being diagnostic of the disease. The metabolism of a substance, as used herein, means any aspect of the metabolism, expression, function, or action of the substance. Preferred embodiments include those in which: the measurement includes measuring the level of IRS-1 in a tissue sample (a tissue sample as used herein means any suitable sample e.g., a sample including classic insulin sensitive tissue, e.g., muscle, fat or liver tissue, or a sample including more easily accessible tissue, e.g., circulating blood cells or fibroblasts), taken from the mammal; the measurement includes measuring the level of phosphorylation of the IRS-1 in a tissue sample taken from the mammal; the measurement includes measuring the level of kinase activity of IRS-1; and the measurement includes measuring the amount of IRS-1 encoding RNA in a tissue sample taken from the mammal. An insulin-related disease, as used herein, is a disease, disorder, or condition in which some aspect of insulin expression metabolism, or action is disrupted or, a disease in which insulin action contributes to the disease. An insulin resistant insulin-related disease, as used herein, is any disease, disorder, or condition in which a normal amount of insulin results in a less than normal biological response. Examples of insulin resistant diseases include Type II diabetes, obesity, aging related insulin resistance, and insulin resistance that arises secondary to infections, hormonal disorders, or other causes.

The invention also features a method of diagnosing, preferably prenatally, an insulin-related disease, e.g., an insulin resistant insulin-related disease, e.g., Type II diabetes, in a mammal, e.g., a human, including determining the structure of the gene which expresses IRS-1, an abnormal structure being diagnostic of the disease.

The invention also includes a method of assaying an effect of a therapeutic agent on IRS-1 metabolism, e.g., an agent used to treat an insulin-related disease in a mammal, e.g., a human. (A therapeutic agent, as used herein, can be any substance or treatment.) The method includes administering the agent to a test organism e.g., a cultured cell or a mammal, and measuring the effect of the drug on an aspect of IRS-1 metabolism, e.g., measuring the level of IRS-1 expression, the cellular or intra-cellular distribution of IRS-1, or the level of the IRS-1 phosphorylation. A change in an aspect of IRS-1 metabolism indicates an effect of the agent. In preferred embodiments the insulin-related disease is an insulin resistant disease and the change in an aspect of metabolism is a change in the level of IRS-1 phosphorylation.

The invention also includes a method of assaying an effect of a therapeutic agent which mimics a first effect of insulin, the first effect mediated by IRS-1, without mimicking a second effect of insulin. The method includes administering the agent to a test organism, e.g., a cell grown in culture or a mammal, and measuring a change in an aspect of IRS-1 metabolism, e.g., the level of IRS-1 expression, the kinase activity of IRS-1, the cellular or intra-cellular distribution of IRS-1, or the level of the IRS-1 phosphorylation. A change in an aspect of IRS-1 metabolism indicates an effect of the agent.

The invention also features a method of assaying an effect of a therapeutic agent which alters the ability of a tyrosine kinase to phosphorylate a substrate which includes the amino acid sequence YMXM (SEQ ID NO:1). The method includes administering the drug to a test organism, e.g., a cultured cell or a mammal, and measuring the level of phosphorylation of a substrate, which includes the amino acid sequence YMXM (SEQ ID No: 1), e.g., a naturally occurring substrate of the tyrosine kinase or a synthetic substrate.

The invention also includes a method of treating a mammal e.g., a human, suffering from a disease, disorder, or condition caused by the phosphorylation of a substrate of a tyrosine kinase, the substrate including the amino acid sequence YMXM (SEQ ID No: 1). The tyrosine kinase may be, e.g., a receptor tyrosine kinase, e.g., insulin receptor, epidermal growth factor (EGF) receptor, platelet derived growth factor, (PDGF) receptor, or insulin-like growth factor (ILG) receptor, or an oncogene product, e.g., the src, abl, or fms gene product. The method includes administering a therapeutically effective amount of a therapeutic agent, e.g., IRS-1, which includes the amino acid sequence YMXM (SEQ ID No: 1). In preferred embodiments the substance blocks phosphorylation of the naturally occurring substrate by competitive or non-competitive inhibition of the naturally occurring substrate.

The invention also features a method of treating a mammal e.g., a human, suffering from a disease caused by IRS-1, e.g., by an abnormality of IRS-1 metabolism. The method includes administering to the mammal a therapeutically effective amount of a therapeutic agent, e.g., IRS-1, agent which alters an aspect of the metabolism of IRS-1, e.g., the level of IRS-1 phosphorylation. In preferred embodiments the abnormality includes the inability of the insulin receptor to respond to insulin by phosphorylating IRS-1. In other preferred embodiments the agent increases the phosphorylation of IRS-1, e.g., by increasing the activity of a kinase or decreasing the activity of a phosphatase. In other preferred embodiments the agent decreases the phosphorylation of IRS-1, e.g., by decreasing the activity of a kinase or increasing the activity of a phosphatase.

The invention also features a method of treating a mammal, e.g., a human, suffering from a disease caused by a tyrosine kinase. The method includes administering to the mammal a therapeutically effective amount of a therapeutic agent which modifies the ability of IRS-1 to alter the phosphorylation of the tyrosine kinase, thereby altering the activity of the tyrosine kinase. In preferred embodiments the tyrosine kinase is the product of an oncogene.

The invention also features a method of treating a mammal, e.g., a human, suffering from a disease characterized by abnormal cell proliferation. Abnormal cell proliferation, as used herein, includes both neoplastic and non-neoplastic diseases, and thus includes diseases such as cancer and atherosclerosis. The method includes administering to said mammal a therapeutically effective amount of a therapeutic agent, e.g., IRS-1, which alters an aspect of IRS-1 metabolism. In preferred embodiments the aspect of IRS-1 metabolism is IRS-1 phosphorylation. In other preferred embodiments the aspect of IRS-1 metabolism is the level of kinase activity of IRS-1.

IRS-1, as used herein, means insulin receptor substrate, e.g., mammalian insulin receptor substrate, e.g., rat or human insulin receptor substrate.

Purified nucleic acid, as used herein, means nucleic acid which is separated from other nucleic acid with which it is naturally joined covalently.

A vector, as used herein, is an autonomously replicating nucleic acid molecule.

A heterologous promoter, as used herein is a promoter which is not naturally associated with a gene or a purified nucleic acid.

A nucleic acid encoding IRS-1, as used herein, is a nucleic acid, preferably a DNA molecule, which encodes a protein which, in its natural state, is phosphorylated by the insulin receptor, preferably in an insulin dependent fashion, and which has at least 70%, preferably 80%, and more preferably 90% homology to IRS-1 or which hybridizes to IRS-1 under conditions of high stringency.

An anti-phosphoamino antibody, as used herein, is an antibody directed against a phosphorylated amino acid, e.g., an antibody directed against phosphotyrosine or phosphoserine.

A denaturant, as used herein, is an agent, e.g., a detergent, e.g., SDS, which disrupts the tertiary structure of a protein and thereby inhibits the enzymatic activity of the protein.

A reducing agent, as used herein, is an agent which disrupts S—S bonds.

A phosphoprotein, as used herein, is a phosphorylated protein or polypeptide.

A purified preparation of IRS-1, as used herein, means IRS-1 that has been separated from other proteins, lipids, and nucleic acids with which it naturally occurs. Preferably, the IRS-1 is also separated from substances, e.g., antibodies or gel matrix, e.g, polyacrylimide, which are used to purify it. Preferably, the IRS-1 constitutes at least 10% dry weight of the purified preparation. Preferably, the preparation contains sufficient IRS-1 to allow protein sequencing.

The method of the invention can be used to diagnose the presence of diseases characterized by an abnormality in the structure or metabolism of IRS-1 or the insulin receptor. The invention allows for the analysis of various aspects of insulin metabolism, e.g., for the determination of insulin receptor function, e.g., the detection of insulin-stimulated substrate phosphorylation. The invention also provides useful tools for the testing and development of therapeutic agents used to treat insulin or IRS-1 related diseases.

Methods of the invention allow for rapid and high yield purification of phosphoproteins. The denaturation step prevents dephosphorylation and thus allows efficient anti-phosphoamino antibody based purification.

Methods of the invention also allow the treatment of a variety of diseases, e.g., insulin related diseases, insulin resistant diseases, diseases characterized by abnormal cellular proliferation, and diseases caused by the phosphorylation of a substrate by a tyrosine kinase, by intervening in aspects of IRS-1 metabolism. Other features and advantages of the invention will be apparent from the following description of the preferred embodiments and from the claims.

DESCRIPTION OF THE PREFERRED EMBODIMENTS

The drawings are first described.

Drawings FIG. 1 is a graph of the effect of insulin on phosphorylation of pp175 and the β-subunit of the insulin receptor.

FIG. 12 is the sequence of rat IRS-1 (SEQ ID NO: 4).

Figure 15A:
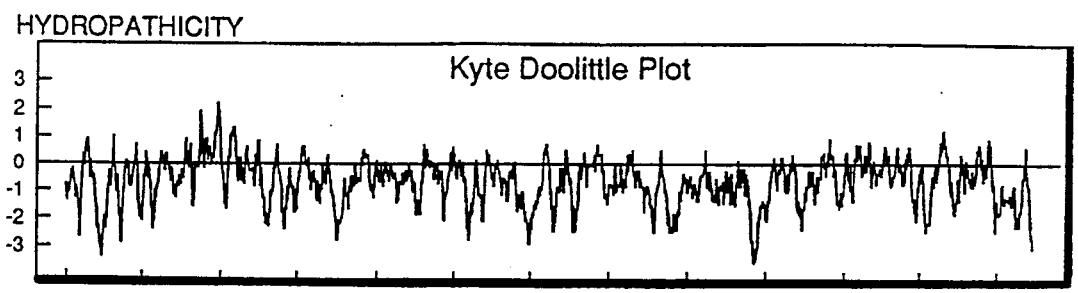
Figure 15B:
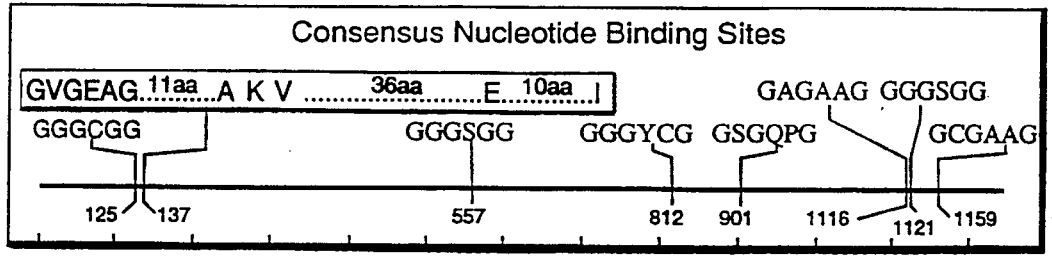
Figure 15C:
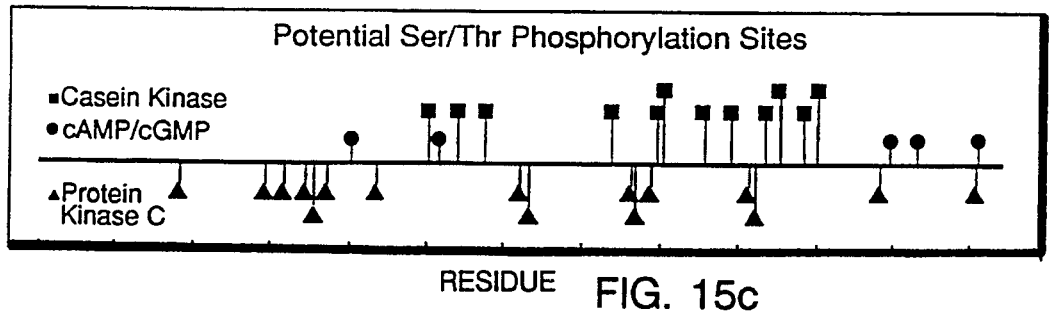

FIGS. 15a, 15b, and 15c are diagrams of structural features of rat IRS-1.

Figure 16:
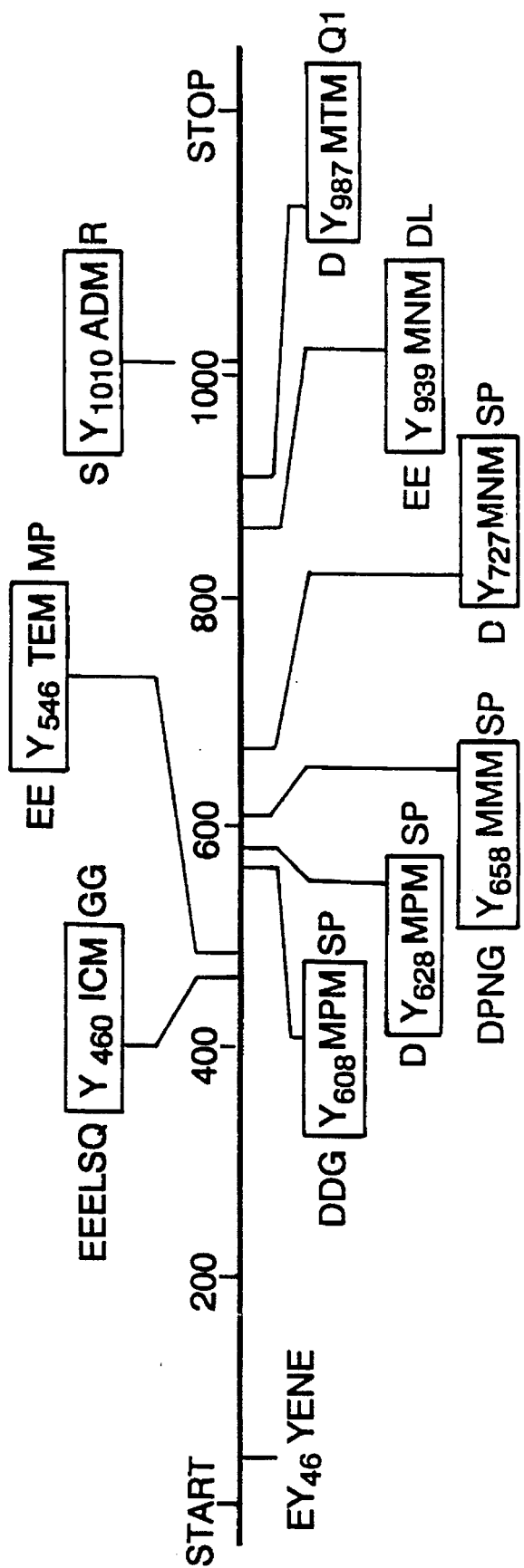

FIG. 16 is a map of the putative phosphorylation sites in IRS-1.

Figure 17:
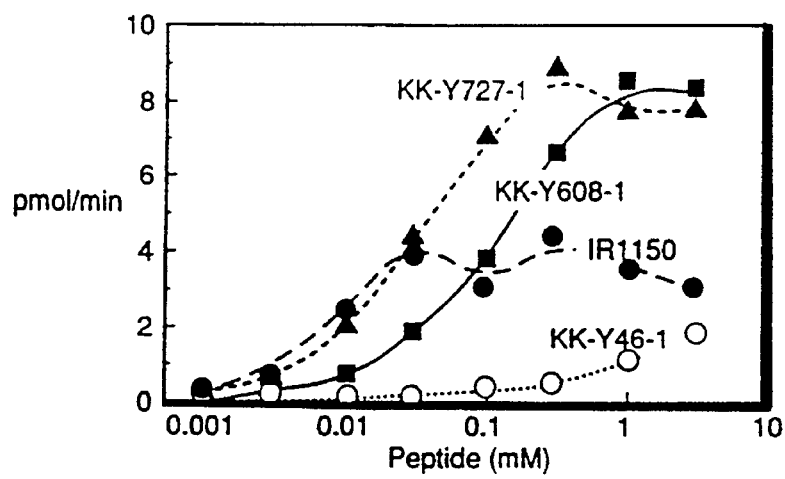

FIG. 17 is a graph of the effect of insulin stimulation of phosphorylation of synthetic peptides.

Figure 18:
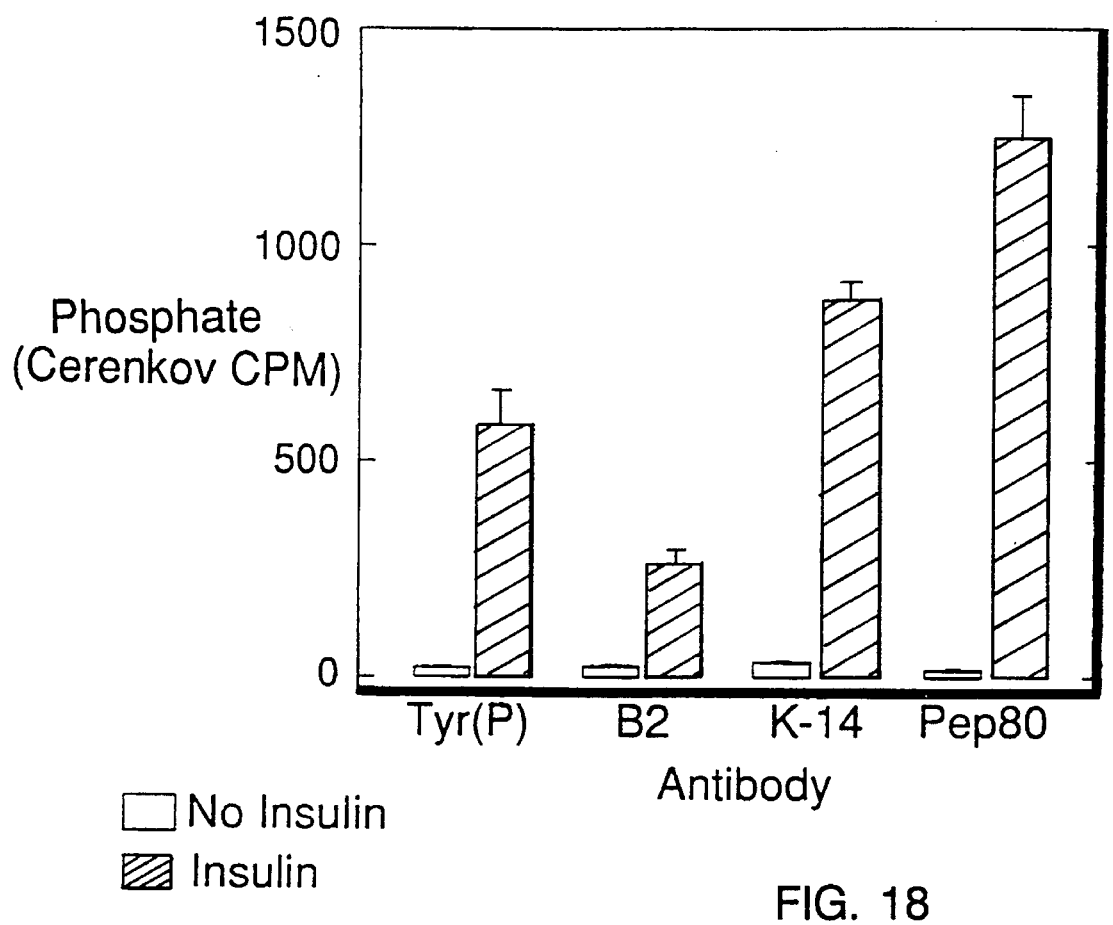

FIG. 18 is a graph of the effect of insulin stimulation on phosphatidyl inositol 3-kinase.

Purification and Partial Sequence Analysis of pp185, the Major Cellular Substrate of the Insulin Receptor Tyrosine Kinase Preparative Purification of pp185 pp185 was purified from liver using SDS denaturation/ TCA precipitation, coupled with preparative-scale anti-phosphotyrosine antibody immunoaffinity chromatography. Following infusion of insulin total liver extracts of denatured proteins were prepared from SDS-homogenates. After dissolution in base and neutralization, each liver extract was passed through a column of immobilized anti-phosphotyrosine antibody. The column was washed, and the adsorbed phosphotyrosyl proteins were eluted from the affinity matrix with p-nitrophenyl phosphate (pNPP). (The method is described in detail below).

The eluted phosphotyrosyl proteins were analyzed by anti-phosphotyrosine Western blotting and by direct silver-staining, as described below. The pNPP-eluted proteins in the Western blot contain a $M_r$=120 kDa insulin-insensitive protein, and also the insulin-stimulated pp185 and the 95 kDa insulin receptor β-subunit. When these same pNPP-eluted phosphotyrosyl proteins were visualized with a sensitive silver-stain, intense broad bands appear which correspond to the $M_r$=120 kDa protein, and to the insulin-receptor β-subunit. However, at the position corresponding to pp185 there appear two co-migrating bands: one broad band which stains weakly, the other quite narrow. This latter band is also equally evident in the absence of insulin. The broad, poorly staining band detected only after insulin stimulation appears to be authentic pp185. The narrow band, co-migrating at $M_r$=185 kDa, appear to be co-purifying contaminant (not containing phosphotyrosine) which partially and non-specifically eluted from the anti-phosphotyrosine antibody column together with the authentic phosphotyrosyl proteins. This is supported by the presence of this same sharp contaminant band at 185 kDa among those other proteins which were non-specifically absorbed to the affinity column matrix and were not removed by the column washing procedures, but which were dissociable from the affinity matrix by directly heating the matrix in Laemmli sample buffer.

To estimate recoveries of the phosphotyrosyl proteins, total amino acid analysis (described below) was performed on a portion of each of the phosphotyrosyl bands. After separation by 1D-SDS PAGE, the phosphotyrosyl bands were electrotransferred to PVDF membranes, located by Coomassie Blue stain, and each band excised. The total amino acid content and composition of each band was obtained, following in situ hydrolysis, on an automated amino acid analyzer. From 50 insulin-stimulated livers, 340 picomoles of the 95 kDa insulin receptor β-subunit, 196 pmoles of the 120 kDa band, and 108 pmoles of the combined $M_r$=185 kDa bands were removed. Based on silver-stained gels and colloidal gold-stained nitrocellulose electroblots it is estimated that about half of the protein in the combined $M_r$=185 kDa band was pp185.

Details of the purification procedure are as follows. SDS-denatured protein extracts were prepared from whole livers of 3-day fasted (preliminary experiments showed that prolonged fasting increased the insulin-stimulated tyrosine phosphorylation of pp185 about 2.5 fold) male rats (200–300 gram initial body weight), following an intraportal infusion of insulin ($10^{-6}$M) or 0.9% NaCl vehicle for 30 seconds, as described below. 60 grams of dry liver protein precipitate (from a total of 50 livers) was quickly dissolved in 1200 mls of 0.1N NaOH with vigorous agitation for 5 minutes at 22° C., and the base neutralized by addition of 4800 mls of 100 mM Tris-HCl, to a final pH of 7.4 (The preparation of dry liver protein precipitate is described below). The following additions were made to this solution: EDTA, 1 mM; $NaN_3$, 0.02%; leupeptin and aprotinin, 1 ug/ml each; PMSF, 0.1 mM.

After centrifugation (143,000×g at $r_{max}$) for 1 hour at 18° C. in a Beckman Type 35 rotor, the clear supernatant was filtered (0.45 uM cellulose/PVC, Miller-HA), and then passed over a 15×1 cm column containing 12 mls of immobilized anti-phosphotyrosine antibody (aPY-Ab) Protein A-TrisAcryl matrix (described below), at 0.8 mls/min., at 4° C. The column was sequentially washed at 1 ml/min. with 30 bed volumes of 1% Triton X-100, 0.1% SDS, 100 mM NaCl, 50 mM Tris, pH 7.3 at 22° C., and then with 30 bed volumes of the same buffer lacking NaCl, and finally at 22° C. with 1 bed volume of 50 mM Tris, pH 7.2. The adsorbed proteins were eluted at 22° C. for 2 hours with 4 bed volumes of 100 mM pNPP in 0.025% SDS, 50 mM Tris, pH 7.2. The eluate was made 5 mM in DTT, and then simultaneously dialyzed (against 0.05% SDS, 5 mM DTT, 50 mM Tris, pH 7.2) and concentrated 125-fold in vacuo at 22° C. in a Micro-ProDiCon apparatus using PA-15 membranes (Bio-Molecular Dynamics Co., Beaverton, Oreg.). The concentrated sample was made 10% in sucrose, 50 mM DTT, and heated at 100° C. for 3 minutes. Since only about half of the phosphotyrosyl protein content of the original liver extract was removed by a single pass over the aPY-Ab column under the conditions just described, the liver extract was therefore recycled through the column, and the adsorption, column washing, hapten elution, dialysis and concentration procedure was repeated, and the final sample combined with the first, and stored at −70° C.

Dry liver protein precipitate was prepared as follows. Male rats (100 to 250 g) were fed ad libitum with Purina Laboratory Rodent Chow, except where indicated. Rats were injected with sodium amobarbital (150 mg/kg body weight, intraperitoneal) and were used in experiments 10 to 15 minutes later as soon as anesthesia was assured by loss of pedal and corneal reflexes. The abdominal cavity was opened, the portal vein or inferior vena cava exposed, and normal saline (0.9% NaCl) with or without hormone ($10^{-6}$M insulin) was infused through a 27 g needle connected to a mechanical syringe pump driven at 1 cc/min for 0.5 minutes.

Following infusion, the liver or other tissues were rapidly excised, coarsely minced and immediately disrupted for 45 seconds in 35 cc of solubilization buffer maintained at 100° C. in a water bath with a Polytron PTA 20S generator (Brinkmann Inst. Co., Model PT10/35) operated at maximum speed (Setting 10). The solubilization buffer was composed of 2% SDS, 100 mM HEPES (pH 7.8 at 22° C.), 100 mM NaCl, 10 mM EDTA and 50 mM DTT. The homogenate was further heated to boiling with gentle stirring for 2 minutes, and then left to cool to 22° C. After centrifugation at 35,000 rpm for 2 hours at 18° C. in a Beckman Type 35 rotor (143,000×g at $r^{max}$), the supernatant was acidified with 100% TCA, added slowly dropwise at 22° C. with vigorous stirring, to a final TCA concentration of 10%. The mixture was then cooled on ice for 30 minutes. Under these conditions protein and nucleic acids form a copious, flocculent, pink precipitate while SDS remains largely soluble. Preliminary tests indicated that TCA concentrations of 5 and 15% gave identical results. The precipitate was collected by centrifugation at 5,000 rpm in a Sorvall SS-34 rotor at 4° C. for 5 minutes. The precipitate was washed once with 25 volumes of 10% TCA at 4° C., and the TCA was then extracted by three washes, each with 25 volumes of ethanol:diethyl ether (1:1, v/v) at 4° C. The precipitate was dried in vacuo for 4 to 18 hours. The final yield of dry precipitate was about 0.05 gram per gram of liver (wet wt.). The precipitate was thoroughly pulverized to a fine powder in a porcelain mortar. In this form the extracted proteins can be stored for at least 1 year at −70° C. without apparent degradation or significant loss of phosphotyrosine content.

Alternate methods of removing the SDS from the initial tissue extracts were evaluated. These include: precipitation of the insoluble potassium salt of SDS by KCl addition (Suzuki et al., 1988, Anal. Biochem. 172:259–263, hereby incorporated by reference, Zaman et al., 1979, Anal. Biochem. 100:64–69, hereby incorporated by reference), dilution of the SDS with an excess of Triton X-100 (Clarke, 1981, Biochem. Biophys. Acta 670:195–202, hereby incorporated by reference), selective precipitation of proteins with cold organic solvents (Hager et al., 1980, 109:76–86, hereby incorporated by reference), and ion-pair extraction of the SDS with triethylamine (Konigsberg et al., 1983, Methods Enzymol. 91:254–259, hereby incorporated by reference). These treatments were unsatisfactory because of much lower yields of phosphotyrosyl proteins and/or formation of intractable protein precipitates which could not be redissolved. Use of different lots of SDS obtained from different manufacturers altered the recovery of phosphotyrosyl proteins, perhaps due to variable contamination with hexadecyl sulfates which have higher protein binding affinity and are less readily removed (Lacks et al., 1979, Anal. Biochem. 100:257–363, hereby incorporated by reference).

For the immunoprecipitation of phosphotyrosyl proteins, 0.1 gram of dry tissue powder was dissolved in 0.1N NaOH (0.05 g powder/ml) with vigorous stirring at 22° C. for 3 minutes. The resulting solution was then rapidly neutralized to pH 8 with 2 volumes of 100 mM Tris-HCl. EDTA (1 mM), $NaN_3$ (0.1%) and the protease inhibitors PMSF (1 mM), leupeptin (1 ug/ml), aprotinin (1 ug/ml) were added, and the slightly turbid solution clarified with a 0.45 um pore diameter cellulose/PVC filter (Millex-HA, Millipore Corp.). Control experiments demonstrated that once resolubilized, the phosphotyrosine content of the extracted proteins was stable for at least 3 days at 4° C. In later experiments omission of the protease inhibitors was without effect. Protein concentrations were determined with the Bradford dye binding assay (Bradford, 1976, Anal. Biochem. 72:248–254, hereby incorporated by reference) using dye reagent and immunoglobulin protein standards from BioRad, or alternatively by optical density as described by Whitaker and Granum (Whitaker et al., 1980, Anal. Biochem. 109:156–159, hereby incorporated by reference). Anti-phosphotyrosine antibodies were added to a final concentration of 3–4 ug IgG/ml and incubated at 4° C. with gentle agitation. The immunocomplexes were washed twice by resuspension and brief centrifugation in 1 ml of wash buffer (1% Triton X-100, 0.1% SDS, 100 mM NaCl, 50 mM Tris, pH 7.3 at 22° C) and once further in the same buffer lacking NaCl. After aspirating excess wash buffer, the immunoprecipitated proteins were solubilized in 50 ul of SDS-PAGE sample buffer (Laemmli) with 50 mM DTT at 100° C. for 3 minutes. For some experiments, the immunoprecipitated phosphotyrosyl proteins were competitively eluted from the antibody-bead pellet by incubating with 100mM pNPP, 50 mM Tris, pH 7.4, 0.05% SDS for 1 hour at 22° C. The eluate was desalted by centrifugal passage (Helmerhorst et al., 1980, Analytical Biochemistry 104:130–135, hereby incorporated by reference) over a micro-column of G-25 Sephadex, pre-equilibrated with Laemmli sample buffer.

The anti-phosphotyrosine antibody affinity-matrix was prepared as follows. 38 milligrams of affinity-purified rabbit anti-phosphotyrosine antibody (aPY Ab) was adsorbed to 12 mls (settled gel volume) of Protein A TrisAcryl, by slow mixing at 4° C. overnight in 150 mM NaCl, 50 mM HEPES, pH 7.8. The gel matrix was washed three times with 100 mls of 0.2M sodium borate, pH 9.0 at 22° C. and resuspended in 45 mls of 0.2M sodium borate, pH 9.0 also containing 2 mM pNPP (to bind and protect the antibody combining site) for 2 hours at 22° C. Dimethylpimelimidate was then added (20 mM final concentration), and the matrix gently mixed at 22° C. for 30 minutes to covalently link the antibody to Protein A (Simanis et al., 1985, Virology 144:88–100, hereby incorporated by reference). The antibody-matrix was then washed with excess 0.2M ethylamine, pH 8.0 at 22° C. and incubated 2 hours further in the same buffer to quench unreacted dimethylpimelimidate. The cross-linked matrix was washed extensively and stored at 4° C. in 10 mM Tris, pH 7.5, 150 mM NaCl, 0.02% NaN$_3$. Use of a tris-acryl matrix for this affinity column was essential, as the relatively hydrophilic nature of this material (Dean et al., Affinity Chromatography, IRL Press, Washington, D.C. pp. 11–14, 1985, hereby incorporated by reference) minimized non-specific adsorption of denatured proteins.

To estimate the yield of purified phosphotyrosyl proteins, the samples were resolved on 5% SDS-PAGE, 0.5 mm thick gels, then electrotransferred to PVDF membranes at 95 volts for 2 hours at 35° C. in 10 mM CAPS, pH 11.0, 10% methanol, as described by Matsudaira (Matsudaira, 1987, J. Biol. Chem. 262:10035–10040, hereby incorporated by reference). The PVDF membranes were incubated in 0.1% Coomassie Blue R-250, 50% methanol, for 5 minutes, and following destaining (in 50% methanol, 10% acetic acid), the visible protein bands were individually excised. Proteins blotted onto PVDF membranes were placed in 6×50 mm tubes previously baked at 1000° F. for 16 hours. The tube(s) were placed in a Waters hydrolysis vial., 200 ul of constant boiling HCl added, and the vial evacuated and flushed with argon. After a final exposure to vacuum, the vial was sealed and heated at 110° C. for 22 hrs. Following hydrolysis, the samples were dried in vacuo, and the resultant amino acids analyzed as follows. The PVDF membrane was wet with 10 ul MeOH, then extracted twice with 100 ul of 0.1M HCl/20% MeOH. This extract was taken to dryness, dissolved in 4 mM EDTA, and loaded onto an Applied Biosystems 420A derivatizer/analyzer for amino acid analysis. Phosphotyrosyl protein yields were also estimated by direct silver staining of SDS-PAGE gels (Heukeshoeven et al., 1985, Electrophoresis 6:103–112, hereby incorporated by reference), or alternatively by colloidal-gold staining of nitrocellulose electroblots (Li et al., 1989, Analytical Biochemistry 182:44–47, hereby incorporated by reference), (Hunter et al., 1987, Analytical Biochemistry 164:430–433, hereby incorporated by reference) with comparison of band intensities to those of standard reference proteins included in the same gel or blot.

Electrophoresis and immunoblotting were performed as follows. Immunoprecipitated proteins were separated on 0.5 mm thick, 1-D SDS-PAGE (5% T acrylamide) using the formulations of Laemmli (Laemmli, 1970, Nature 227:680–685, hereby incorporated by reference) in a Bio-Rad miniature slab gel apparatus (Mini-Protean) at 175 V (constant). Standard molecular weight protein markers were: myosin (200 kDa), β-galactosidase (116 kDa), phosphorylase b (97.4 kDa) BSA (66.2 kDa) and ovalbumin (42.7 kDa). Electrotransfer of proteins from the gel to nitrocellulose was performed for 2 hours at 100 V (constant) at 5–15° C. in the BioRad miniature transfer apparatus (Mini-Protean), as described by Towbin (Towbin et al., 1979, Proc. Natl. Acad. Sci. USA 76:4350–4354, hereby incorporated by reference), but with 0.05% SDS added to the transfer buffer to enhance elution of high molecular weight proteins. Preliminary experiments using alternate transfer buffers (Szewczyk et al., 1985, Anal. Biochem. 150:403–407, hereby incorporated by reference) or transfer times varying from 0.5 to 4 hours gave qualitatively identical results. Non-specific protein binding to the nitrocellulose was reduced by preincubating the filter overnight at 4° C. in blocking buffer (5% BSA, 1% ovalbumin in TNA [10 mM Tris, pH 7.2, 0.9% NaCl, 0.02% NaN$_3$]). The nitrocellulose blot was incubated with anti-phosphotyrosine antibodies diluted in blocking buffer (2 ug/ml) for 2 hours at 22° C. and then washed twice for 10 min in TNA, once for 10 minutes in TNA containing 0.05% NP-40, and twice further for 10 minutes each in TNA. The blots were then incubated with 50 uCi of $^{125}$I-Protein A (6–30 uCi/ug) in 10 mls of blocking buffer for 1 hour at 22° C. and then again washed as described above. Bound anti-phosphotyrosine antibodies were detected by autoradiography using pre-flashed (Laskey et al., 1975, Eur. J. Biochem. 56:335–342, hereby incorporated by reference) Kodak XAR film with Cronex Lightning Plus intensifying screens at −70° C. for 12 to 72 hours. Band intensities were quantitated by optical densitometry (Hoefer Instruments Model GS300) of the developed autoradiogram or by direct gamma scintillation spectrometry of bands excised from the nitrocellulose blots.

PMSF, leupeptin, aprotinin, p-nitrophenyl-phosphate, ovalbumin, DTT, dimethylpimelimidate and NP-40 were purchased from Sigma. Sodium amobarbital (Amytal) and porcine insulin and human recombinant insulin (Humulin R) were from Eli Lilly Co. BSA (Fraction V) was from Armour. SDS (protein chemistry special grade), Tris-HCl and HEPES (ultrapure grade) were from Boehringer Mannheim. $^{125}$I-Protein A was from ICN. Immobilized Protein A beads (Trisacryl) and Triton X-100 (purified grade) were obtained from Pierce. TCA and diethyl ether (anhydrous) were from Fisher Scientific. Wheat germ agglutinin-agarose was from Vector Labs. Male Sprague-Dawley rats were from Charles River, Wilmington, Mass. Nitrocellulose (BA85, 0.2 um) was from Schleicher and Schuell. PVDF membranes were from Millipore. Reagents for SDS-PAGE, including molecular weight standards were from BioRad. Silver-stain reagent kit was from Sigma, and colloidal gold-stain from Janssen. Sequencing grade bovine trypsin was obtained from Boehringer Mannheim. HPLC grade trifluoroacetic acid was obtained from Applied Biosystems, Inc.; HPLC grade acetonitrile and water from Burdick and Jackson; and Vydac HPLC columns from The Nest Group. Automated sequencer and analyzer reagents were provided by the manufacturer. All other reagents were of at least analytical grade purity. Polyclonal anti-phosphotyrosine antibodies were raised in rabbits and affinity-purified on phosphotyramine columns as described by Pang et al., 1985, Arch. Biochem. Biophys. 242:176–186, hereby incorporated by reference).

Validation of methods

Phosphotyrosyl proteins are susceptible to rapid phosphatase-mediated dephosphorylation both in vivo (Lau et al., 1989, Biochem J. 257:23–36, hereby incorporated by reference) and during cell extraction procedures (Kamps et al., 1988 Oncogene 2:305–315, hereby incorporated by reference). To assay hormone-stimulated tyrosine, phosphorylation in intact organs of the live animal under conditions which block dephosphorylation, tissues were rapidly homogenized at 100 ° C. in 2% SDS solution also containing 50 mM DTT reductant. These conditions denature all cell proteins, eliminating enzymatic dephosphorylation and proteolysis of phosphotyrosyl proteins. However, attempts at analysis of such SDS extracts from animal tissues by direct, conventional anti-phosphotyrosine antibody immunoblotting yielded only poorly resolved bands of very low intensity. To selectively concentrate cellular phosphotyrosyl proteins by anti-phosphotyrosine antibody immunoprecipitation, the SDS denaturant was first removed by precipitation of proteins with TCA'- under conditions where SDS remains soluble (Weber et al., in The Proteins, Vol. I, Chapter 3, Neurath and Hill, eds. Academic Press, 1975, pp. 179–223, hereby incorporated by reference). TCA was removed by organic extraction, the protein precipitate redissolved in 0.1N NaOH (conditions where phosphotyrosine is stable, (Cooper et al., 1983, Methods Enzymol. 99:387–402, hereby incorporated by reference), and following neutralization, the phosphotyrosyl proteins were quantitatively precipitated with anti-phosphotyrosine antibodies. The immunoprecipitated proteins were then resolved by 1-D SDS-PAGE, electroblotted to nitrocellulose, and detected with additional anti-phosphotyrosine antibody and $^{125}$I-Protein A.

The validity of this method was tested by examining the insulin response of FaO hepatoma—a cell line (Deschartrette et al., 1979, Somatic Cell Gen. 5:697–718, hereby incorporated by reference) with well characterized insulin receptor tyrosine autophosphorylation and endogenous protein phosphorylation (Crettaz et al., 1984, Diabetes 33:477–485; White, et al., 1987, J. Biol. Chem. 262:9769–9777, hereby incorporated by reference). Experiments were performed to compare the recovery of phosphotyrosyl proteins from control and insulin stimulated FaO cells using either the boiling SDS denaturation/TCA precipitation method or using the generally employed, nondenaturing detergent (Triton X-100) extraction method at 0° C. with phosphatase inhibitors (10 mM $Na_4P_2O_7$, 100 mM NaF, 2mM $Na_2VO_4$, 10 mM EDTA) (White et al., 1987, J. Biol. Chem. 262:9769–9777, hereby incorporated by reference). Under non-denaturing extraction conditions, in the absence of insulin, FaO cells contain a major phosphotyrosyl protein at $M_r=120$ kDa. Upon insulin stimulation ($10^{-6}$M) for 1 minute, only one new phosphotyrosyl protein appears at $M_r=95$ kDa, consistent with the autophosphorylated β-subunit of the insulin receptor. Use of denaturing SDS extraction demonstrates the same $M_r=120$ kDa phosphotyrosyl protein and upon insulin stimulation the appearance of receptor β-subunit phosphorylation. In addition, SDS extraction permits detection of a distinct, insulin stimulated phosphotyrosyl protein at $M_r=185$ kDa. This band has been previously designated pp185 (White et al., 1987, J. Biol. Chem. 262:9769–9777, hereby incorporated by reference; White et al., 1985, Nature 318:183–186, hereby incorporated by reference; Izumi et al., 1987, J. Biol. Chem. 262:1282–1287, hereby incorporated by reference; Beguinot et al., 1988, Biochemistry 27:3222–3228, hereby incorporated by reference; Kadowaki et al., 1987, J. Biol. Chem. 262:7342–7350, hereby incorporated by reference; Condorelli et al., 1989, J. Biol. Chem. 264:12633–12638, hereby incorporated by reference), and is likely an endogenous, cellular substrate of the insulin receptor tyrosine kinase (Tashiro-Hashimoto et al., 1989, J. Biol. Chem. 264:6879–6885, hereby incorporated by reference). The attenuated band intensities and the apparent lack of pp185 in the Triton X-100 extracts compared to the SDS extracts is attributed to incomplete inhibition of phosphotyrosyl phosphatase activity under non-denaturing conditions-despite inclusion of phosphatase inhibitors. When non-denaturing Triton X-100 buffers were used to solubilize animal tissues in preliminary experiments, virtually no phosphotyrosyl proteins could be observed. In contrast, the SDS denaturation/TCA precipitation technique makes possible analysis of insulin receptor tyrosine kinase activity in organs and tissues of the intact animal under physiological conditions, as described herein.

FaO hepatoma cells (Deschatrette et al., 1979, Somatic Cell Gen. 5:697–718, hereby incorporated by reference) were cultured in Falcon 150 mm diameter plasticware dishes in Dulbeccos Modified Essential Medium supplemented with 10% heat-inactivated fetal calf serum (Gibco) and penicillin/streptomycin (Crettaz et al., 1984, Diabetes 33:477–485, hereby incorporated by reference) at 37° C. in a 5% $CO_2$ incubator. For experiments, 90% confluent cultures ($10^7$ cells) were serum deprived for 16–18 hours prior to hormone stimulation, extraction and analysis. In some experiments, cultures were metabolically labelled with 1 mCi of $^{32}$P-orthophosphate in $P_1$-free medium for 4 hours prior to analysis by methods described elsewhere (White et al., 1987, J. Biol. Chem. 262:9769–9777, hereby incorporated by reference). Solutions containing sodium orthovanadate were prepared at neutral pH to avoid loss of phosphatase inhibitory activity, as previously described (Kadota et al., 1987, J. Biol. Chem. 2628252–8256, hereby incorporated by reference).

Proteolytic digestion and sequencing of pp185

Because soluble proteins often have blocked N-termini which prevent Edman degradation (Brown et al., 1976, J. Biol. Chem. 251:1009–1115; Moos et al., 1988, J. Biol. Chem. 263:6005–6008, hereby incorporated by reference) and since pp185 was contaminated by an unknown protein of the same $M_r$, the amino acid sequencing strategy depended on analysis of both basal and insulin-stimulated bands. The $M_r=185$ kDa proteins eluted from the anti-phosphotyrosine affinity column were separated by 1D-SDS PAGE, transferred to nitrocellulose, and then digested with trypsin in situ. The resulting tryptic polypeptide fragments were then resolved on a reverse phase C18 HPLC column, and the basal and insulin-stimulated tryptic peptides compared.

Close comparison of the two peptide maps revealed 8 distinct peaks which were present only in the insulin-treated sample (Peaks 42, 43, 58, 72, 73, 76, 80, and 98) and these were provisionally assigned to pp185. These peak fractions were subjected to direct amino acid sequence analysis in an automated sequenator. In addition, three peaks common to both the control and the insulin-treated maps were sequenced. The amino acid sequence data for all peptides is summarized in Table I.

from the control sample. CPS was also present in the secondary and tertiary sequences of Peaks 80, and 76, respectively, and also as the primary sequence in Peak 98. Control experiments with anti-CPS antiserum confirmed that CPS is not tyrosine phosphorylated in liver following insulin stimulation.

TABLE I

SUMMARY OF SEQUENCE DATA FOR pp185 POLYPEPTIDES
Tryptic peptides were subjected to amino terminal protein sequence analysis as described above. Designations for tryptic fragments correspond to the column peaks described above. Where multiple sequences were identified in a given peak fraction the sequences are designated primary (1•), then secondary (2•), etc., in order of decreasing molar yield. The number in parenthesis after a sequence indicates the position of that sequence in IRS-1.

| Fragment | Sequence | Identity |
| --- | --- | --- |
| From + Insulin Sample | | |
| 42 | 1• LEYYENEK(44) (SEQ ID NO: 5) | IRS-1 |
| 43a | 1• EQQQQQQQQQqqSiLXPpE(871) (SEQ ID NO: 6) | IRS-1 |
| 43b | 2• LSSETFSAPXp(1098) (SEQ ID NO: 7) | IRS-1 |
| 58 | 1• VVAVDXGIK (SEQ ID NO: 8) | CPS @ 220 |
| 72$^1$a | 1• EETGStXYMNMDLGPGea(932) (SEQ ID NO: 9) | IRS-1 |
| 72b | 2• XLPDAemgXspaXT(484) (SEQ ID NO: 10) | IRS-1 |
| 76$^2$a | 1• SVSAPQQIINPI(635) (SEQ ID NO: 11) | IRS-1 |
| 76b | 2• NLIGIY(173 ) (SEQ ID NO: 12) | |
| | 3• GQXLTMAN (SEQ ID NO: 13) | CPS @ 91 |
| 80 | 1• YIPGATMGTSPALTGDEAr(489) (SEQ ID NO: 14) | IRS-1 |
| | 2• SFAFvS (SEQ ID NO: 15) | CPS @ 1263 |
| 98 | 1• XISHAISEHVEDSGVHS (SEQ ID NO: 16) | CPS @ 1187 |
| 98b | 2• XLGASPpNAXTAPXXXr (SEQ ID NO: 17) | IRS-1 |
| 98c | 3• XPPXTFQXVXXP (SEQ ID NO: 18) | IRS-1 |
| 138$^3$ | 1• SAVTGPGEFWMQVDDSVVAQNmXe(223) (SEQ ID NO: 19) | None |
| | 2• QADAVYFLPITPQFVTEVIX (SEQ ID NO: 20) | CPS @ 478 |
| From − Insulin Sample | | |
| 53 | 1• TFEESFQk (SEQ ID NO: 21) | CPS |
| 115 | 1• LFATEATSDW (SEQ ID NO: 22) | CPS @ 1388 |
| | 2• TADdSXIXIl (SEQ ID NO: 23) | CPS @ 1455 |

Notes:
[1]Residues clearly observed at positions 6 and 7 could not be assigned unambiguously to the major vs. minor sequence, as they were of equal yield.
[2]Relative molar yield of PTH-derivatives for 1•:2•:3• sequences approximately 2:2:1. Therefore, residues clearly observed at positions 1 through 5 of the 1• and 2• sequences could not be assigned unambiguously to the major versus minor sequence, as they were of equal yield.
[3]Equimolar abundance of 1• and 2• sequences. Deduced CPS tryptic peptide @ 478 listed as 2•.
Residues in lower case letters represent assignments of less than full confidence. Positions where no assignment was possible are indicated by X. A = alanine; R = arginine; N = asparagine; D = aspartic acid; C = cysteine; Q = glutamine; E = glutamic acid; G = glycine; I = isoleucine; L = leucine; K = lysine; M = methionine; F = phenylalanine; P = proline; S = serine; T = threonine; Y = tyrosine; and V = valine.

Peak 42 yielded a single, 8 residue sequence. Searching of gene and protein sequence registries reveals this sequence is not identical to any previously reported sequence. Peak 43 yielded an interesting sequence of 18 residues, beginning with Glu, followed by 10 consecutive Gln residues. Peak 43 also contained a secondary (less abundant) sequence of 11 residues. Neither the primary nor the secondary sequence of Peak 43 is identical with reported sequences. Novel sequences were also derived from Peaks 72, 76, 80, 98, and 138. Although Peak 58 appeared in the tryptic map of the insulin-treated sample, the sequence of this peak matched that of an internal tryptic fragment of carbamyl phosphate synthetase (CPS) (Nyunoya et al., 1985, J. Biol. Chem. 260:9346–9356, hereby incorporated by reference). CPS is an inner mitochondrial matrix protein which is abundant in fasted rat liver (Schimke, 1963, J. Biol. Chem. 237:1921–1924, hereby incorporated by reference). This result suggested that CPS was the protein which nonspecifically co-purified with pp185. Additional sequence data supporting this identification of CPS as the contaminant was provided by the sequencing of Peak 53, and Peak 115

As evidenced by these results, any individual tryptic peak is not necessarily homogenous and may contain more than a single polypeptide species. To assess possible peak heterogeneity, the ultraviolet absorbance of each peak was monitored with a diode array detector, allowing simultaneous detection at 210 nm, 277 nm and 292 nm. Absorbance at 210 nm and 277 nm monitors for peptide bonds and aromatic residues, respectively, while detection at 292.nm distinguishes peptides containing tyrosine from those containing tryptophan. Tyrosine containing peptides have a low 292/277 nm absorbance ratio, whereas tryptophanyl peptides have a high 292/277 nm ratio. One tryptic peak, 138, was present in the peptide maps of both control and insulin-treated material, absorbing at 210 nm and 277 nm. However, this peak lacked absorbance at 292 nm in the control map but did absorb significantly at 292 nm in the insulin-treated map. Automated Edman degradation of peak 138 (from the insulin-treated map) resulted in identification of two different residues at each of the first 19 sequenator cycles. These residues were of equal yield, thus precluding direct assignment of residues to a primary or secondary sequence.

However, analysis of the predicted tryptic cleavage products of CPS revealed one CPS peptide sequence (at CPS residue 478) which uniquely matched one of each pair of residues present in the first 19 sequencer cycles of peak 138. Therefore, it was possible to subtractively deduce the second, novel peptide sequence (which contained the predicted tryptophan) from the data obtained from peak 138, and assign this sequence to pp185.

Enzymatic cleavage of pp185 was performed as follows. Anti-phosphotyrosine affinity-purified liver proteins, concentrated by vacuum-dialysis into a solution containing 3% SDS, 50 mM Tris pH 7.2, 50 mM DTT, 10% sucrose, were made 5% in SDS, then preparatively separated by reducing 1-D SDS-PAGE (5.5% T -0.8% C°) in a BioRad miniature slab gel apparatus, using 1.2 mm thick gels, run at 150 Vosts, with electrophoresis buffers as described by Laemmli (Laemmli, 1970, Nature 227680–685, hereby incorporated by reference). After electrophoresis, the proteins were electro-transferred to BA 85 nitrocellulose in transfer buffer (10 mM Tris, pH 8.0, 192 mM glycine, 20% methanol, 0.02% SDS) for 2 hours at 4° C., and then for an additional 15 minutes in transfer buffer lacking SDS. To locate the protein bands, the nitrocellulose was stained for 2 minutes in 0.1% Ponceau S, 1% acetic acid, and destained for 4 minutes in 1% acetic acid. The lightly stained bands were excised with a scalpel, washed three times with HPLC-grade water, and stored moist at −20° C.

Peptide fragments of the electrophoretically separated proteins were generated by in situ proteolytic digestion of the nitrocellulose-bound proteins with trypsin, as described by Aebersold (Aebersold et al., 1987, Proc. Natl. Acad. Sci. USA 84:6970–6974, hereby incorporated by reference), but omitting the NaOH wash to minimize the loss of protein. After digestion the solution was immediately stored at −20° C. until separation of the resultant peptides by narrow-bore reverse phase HPLC.

Reverse phase HPLC separation of peptides was performed as follows. Peptides were separated by narrow-bore reverse phase HPLC on a Hewlett-Packard 1090 HPLC equipped with a 1040 diode array detector, using a Vydac 2.1 mm×150 mm C18 column. The gradient employed was a modification of that described by Stone et al. (Stone et al., 1989 Techniques in Proteins Chemistry, Hugli ed., pp. 377–391 Academic Press). Briefly, where buffer A was 0.06% trifluoroacetic acid/$H_2O$ and buffer B was 0.055% trifluoracetic acid/acetonitrile, a gradient of 5% B at 0 min, 33% B at 63 min, 60% B at 95 min and 80% B at 105 min with a flow rate of 0.15 ml/min was used. Chromatographic data at 210, 277 nm and ultraviolet spectra from 209 to 321 nm of each peak were obtained. While monitoring absorbance at 210 nm, fractions were manually collected by peak into microfuge tubes and immediately stored without drying at −20° C. in preparation for sequence analysis.

Amino terminal peptide sequence analysis was performed as follows. Samples for amino terminal sequence analysis were applied directly to a polybrene pre-cycled glass fiber filter and placed in the reaction cartridge of an ABI Model 477A protein sequencer. The samples were subjected to automated Edman degradation using the program NORMAL-1, which was modified using the manufacturer's recommendations for faster cycle time (36 min) by decreasing dry-down times and increasing reaction cartridge temperature to 53° C. during coupling. The resultant phenylthiohydantoin amino acid fractions were subsequently identified using an on-line ABI Model 120A HPLC and Shimadzu CR4A integrator. Computerized protein and gene sequence database searches were performed using the Intelligenetics FASTDB program. Anti-peptide antibody studies If the novel peptide sequences we assigned to pp185 are contained within the primary structure of this insulin receptor substrate, then antibodies to these peptides should recognize a protein with properties expected of pp185. To test this prediction, polyclonal antibodies to a synthetic peptide containing the first 15 residues of the primary sequence of Peak 80 (Table I) were raised. Anti-peptide 80 antibodies clearly reacted on immunoblots with a single $M_r$=185 kDa band which had first been immunoprecipitated with anti-phosphotyrosine antibodies from extracts of insulin-stimulated liver. Anti-peptide 80 antibodies do not recognize such a band in the anti-phosphotyrosine immunoprecipitate obtained from control (no insulin treatment) liver extracts. This result is consistent with the presence of phosphotyrosine in pp185 only after the insulin receptor tyrosine kinase has been activated. Anti-peptide 80 antibodies also immunoprecipitate from both control and insulin-stimulated liver extracts a single 185 kDa protein which is recognized equally well on immunoblots by anti-peptide 80 antibodies, but which is reactive with anti-phosphotyrosine antibodies only when precipitated from insulin-stimulated livers. Additional control experiments demonstrated that anti-peptide 80 antibody immunoprecipitation of the $M_r$=185 kDa protein was completely blocked when 1 uM synthetic peptide 80 was added to the original liver extract. These results strongly support the derivation of the novel peptide sequences of Table I from authentic pp185.

Anti-pp185 antibodies were prepared as follows. Polyclonal antibodies to peptide segments of pp185 were raised in young adult New Zealand White rabbits. Synthetic peptides were prepared by solid phase peptide synthesis and purified by reverse-phase high pressure liquid chromatography. Peptides were coupled to RSA carrier by the bisdiazobenzidine method (Gordon et al., 1958, J. Exptl. Med. 108:37–51, hereby incorporated by reference) and by glutaraldehyde (Reichlin, 1980, Methods Enzymol. 70:159–165, hereby incorporated by reference), and a mixture of these conjugates used to immunize three rabbits. Immunoglobulin fractions of the sera were prepared by ammonium sulfate precipitation and DEAE-Sephacel chromatography (Harlow et al., 1988, Antibodies, Lab Manual, pp. 302–305, Cold Spring Harbor Laboratory Press, hereby incorporated by reference). Antibodies were further affinity-purified on a column prepared by coupling synthetic peptide to Affigel 10 (according to the manufacturers directions), with antibody elution using 100 mM glycine, pH 2.5 and rapid neutralization. To assess anti-peptide immunoreactivity with nondenatured pp185, whole rat liver cytosolic extracts were prepared by homogenizing 1 gram of liver in 25 cc of homogenization buffer (0.25M sucrose, 5mM EDTA, 5 mM EGTA, 10 mM $Na_4P_2O_7$, 20 mM NaF, 50 mM HEPES, pH 7.5, 1 mM PMSF, 5 ug/ml leupeptin, 5 ug/ml aprotinin, 1 mg/ml bacitracin, 0.1 mg/ml benzamidine) at 0° C., and clarified by centrifugation at 100,000×g for 1 hr.

Insulin Metabolism and pp185

Hepatic insulin response

To determine the rate of insulin receptor autophosphorylation and its relationship to tyrosine phosphorylation of cellular proteins in vivo, insulin ($10^5$M) was infused into the portal vein of anesthetized rats. In the absence of insulin only one major, phosphotyrosyl protein ($M_r$=120 kDa) is present. At the earliest time point sampled after initiating insulin infusion the insulin receptor β-subunit appeared at $M_r$=95 kDa and was already maximally autophosphorylated. Similarly, at t=0.5 min the endogenous substrate of the insulin receptor (pp185) was also maximally tyrosine phosphorylated. Despite continuous insulin infusion, the level of insulin receptor β-subunit tyrosine phosphorylation slowly decreased, with a t½=6 minutes (determined by densitometry of autoradiographs from 3 replicate experiments). Under these same conditions, pp185 was even more rapidly dephosphorylated, and reduced to nearly baseline intensity after only 2–3 minutes. No additional insulin-stimulated phosphotyrosyl proteins were detected in liver over this time period, even when gel electrophoresis conditions were adjusted to resolve low $M_r$ proteins (%T acrylamide= 10–15%), or when autoradiographs were over exposed, or when the insulin-stimulated liver was initially quick frozen and powdered in liquid $N_2$ prior to further processing, or when two alternate preparations of anti-phosphotyrosine antibodies were used. Essentially identical patterns of tyrosine phosphorylation of the $M_r$=185 kDa and 95 kDa bands were observed in hindlimb skeletal muscle and epididymal fat pads, following acute insulin infusion into the inferior vena cava. However, in rat fat pads, an additional, insulin-sensitive phosphotyrosyl protein of $M_r$=60 kDa is also readily detected. No consistent, insulin-related change in the tyrosine phosphorylation of the $M_r$=120 kDa band has been observed.

The in vivo insulin sensitivity of hepatic insulin receptor kinase activation and substrate phosphorylation was examined by varying the concentration of insulin infused into the portal vein from $10^{-12}$ to $10^{-6}$M. With increasing insulin, the intensity of insulin receptor β-subunit and pp185 tyrosine phosphorylation increased in parallel, although the pp185 band was 30% as intense as the β-subunit band. Half-maximal phosphorylation occurred at $1-5\times10^{-8}$M insulin. Based on dilution of the infusate by portal blood flow (portal flow in 200 g, anesthetized rat: 8.9 cc/min, (Vidt et al., 1959, Circ. Res. 7:759–768, hereby incorporated by reference); insulin infused at 0.2 cc/min.) the effective insulin concentration within the hepatic sinusoids and at the cell surface is at least 45-fold lower than the infused concentration. Thus, the insulin sensitivity is in good agreement with the reported binding constant of the hepatic insulin receptor (Kahn et al., 1974, J. Biol. Chem. 240:2249–2257, hereby incorporated by reference). The observed results are not dependent on the anti-phosphotyrosine antibody immunoprecipitation/ immunoblotting assay, as control experiments demonstrated the linearity of the method over the range of antibody concentrations used.

Regulation of insulin-stimulated tyrosine phosphorylation in vivo

To investigate whether physiological states which modulate tissue insulin sensitivity might be associated with altered patterns of in vivo protein tyrosine phosphorylation experiments were performed with rats subjected to prolonged fasting, streptozotocin-diabetes, and hypophysectomy. Fasting diminishes pancreatic insulin secretion and also includes peripheral tissue insulin resistance (DeFronzo et al., 1978, J. Clin. Invest. 62:204–212, hereby incorporated by reference; Cech et al., 1980, Biochem. J. 188:839–845, hereby incorporated by reference). In these experiments male Sprague-Dawley rats, initial body weight 200–250 grams, were deprived of food for 1, 2, or 3 consecutive days, anesthetized, and saline without or with $10^{-6}$M insulin was infused into the portal vein at 1 cc/min for 0.5 min. The entire liver of each animal was excised and processed for anti-PY antibody immunoprecipitation and immunoblotting as described in above. Results are representative of three replicate experiments. Control animals infused with saline alone contain only the Mr=120 kDa phosphotyrosyl band and that this band did not change with prolong fasting nor was it influenced by acute insulin infusion. After a 1 day fast, insulin did promote tyrosine phosphorylation of the insulin receptor β-subunit (Mr=95 kDa) and pp185 with a pattern similar to that in fed animals. Over the next two days of fasting the β-subunit band increased slightly compared to the 1 day fasting condition (26%, mean of 3 experiments). However, a much greater increase occurs over this same period in the pp185 band with a 100% increase after only 2 days and a 146% increase after 3 days fasting, relative to day 1. At day 3, the intensity of the pp185 band is nearly equal to the β-subunit band intensity. Whether this relative increase in the pp185 band results from induced expression of the pp185 protein or whether it is related to increase phosphorylation (or decreased dephosphorylation) of a constant level of pp185 remains to be determined.

Another condition of insulin deficiency and hepatic insulin resistance occurs in diabetes induced by the islet cell toxin streptoxotocin (Dall'aglio et al., 1985, Amer. J. Physiol. 249:E312–316, hereby incorporated by reference). Adult Sprague-Dawley rats were injected with streptoxotocin (55 mg/kg b.w.) or vehicle alone and the development of diabetes monitored by assay of blood and urine glucose levels. In these experiments male Sprague-Dawley rats were injected on Day 0 via tail vein with saline-citrate buffer, pH 4.5 without (control) or with streptozotocin (STZ-diabetic), at 55 mg STZ/kg body weight. On Day 3 when the diabetic condition was confirmed by blood glucose levels greater than 300 mg/dl, some diabetic animals (Ins Tx'd STZ) received once daily subcutaneous insulin injections (6 units Humulin R) and the experiment shown above performed on Day 10. Blood glucose was 116±20 mg/dl (mean±S.D.; n=10) in control rats, 377±51 mg/dl (n=10) in STZ-diabetic rats, and 70±54 mg/dl (n=6) in insulin-treated diabetic rats. Body weights at sacrifice were 304±19 g (mean±S.D.) in control rats, 250±7 g in diabetic rats, and 314±7 g in insulin-treated diabetic rats. Anesthetized animals received intraportal infusion of saline without (−) or with $10^{-6}$M insulin (+) for 0.5 min and the entire liver excised and processed for anti-PY immunoprecipitation and immunoblotting as described in above.

In the euglycemic control rats the hepatic response is essentially the same as previously described, without and with acute insulin stimulation. In the streptozotocin-treated, diabetic animals, the activated insulin receptor β-subunit underwent tyrosine autophosphorylation to an extent only 33% (mean, n=3) greater than control rats, while pp185 tyrosine phosphorylation increased by 142% (mean, n=3) relative to control rats. When the diabetic rats were treated with daily subcutaneous insulin injections to normalize their blood glucose levels, the intensity of insulin receptor β-subunit and pp185 tyrosine phosphorylation also normalized.

Another state of relative insulin deficiency and impaired glucose tolerance is induced in the rat by hypophysectomy (Penhos et al., 1971, Endocrinology 88:1141–1149, hereby incorporated by reference). Following hypophysectomy, insulin receptor β-subunit autophosphorylation was not significantly altered, increasing only 33% (mean, n=2) compared to controls, whereas the level of pp185 tyrosine phosphorylation was markedly increased (315%) compared to sham-operated controls.

In these experiments control (sham-operated) or hypophysectomized male Sprague-Dawley rats (100–125 gram initial body weight) were fed ad libitum, and used 3–5 weeks after surgery. Anesthetized rats received an intraportal infusion of saline without or with $10^{-6}$M insulin for 0.5 min. The entire liver was excised and processed for anti-PY immunoprecipitation and immunoblotting as described in above. The results are representative of the same experiment repeated twice.

Tissue distribution studies if insulin receptor kinase mediated tyrosine phosphorylation of endogenous cellular proteins is an obligatory component of the metabolic regulatory effects of insulin in vivo, then this process should occur in organs besides the liver. To determine the tissue distribution of phosphotyrosyl proteins male Sprague-Dawley rats were anesthetized and saline without or with $10^{-6}$M insulin was infused into the portal vein (for liver) or the inferior vena cava (other tissues) for 1 minute at 1 cc/min. Tissues were excised and phosphotyrosyl proteins analyzed by anti-PY antibody immunoprecipitation and immunoblotting as described above. Liver, kidney, spleen, brain, and hindlimb skeletal muscle, and epididymal fat pads were examined under basal and insulin-stimulated conditions. In both the absence or presence of insulin, all tissues examined contain an Mr=120 kDa phosphotyrosyl protein and as noted above in the liver, the intensity of this band is unaffected by insulin. In skeletal muscle, a major insulin target tissue, insulin clearly stimulates insulin receptor β-subunit autophosphorylation together with the appearance of a prominent phosphotyrosyl protein at Mr+185 kDa, comparable in intensity to the muscle insulin receptor and to hepatic pp185. An analogous pattern of receptor and pp185-like protein phosphorylation is also observed in rat epididymal fat pads. In this tissue an additional, distinct phosphotyrosyl protein at Mr=60 kDa also appears after acute insulin stimulation. This band is more clearly resolved by a 10% gel and no bands of lower Mr are evident. The Mr=60 kDa phosphotyrosyl protein has been reported previously (Mooney et al., 1989, Endocrinology 124:422–429, hereby incorporated by reference; Momomura et al., 1988, Biochem. Biophys. Res. Comm 155:1181–1186, hereby incorporated by reference) in insulin-treated, isolated adipocytes and may be a unique substrate of the insulin receptor kinase specific to the fat cell. Kidney, without insulin contains an Mr=195 kDa phosphotyrosyl protein and after insulin stimulation this band either disappears or broadens and migrates at a slightly lower Mr. Spleen and brain do not contain detectable tyrosine phosphorylated insulin receptors and no new phosphotyrosyl proteins appeared following insulin infusion. There is an intense insulin-insensitive band in brain at Mr=190 kDa.

Coordinate Phosphorylation of the Insulin Receptor Kinase and Its 175 kDa Endogenous Substrate in Rat Hepatocytes Overview To investigate the early events in insulin signal transmission in liver, isolated rat hepatocytes were labeled with $^{32}$P, and proteins phosphorylated in response to insulin were detected by immunoprecipitation with anti-phosphotyrosine and anti-receptor antibodies and analyzed by SDS-PAGE and autoradiography. In these cells insulin rapidly stimulated tyrosine phosphorylation of two proteins: the 95 kDa β-subunit of the insulin receptor and a 175 kDa phosphoprotein (pp175). Both proteins were precipitated by anti-phosphotyrosine antibody, whereas only the insulin receptor was recognized using anti-insulin receptor antibody. In the insulin-stimulated state, both pp175 and the receptor β-subunit were found to be phosphorylated on tyrosine and serine residues. Based on precipitation by the two antibodies, receptor phosphorylation was biphasic with an initial increase in tyrosine phosphorylation followed by a more gradual increase in serine phosphorylation over the first 30 minutes of stimulation. The time course of phosphorylation of pp175 was rapid and paralleled that of the β-subunit of the insulin receptor. pp175 was clearly distinguished from the insulin receptor as it was detected only when boiling SDS was used to extract cellular phosphoproteins, whereas the insulin receptor was extracted with either Triton X-100 or SDS. In addition, the tryptic peptide maps of the two proteins were distinct. The dose response curve for insulin stimulation was shifted slightly to the left of that of the insulin receptor, suggesting some signal amplification at this step. These data suggest that pp175 is a major endogenous substrate of the insulin receptor in liver and that this may be a cytoskeletal-associated protein. Both serine and tyrosine sites are involved in insulin stimulated phosphorylation in hepatocytes.

In hepatocytes, insulin stimulates the rapid tyrosine phosphorylation of the β-subunit of the insulin receptor, which is followed by a slower rise in serine/threonine phosphorylation of the receptor. During the initial response to insulin, an endogenous substrate of $M_r$-175 kDa (pp175) is also phosphorylated on tyrosine residues in an insulin-dependent manner. This protein has a similarity to pp185, but also has some apparent differences in its properties, suggesting a family of related high molecular weight receptor substrates. This work is described in detail below.

Characterization of insulin receptor phosphorylation in rat hepatocytes $^{32}$P-labeled hepatocytes were stimulated with or without 1 μg/ml of insulin for different periods of time and extracted with 1% Triton X-100 as described below. Extract supernatants were immunoprecipitated with either anti-phosphotyrosine antibodies or with anti-insulin receptor antibodies and analyzed by SDS-PAGE. Using anti-phosphotyrosine antibody, in the basal state, phosphotyrosine containing proteins of $M_r$-200, 120 and 55 kDa were observed, but there was no tyrosine phosphorylation of the insulin receptor. Following insulin stimulation, there was appearance of a 95 kDa band corresponding to the insulin receptor β-subunit, Bernier et al., 1987, Proc Natl Acad Sci USA 84:1844–48, hereby incorporated by reference, White et al., 1985, J Biol Chem 260:9470–78, hereby incorporated by reference, and labeling of pp120 increased slightly, whereas phosphorylation of pp200 and pp55 was not affected. Both of the latter proteins could be absorbed by precipitation with protein A alone indicating the non-specific nature of their immunoprecipitation. The increase in tyrosine phosphorylation of the β-subunit of the insulin receptor reached a maximum after 1 min, plateaued for at east 20 min and then gradually declined.

Using anti-insulin receptor antibody, phosphorylation of the β-subunit of the insulin receptor could be detected in the basal state, consistent with the presence of serine and threonine phosphate before insulin stimulation, Kasuga et al., 1982, Science 215:185–87, hereby incorporated by reference. Total phosphate incorporation was increased within 1 min after insulin stimulation due to the increase in tyrosine phosphorylation. However, with anti-receptor antibody the level of phosphorylation of the β-subunit gradually increased throughout the 30 min stimulation. The different results using the two antibodies suggest that during the first minute following insulin stimulation, the β-subunit of the insulin receptor becomes phosphorylated mainly on tyrosine residues, and this is followed by a more gradual increase in phosphorylation on serine and threonine residues.

To further study the relationship between serine and tyrosine phosphorylation on the insulin receptor, the band representing the receptor immunoprecipitated by anti-insulin receptor antibody (B-9) was eluted from the gel by trypsinization and subjected to phosphoamino acid analysis. Without insulin, the receptor contained primarily phosphoserine and a small amount of phosphothreonine, but no phosphotyrosine. After one minute of insulin stimulation, there was no significant change in phosphoserine or phosphothreonine, but phosphotyrosine appeared. These results are consistent with previous studies demonstrating that the insulin receptor in the basal state contains mainly phosphoserine and that phosphotyrosine appears only after insulin stimulation, Kasuga et al., 1982, supra, Pang et al., 1985, J Biol Chem 260:7131–36 hereby incorporated by reference.

Hepatocytes were isolated and $^{32}$P-labeled as follows. Hepatocytes were isolated from male Sprague-Dawley rats weighing 160–200 g fed ad libitum using a modification, Okamoto et al., 1982, Endocrinol Jpn 29:263–7, hereby incorporated by reference, of the method of, Berry et al., 1969, J Cell Biol 43:506–20, hereby incorporated by reference. The cells were washed with 137 mM NaCl supplemented with 2.7 mM KCl and 20 mM HEPES, pH 7.4, and resuspended in phosphate-free RPMI 1640 to give a final cell concentration of $2\times10^{-6}$/ml. Cell viability was 80–90% as judged by trypan blue exclusion. Labeling of the hepatocytes with [$^{32}$P]orthophosphate was accomplished by incubating 0.5 ml aliquots of the cell suspension for 90 min with 1 mCi of [$^{32}$P]orthophosphate at 37° C. in a humidified atmosphere composed of 95% air and 5% $CO_2$.

Phosphorylation and immunoprecipitation of labeled proteins were performed as follows. After stimulation by insulin for 1 min (except as otherwise indicated), the reaction was stopped using one of two methods. For Triton X-100 extracts, the reaction was stopped by adding 0.5 ml of ice cold stopping solution composed of 50 mM HEPES, pH 7.4, 1% Triton X-100, 100 mM sodium pyrophosphate, 100 mM sodium fluoride, 10 mM EDTA, 2 mM sodium vanadate, 2 mM phenylmethylsulfonyl fluoride (PMSF) and 0.1 mg/ml aprotinin. The mixture was vigorously vortexed, cooled on dry ice-methanol until minimal ice was detected in the bottom of the tube, vortexed again and kept on ice for 30 min. For SDS extraction, 0.5 ml of boiling stopping buffer was added to give the same concentrations as described above except that 1% SDS replaced the 1% Triton, and PMSF and aprotinin were omitted. After boiling for 15 min, the sample was cooled in an ice bath for 60 min. After both extraction procedures, the samples were centrifuged at 200,00×g for 45 min at 0°–4° C. and the supernatant was used for immunoprecipitation.

Immunoprecipitation with anti-insulin receptor antibody B-9 and anti-phosphotyrosine antibody were performed at dilutions of 1:200 and 1:100, respectively, Kasuga et al., 1985, Methods of Enzymol 109:609–621, hereby incorporated by reference. Immunoprecipitated proteins were solubilized in Laemmli buffer with 100 mM dithiothreitol (DTT) and were separated in 7.5% polyacrylamide gels by electrophoresis. The gels were stained with Coomassie blue in 50% trichloroacetic acid, destained in 7% acetic acid, dried and autoradiographed with Kodak X-Omat film. Molecular weights of proteins were calculated by using standard proteins (BioRad). The incorporation of $^{32}$P into individual bands was quantitated by scanning densitometry of the film.

Phosphoamino acid analysis was performed as follows. Tryptic phosphopeptides were obtained from the protein bands in polyacrylamide gel fragments as previously described, White et al., 1985, J Biol Chem 260:9470–78, hereby incorporated by reference. The positions of the phosphorylated proteins were determined by autoradiography, the gel fragments containing the proteins was excised from the gel, washed for 12 h at 37° C. in 20% methanol, dried at 80° C. for 2 h and digested with 2 ml of 50 mM $NH_2HCO_3$ containing 100 µg of trypsin, pH 8.0. After a 6 h incubation at 37° C. another 100 µg of trypsin was added, and the digestion was continued for an additional 16 h. The supernatant was lyophilized, and the phosphopeptides were dissolved in 100 µl of 6N HCl and hydrolyzed for 2 h at 110° C. The phosphoamino acids were separated in one dimension by high voltage electrophoresis on thin layer plates (Avicel, Analtech, Newark, Del.; 250 µm) using a solution of $H_2O$: acetic acid:pyridine (89:10:1). Unlabeled phosphoserine, phosphothreonine, and phosphotyrosine standards (1 µl) were added to all samples and identified by reaction with ninhydrin, and the radioactivity was located by autoradiography.

Sprague-Dawley rats were purchased from Charles River. Collagenase (Type IV) was obtained from Cooper Biomedical; [$^{32}$P]orthophosphate and Triton X-100 from New England Nuclear; phosphoamino acids from Sigma; porcine insulin from Elanco; reagents for SDS-PAGE from Bio-Rad; Pansorbin from Calbiochem; and cellulose thin-layer plates from Analtech; RPMI 1640 tissue culture medium from GIBCO. Polyclonal anti-phosphotyrosine antibody was prepared in rabbits as previously described and affinity purified on phosphotyramine Sepharose, Pang et al., 1985, J Biol Chem 260:7131–36, hereby incorporated by reference. Anti-insulin receptor antibody was from the serum of patient B-9, Kasuga et al., 1981, J Biol Chem 256:5305–8, hereby incorporated by reference.

Phosphorylated proteins in SDS extracts of heptocytes

Although autophosphorylation of the β-subunit insulin receptor was easily detected in Triton X-100 extracts of intact rat hepatocytes using anti-phosphotyrosine antibodies, no other insulin-stimulated phosphotyrosine-containing proteins were detected. To further pursue potential substrates, SDS extracts of the hepatocytes were prepared as described above. Experiments were performed to compare the phosphoproteins solubilized from hepatocytes with Triton or SDS and precipitated with anti-phosphotyrosine antibody. Only the β-subunit of the insulin receptor was immunoprecipitated from Triton extracts as an insulin-stimulated phosphotyrosyl protein. However, when cells were extracted with 1% SDS and boiling and immunoprecipitated with anti-phosphotyrosine antibody, a new protein of Mr-175 kDa was observed in the basal state which was not present in the Triton extract. After insulin stimulation, $^{32}$P incorporation into pp175 was increased 10-fold, resulting in a labeled band which was more prominent than the β-subunit. No other phosphotyrosyl proteins were detected by SDS-PAGE using 15% and 5% gel.

Characterization of pp175

Phosphoamino acid analysis was performed on pp175 before and after insulin stimulation. In these experiments isolated rat hepatocytes were labeled with [$^{32}$P]orthophosphate and treated with insulin (1 µg/ml) for various time intervals. The cells were extracted with 1% SDS, immunoprecipitated with anti-phosphotyrosine antibody, reduced with DTT, and analyzed by SDS-PAGE with a 7.5% resolving gel. In the basal state, the major phosphoamino acid in pp175 was phosphoserine with a small amount of phosphotyrosine. After insulin stimulation, both phosphoamino acids increased. Whether the increase in phosphoserine arises from de novo phosphorylation of this protein stimulated by insulin or is only apparent due to increased recovery of the protein during immunoprecipitation with the anti-phosphotyrosine antibody is unknown.

The time course of phosphorylation of pp175 closely paralleled that of the insulin receptor β-subunit. In these experiments isolated rat hepatocytes were labeled with [$^{32}$P] orthophosphate and treated with insulin (1 μg/ml) for the indicated time intervals. The cells were extracted with 1% SDS, immunoprecipitated with anti-phosphotyrosine antibody, reduced with DTT, and analyzed by SDS-PAGE with a 7.5% resolving gel. Autophosphorylation of the β-subunit of the receptor and phosphorylation of pp175 were almost maximal within 1 min, remained elevated for 10 min and decreased at 30 min. As noted above, the phosphorylation of pp120 exhibited little or no stimulation by insulin.

Figure 1:
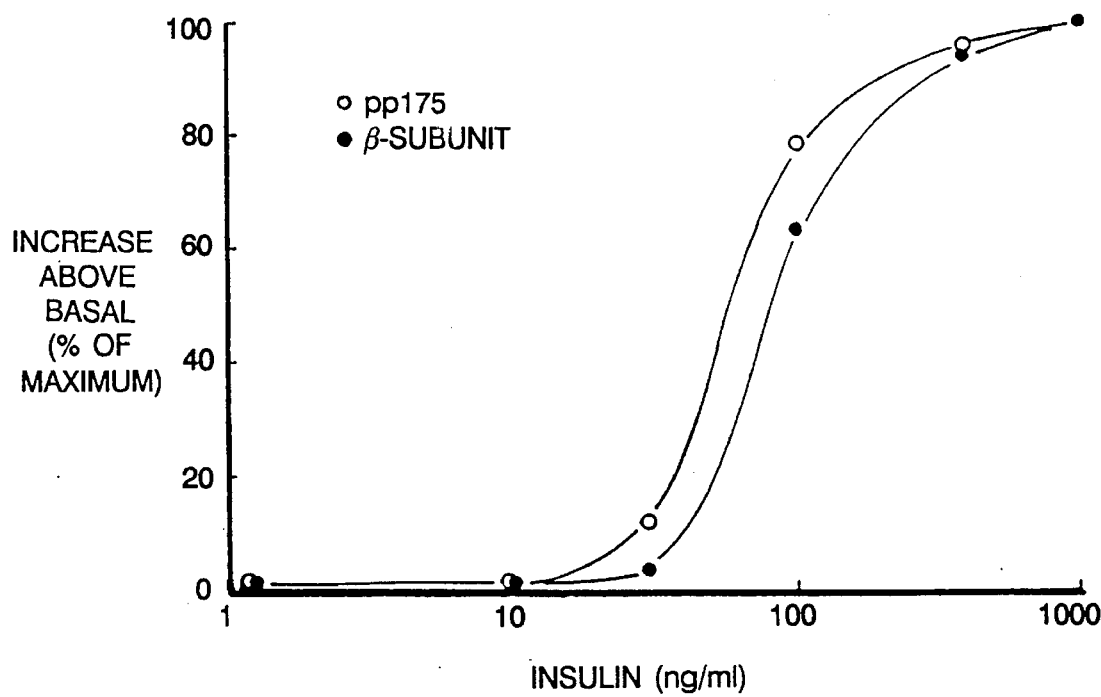

The dose-response curves for insulin stimulation of pp175 and for the insulin receptor β-subunit are shown in FIG. 1. In FIG. 1 isolated rat hepatocytes were labeled with [$^{32}$P] orthophosphate, and the cells treated with the indicated concentrations of insulin for 1 min. The cells were extracted with 1% SDS, immunoprecipitated with anti-phosphotyrosine antibody, reduced with DTT, and analyzed by SDS-PAGE with a 7.5% resolving gel. Autoradiogram of the SDS gels were subjected to densitometry scanning to quantitate the amount of $^{32}$P incorporated in the proteins. Data are presented as the percent increase above basal. Some increase in $^{32}$P incorporation into these proteins was observed with an insulin concentration of 5 nM after only 1 min of stimulation, and the effect was maximal at 100 nM. The dose-response curves for stimulation of both proteins were similar, although the $ED_{50}$ for pp175 (open circles) was slightly to the left of that of the β-subunit (closed circles) of the insulin receptor suggesting some signal amplification at this step. Both curves were about one order of magnitude less sensitive than insulin stimulation of amino acid transport in isolated hepatocytes, but similar to the curve for insulin binding to its receptor. It is important to emphasize the fact that the phosphorylation data were obtained only one minute after insulin addition, and at the lower insulin concentrations, insulin binding to its receptor probably had not come to equilibrium. This accounts, in part, for the apparent insensitivity of the cells to insulin.

Peptide mapping of pp175 and the insulin receptor

Figure 2:
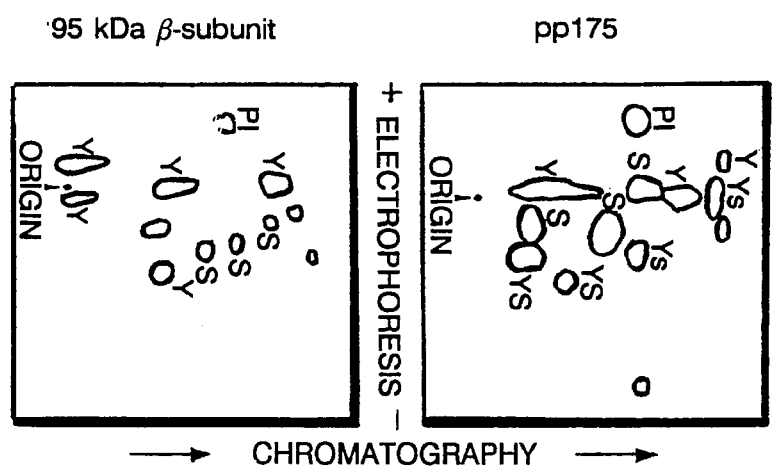
FIG. 2 is a diagram of two dimensional phosphopeptide maps of pp175 and the β-subunit of the insulin receptor.

The insulin receptor is synthesized via a proreceptor of $M_r$ ~180 kDa. Thus, pp175 could be the precursor of the insulin receptor. This seemed unlikely, however, since pp175 was not detected in Triton X-100 extracts of cells or precipitated by anti-receptor antibody, and it contained trace amounts of phosphotyrosine in the basal state (both characteristics different from those of insulin receptor). To confirm their different origin, pp175 and the 95 kDa β-subunit of the insulin receptor were subjected to two dimensional phosphopeptide mapping, FIG. 2. In FIG. 2 hepatocytes were stimulated by insulin (1 μg/ml), and the tyrosine phosphorylated proteins in hepatocytes were immunoprecipitated and separated with SDS-PAGE. The gel fragments containing the proteins were incubated with trypsin, and the eluted phosphopeptides were separated on cellulose thin-layer plates by electrophoresis (ph 1.9) and ascending chromatography (pH 3.5) as described above. FIG. 2 shows schematic diagrams of the autoradiograms. The phosphoamino acid in individual peptides was also determined. These are indicated as Y for phosphotyrosine and S for phosphoserine. When both amino acids were present the size of the letters represents the relative amount of each phosphoamino acid in the spot.

The peptide map of the β-subunit of the insulin receptor and the peptide map from pp175 showed a completely different pattern. This different peptide map was also confirmed using reverse phase HPLC (data not shown). Thus, pp175 is distinct from the insulin receptor β-subunit and not likely to represent the precursor of the insulin receptor.

HPLC separation of the tryptic phosphopeptides was performed as follows. The phosphopeptides were eluted from the gel fragments as described above with 95% efficiency and were analyzed in two ways. Two-dimensional peptide mapping was performed as described by Ellis et al., 1981, Nature (Lond) 292:506–511, hereby incorporated by reference. Peptide mapping was also performed with high performance liquid chromatography system (Waters) equipped with a wide-pore $C_{18}$ column (Bio-Rad, RP-0318) as previously described, White et al., 1985, J Biol Chem 260:9470–78, hereby incorporated by reference, Carpentier et al., 1987, J Cell Biol 105:2751–2752, hereby incorporated by reference. Phosphopeptides were applied to the column which was washed with 5% acetonitrile and eluted with an acetonitrile gradient increasing linearly to 25% during 85 min.

The Effects of Insulinomimetic Agents on pp185

Vanadate is a trace element which has been shown to be a potent insulinomimetic agent in isolated adipocytes (reviewed in Shechter et al., 1988, Biochem. Pharmac. 37:1891–1896, hereby incorporated by reference). In streptozotocin (STZ) treated diabetic rats, vanadate normalizes blood glucose, Heyliger et al., 1985, Science, 227:1474–1476, hereby incorporated by reference; Meyerovitch et al., 1987, J. Biol. Chem., 262:6658–6662, hereby incorporated by reference; and restores liver 6-phosphofructose-2-kinase glucokinase activity toward normal, Gil et al., 1988, J. Biol. Chem., 263:1868–187, hereby incorporated by reference. Vanadate has been shown to be a potent inhibitor of phosphotyrosyl protein phosphatase (PTPase) activity in vitro at concentrations which do not inhibit phosphoserine and phosphothreonine phosphatase activity, Swarup et al., 1982, J. Biol. Chem., 257:7298–7301, hereby incorporated by reference; Swarup et al., 1982, Biochem. Biophys. Res. Commun., 107:1104–1109, hereby incorporated by reference.

Under certain conditions, vanadate may also directly stimulate β-subunit tyrosine autophosphorylation and in vitro phosphotransferase activity of purified insulin receptors, Tamura et al., 1984, J. Biol. Chem., 259:6650–6658, hereby incorporated by reference; but this action has not been observed in all studies, Machicao et al., 1983, FEBS Lett., 163:76–80, hereby incorporated by reference. Vanadate increases glucose transport in trypsin-treated adipocytes and in cells where the insulin receptor concentration is reduced 60% by receptor down-regulation, Green, 1986, Biochem. J., 238:663–669, hereby incorporated by reference; suggesting a post-receptor mechanism of vanadate action.

Two well studied rodent models of Type II diabetes are ob/ob and db/db mice. These homozygous mice are characterized by obesity, hyperglycemia, hyperinsulinemia and a blunted response to insulin at the receptor and post-receptor levels, Mordes et al., 1985, Animal models of diabetes mellitus, In Joslin's Diabetes Mellitus, Marble et al., editors, Lea and Febiger, Philadelphia, 110–137, hereby incorporated by reference; Seidman et al., 1970, Diabetologia, 6:313–316, hereby incorporated by reference; Belefiore et al., 1987, Int. J. Obesity, 11:631–646, hereby incorporated by reference; Coleman et al., 1967, Diabetologia, 3:238–248, hereby incorporated by reference; Stengard et al., 1987, Biomed. Pharmacother., 41:389–396, hereby incorporated by reference; Soll et al., 1980, J. Clin. Invest., 56:769–780, hereby incorporated by reference; Chang et al., 1970, Diabetologia, 6:274–278, hereby incorporated by reference; Tannti et al., 1986, Diabetes, 35:1243–1248, hereby incorporated by reference; Vicario et al., 1987, Life Sci., 41:1233–1241, hereby incorporated by reference; Marchand-Brustel et al., 1985, Nature, 315:676–679, hereby incorporated by reference; Meyerovitch et al., 1989, J. Clin. Invest., 84:976–983, hereby incorporated by reference. The exact etiology of the two syndromes has not been elucidated, although several glycolytic and gluconeogenic enzymes are elevated in the livers of these animals. Both models demonstrate several metabolic defects consistent with peripheral insulin insensitivity, including decreased binding to liver plasma membranes and hepatocytes, Soll et al., 1980, supra; increased nonsuppressible gluconeogenesis, Coleman et al., 1967, supra; Chang et al., 1970, supra; and failure of exogenous insulin to ameliorate the syndrome, Coleman et al., 1967, supra. In spite of the decreased number of insulin receptors in the ob/ob and db/db mice, the kinase activity per receptor had been reported to be normal, Tannti et al., 1986, supra; Vicario et al., 1987, supra. However, in one study the insulin receptor kinase in the muscle of ob/ob mice was reported to be defective, Marchand-Brustel et al., 1985, supra.

The experiments presented below examine alterations in hepatic phosphotyrosyl protein phosphatase (PTPase) activity and the effects of oral administration of vanadate, an insulinomimetic agent and potent inhibitor of PTPases in vitro, in two rodent models of non-insulin dependent diabetes mellitus (NIDDM). PTPase activity was measured using a $^{32}$P-labeled peptide corresponding to the major site of insulin receptor autophosphorylation. In obese hyperglycemic ob/ob mice both cytosolic and particulate PTPase activity in liver were decreased by about 50% (p, 0.01), whereas in db/db diabetic mice, PTPase activity in the cytosolic fraction was decreased to 53% of control values (p<0.02) with no significant difference in the particulate PTPase activity.

Oral administration of vanadate (0.25 mg/ml) in the drinking water to ob/ob mice for 3 weeks lowered blood glucose level from 236±4 to 143±2 mg/dl without effect on body weight. Administration of vanadate to db/db mice produced a similar effect. The onset of the vanadate effect was relatively slow, reaching a maximum after 15–20 days of therapy. When the vanadate was discontinued, the hypoglycemic effect was slowly reversible over a similar time course. Electron microscopic examination revealed no signs of hepatotoxicity after 47 days of treatment. When tested by immunoblotting with anti-phosphotyrosine antibody, after in vivo stimulation, there was a slight reduction in insulin receptor autophosphorylation and the phosphorylation of the endogenous substrate of the insulin receptor, pp185, was markedly decreased in the ob/ob mice. Vanadate pretreatment increased the phosphorylation of the pp185 in control, but not in the ob/ob mice. The treatment with vanadate, however, did not alter hepatic PTPase activity as assayed in vitro. These data indicate that oral administration of vanadate is an effective hypoglycemic treatment in NIDDM states, and support a post insulin receptor mechanism of action of vanadate.

Data concerning blood glucose, body weight and plasma insulin levels in ob/ob and db/db mice and their matched controls are presented in Table II. Blood glucose and serum insulin levels, as well as the body weights, were markedly increased in the both diabetic models compared to the control mice. These experiments are described in more detail below.

Figure 3:
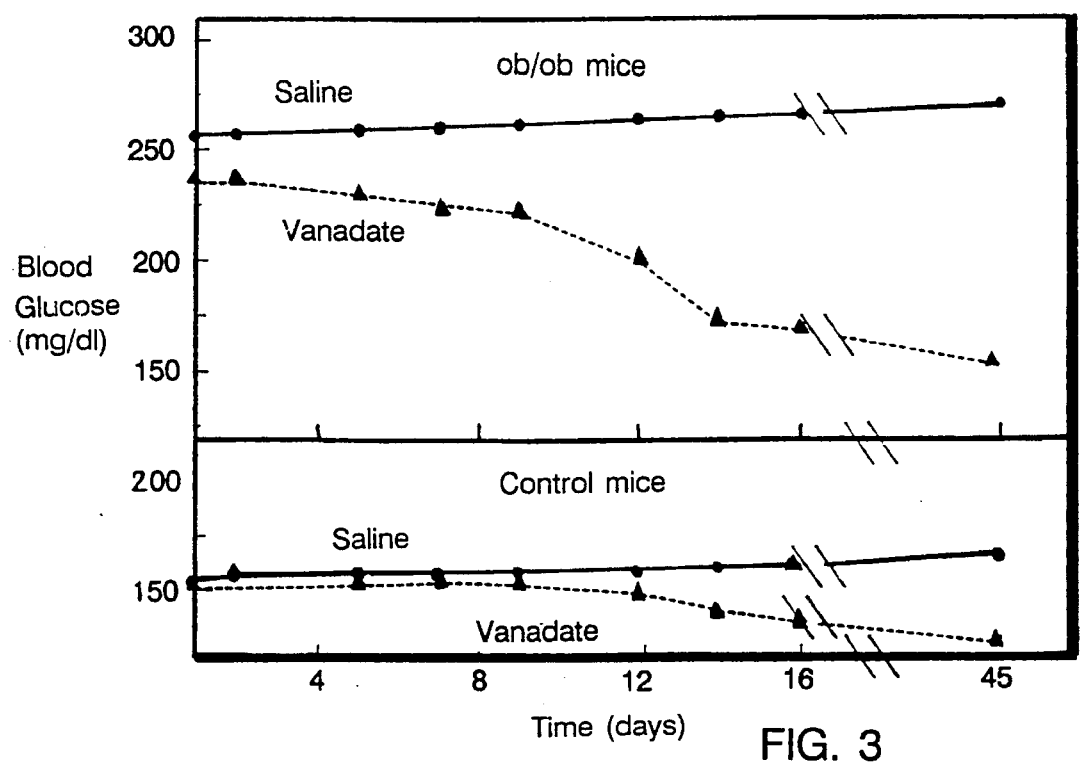
FIG. 3 is a graph of the effect of vanadate on blood glucose levels in ob/ob mice.

Effect of Vanadate Treatment on ob/ob mice:

After 47 days of treatment with vanadate, the blood glucose levels of the treated ob/ob mice was 143±2 mg/dl compared to 276±3 mg/dl in the control untreated ob/ob mice (p<0.001, Table II and FIG. 3.

FIG. 3 shows the effect of oral administration of vanadate on ob/ob mice on blood glucose level. Ob/ob mice (upper panel) and their matched controls ob/+ (lower panel) were treated with vanadate (NaVO$_3$, 0.25 mg/ml and 80 mmol/l NaCl) in the drinking water (solid lines) or with 80 mmol/l NaCl alone (dashed lines). Each point is the mean of 5 animals. The S.E.M. was 2–3 mg/dl.)

TABLE II

CHARACTERISTICS OF MICE

| Groups | n | Body Weight (g) | Blood Glucose (mg/dl) | Insulin (µU/ml) |
|---|---|---|---|---|
| ob/+ | 6 | 32.4 ± 0.1 | 64 ± 2 | 44 ± 7 |
| ob/ob | 6 | 45.0 ± 0.1* | 406 ± 2 | 170 ± 30* |
| db/+ | 6 | 32.2 ± 02. | 70 ± 2 | 27.2 ± 2 |
| db/db | 6 | 36.8 ± 0.4* | 319 ± 2 | 410 ± 24* |

The data are represented as the mean ± S.E.M. * − p < 0.001 for ob/ob vs ob/+ and db/db vs db/+.

The vanadate treatment also lowered the blood glucose level of lean ob/+ mice from 170±4 mg/dl to 114±1 mg/dl (p<0.001). In both the ob/ob and the ob/+ groups, there was no difference in body weight in the vanadate-treated mice as compared to their appropriate saline-treated controls (Table II).

TABLE III

EFFECT OF VANADATE TREATMENT ON ob/ob MICE

| Groups | Treatment | Body Weight (g) | Blood Glucose (mg/dl) | Insulin (µU/ml) | Binding (%/10 µg) |
|---|---|---|---|---|---|
| ob/+ | Control | 35.3 ± 0.1 | 170 ± 4 | 57 ± 10 | 17.3 ± 3.8 |
| ob/+ | Vanadate | 34.9 ± 0.2 | 114 ± 1 | 68 ± 15+ | 10.3 ± 1.9 |
| ob/ob | Control | 40.0 ± 0.1* | 276 ± 3*+ | 272 ± 25* | 8.1 ± 1.8# |
| ob/ob | Vanadate | 40.0 ± 0.2* | 143 ± 2+ | 398 ± 40+ | 7.3 ± 1.3# |

The vanadate treatment was for 47 days, controls received saline only in their drinking water.
The data are represented as the mean ± S.E.M. Sample size is 5 per group.
*p < 0.001 compared to ob/+ mice.
+p < 0.001 compared to non treated mice.
p < 0.05 compared to ob/+ mice.

Figure 4:
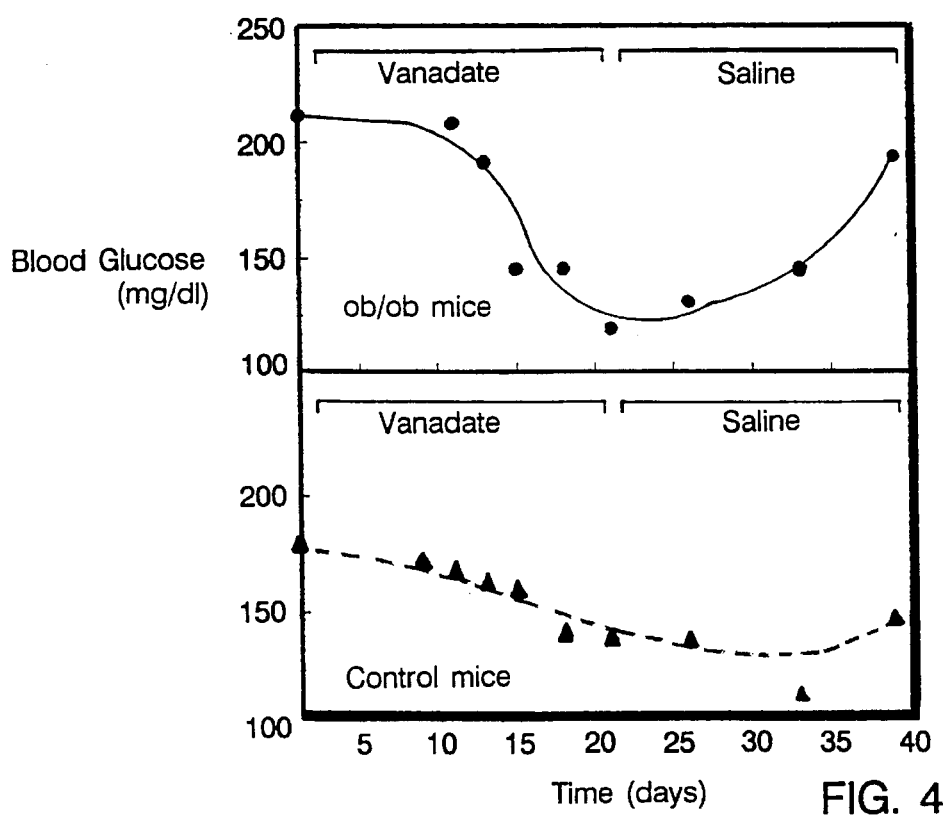
FIG. 4 is a graph of the effect of vanadate on blood glucose level in ob/ob mice.

Circulating levels of vanadate were 5.2±0.9 µM and 2.7±0.5 µM in the ob/+ mice after 3 weeks of treatment. These levels are similar to vanadate levels previously reported by us and others, Meyerovitch et al., 1987, supra; Gil et al., 1988, supra. Untreated mice have no detectable (<7 nM) serum vanadate, Stoop et al., 1982, Clin. Chem., 28:79–82; hereby incorporated by reference. The effect of vanadate was reversible and 20 days after withdrawal of the vanadate, the blood glucose returned to the initial hyperglycemic levels, FIG. 4. FIG. 4 shows that the effect of vanadate is reversible. The vanadate drinking water was changed to control after 20 days. The ob/ob mice are shown in the upper panel and the ob/+ mice in the lower panel. Each point is the mean of 5 animals. The S.E.M. was 2–3 mg/dl.) To determine the possible mechanism of one vanadate effect, we evaluated serum insulin levels, insulin receptor function and some post-receptor sites of hormone action.

Vanadate treatment increased plasma insulin levels from 254±29 to 338±49 µU/ml in the ob/ob, and from 66±10 to 92±20 in the ob/+ group (p<0.001). Insulin binding to WGA purified insulin receptors was reduced in the untreated ob/ob mice, (8.7±1.8 %/10 µg protein compared to 17.3±3.8 %/10 µg protein, in untreated controls, p<0.05) (Table II). After 47 days of vanadate treatment there was still a decrease in the insulin binding in the ob/ob mice (8.7±1.8 %/10 µg, p<0.05), while the vanadate treatment down regulated the level of insulin binding in the ob/+ mice to 10.3±1.9%/10 µg proteins, although this change did not reach statistical significance, Table III.

At the ultrastructural level, the livers of obese mice were heavily laden with glycogen and lipid droplets, with much variability from cell to cell. There was an increasing gradient in the number of lipid droplets from the portal triad to the central vein. For this reason hepatocytes from the protal triad from all groups were compared. With both the ob/ob or lean ob/+, there was no apparent difference between vanadate-treated and control mice, thus demonstrating a lack of major toxicity to the liver by vanadate.

Effect of Vanadate Treatment on db/db mice

Treatment of db/db mice with vanadate lowered the blood glucose levels from 228±6 to 141±1 mg/dl (p<0.001). This effect was maximal after 55 days of treatment, with half the effect observed after 23 days, Table IV and FIG. 5.

Figure 5:
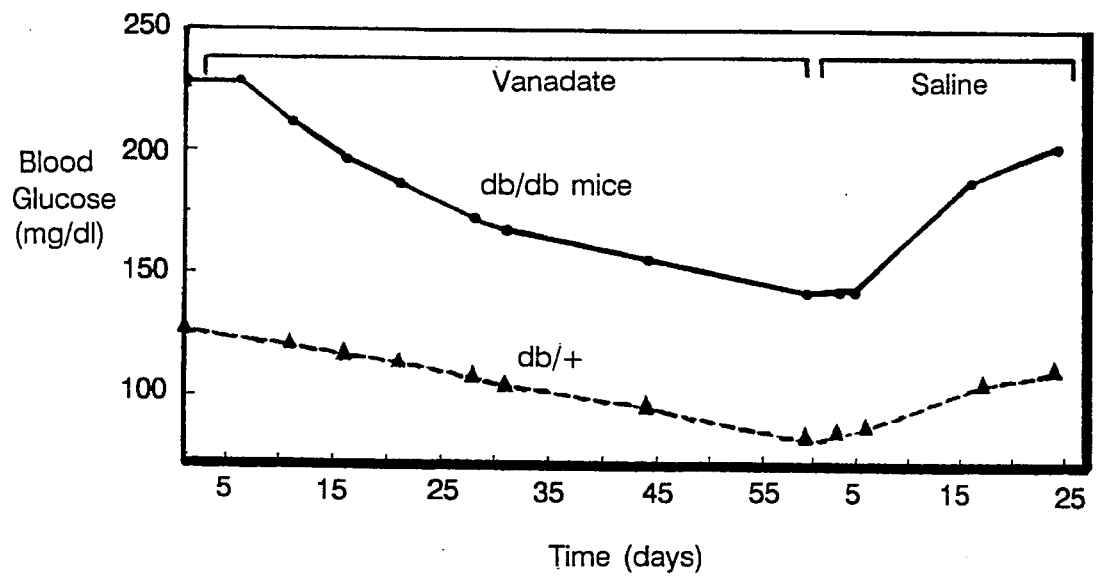
FIG. 5 is a graph of the effect of vanadate on blood glucose level in db/db mice.

FIG. 5 shows the effect of oral administration of vanadate on blood glucose level in db/db mice. Db/db mice (solid line) and their matched controls db/+ (dashed line) were treated with vanadate as described in FIGS. 3 and 4. Sixty days after treating the mice, the vanadate had been changed into the control solution. Each point is the mean of 5–6 mice. The S.E.M. was 2–3 mg/dl.)

withdrawal of the vanadate the blood glucose returned to the initial hyperglycemic levels, FIG. 5.

Effect of Diabetes and Vanadate on PTPase Activity

Figure 6:
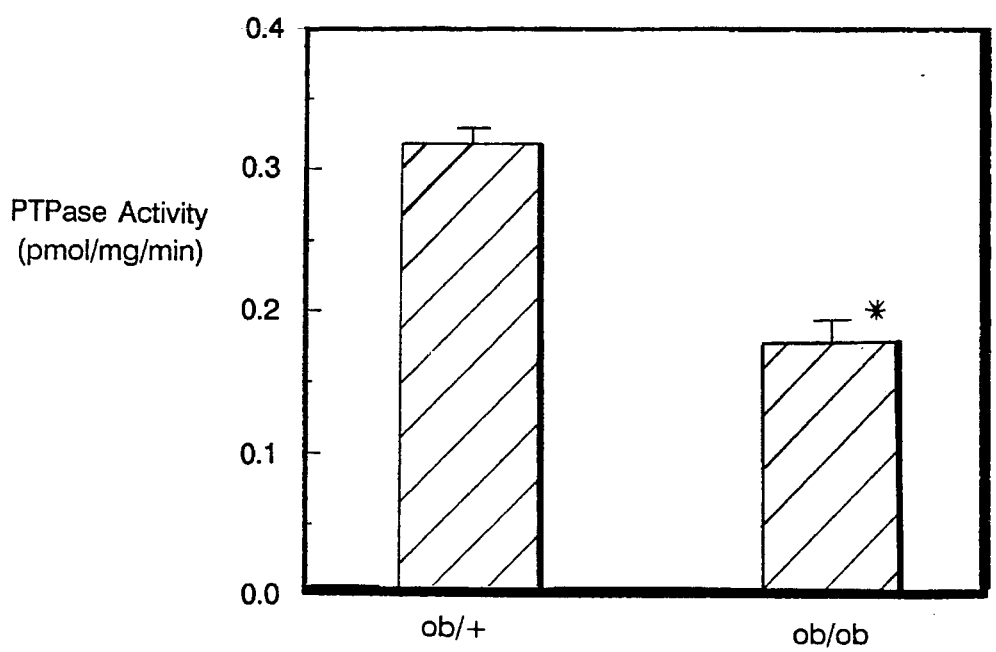
FIG. 6 is a comparison of PTPase activity in the cytosolic liver fraction of ob/+ and ob/ob mice.

PTPase activity present in cytosolic extracts of liver from the 8 week old ob/ob mice was 55% that of the ob/+ (0.18±0.02 U/mg and 0.33±0.03 U/mg, p<0.01) when assessed in vitro using the phosphorylated 1142–1153 peptide as substrate FIG. 6.

Figure 7:
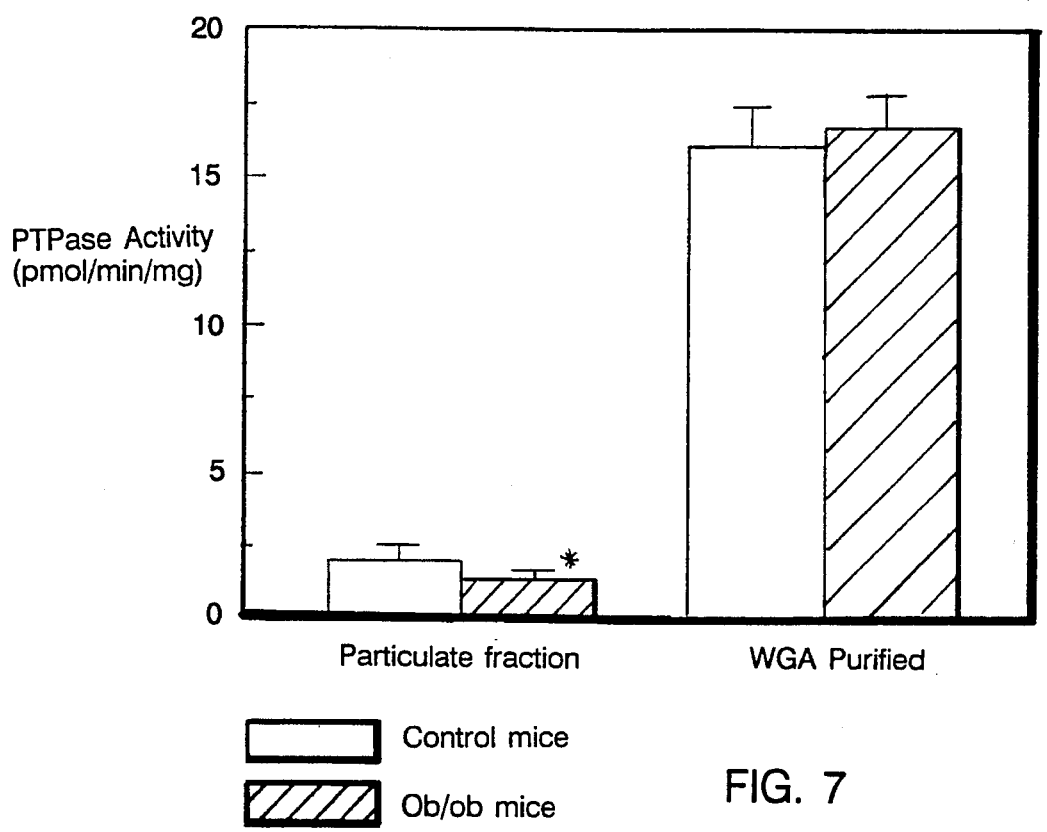
FIG. 7 is a comparison of the PTPase activity in the particulate and WGA purified fractions of livers from ob/ob and ob/+ mice.

FIG. 6 shows PTPase activity in cytosolic fractions and FIG. 7 shows particulate and WGA purified fractions from livers of ob/ob and ob/+ mice. Liver fraction derived from ob/ob and ob/+ mice were fractionated using isotonic sucrose differential centrifugation. The particulate fraction was than further fractionated on WGA columns. The 1142–1153 peptide was phosphorylated at 4° C. in the presence of 100 nM insulin using WGA purified insulin receptor as described in the methods. The $^{32}$P labeled peptide was separated from the $^{32}$P ATP by chromatography on AG 1-X2 acetate column and by SEP-PAK cartridge and lyophilized. Aliquots from each fraction were assayed for PTPase activity towards the phosphorylated peptides (0.14 µM) in the presence of 2 mM EDTA and 1 mM DTT for 5 min at 30° C. The reaction was stopped by precipitation with 10% TCA and $^{32}$P$_i$ release was measured by organic extraction of P$_i$ (27). The results represent the mean±S.E.M. of six mice in each group assayed in duplicate. FIG. 6: Cytosolic PTPase activity on ob/ob mice and their controls. *=<0.01. FIG. 7: Particulate and WGA purified PTPase activity in ob/ob mice and their controls. *=<0.02.

PTPase activity associated with the particulate fractions was similarly decreased in the ob/ob mice versus the ob/+ controls (1.43±0.2 U/mg and 2.1±0.3 U/mg, p<0.02), FIG. 7. The glycoprotein fraction of the membrane had 5- to 8-fold higher specific activity than the particulate fraction, however, specific activities of the PTPase in the WGA purified particulate fractions were not different between ob/ob and/ob/+ mice (16.1±1.3 U/mg versus 16.8±1 U/mg, FIG. 7).

Figure 8:
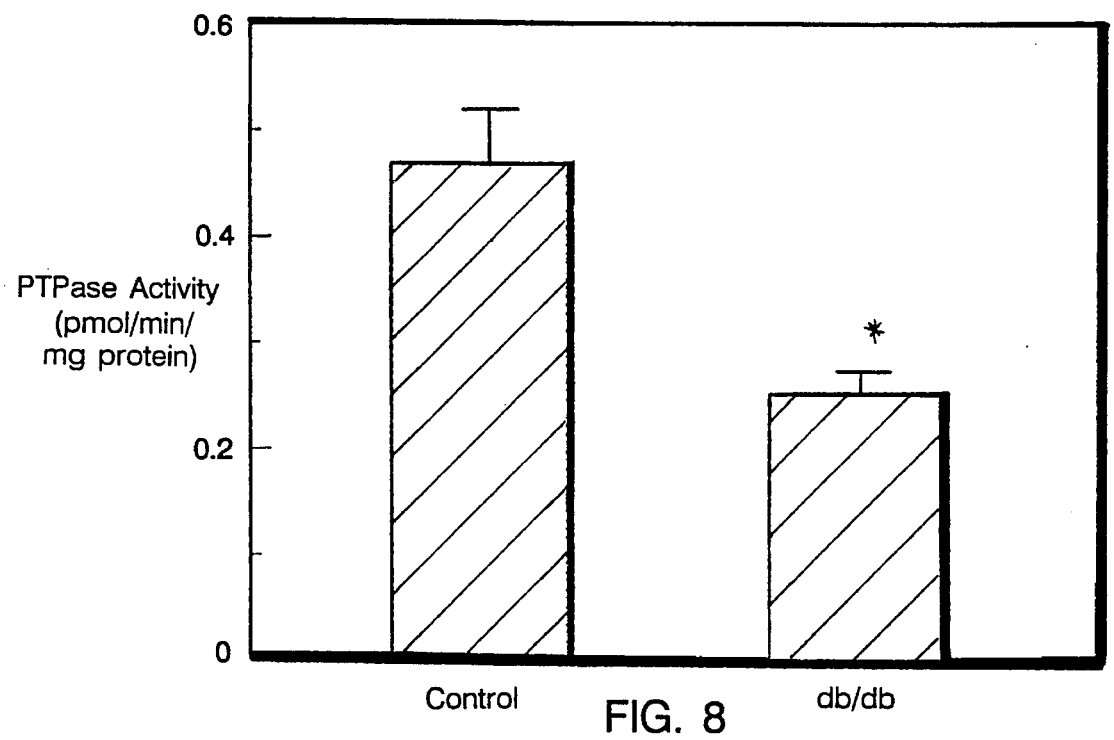
FIG. 8 is a comparison of the PTPase activity in cytosolic liver fraction from db/db and control mice.

In the 8 week old db/db mice, the cytosolic PTPase activity was also decreased by about 50% (0.25±0.03 U/mg versus 0.47±07 U/mg, p<0.02), FIG. 8. No significant difference was found in the PTPase activity associated with the particulate fraction, FIG. 9, and thus activity in the glycoprotein fraction-enriched fraction was not determined. FIG.

TABLE IV

EFFECT OF VANADATE TREATMENT ON db/db MICE

| Groups | Treatment | n | Body Weight change (g/day) | Blood Glucose (mg/dl) | Insulin (µU/ml) |
|---|---|---|---|---|---|
| db/+ | Vanadate | 6 | 0.6 ± 0.02 | 104 ± 1 | 48 ± 5 |
| db/+ | Control | 5 | 0.05 ± 0.003 | 106 ± 1 | 42 ± 3 |
| db/db | Vanadate | 6 | 0.06 ± 0.003 | 167 ± 1# | 198 ± 10*+ |
| db/db | Control | 5 | 0.06 ± 0.002 | 191 ± 2 | 339 ± 52 |

The vanadate treatment was for 60 days, controls received saline only in their drinking water.
The data are represented as the mean ± S.E.M.
*p < 0.025 compared to db/db with control treatment
+p < 0.001 compared to db/+.
p < 0.001 compared to non treated db/db and db/+ mice.

Figure 9:
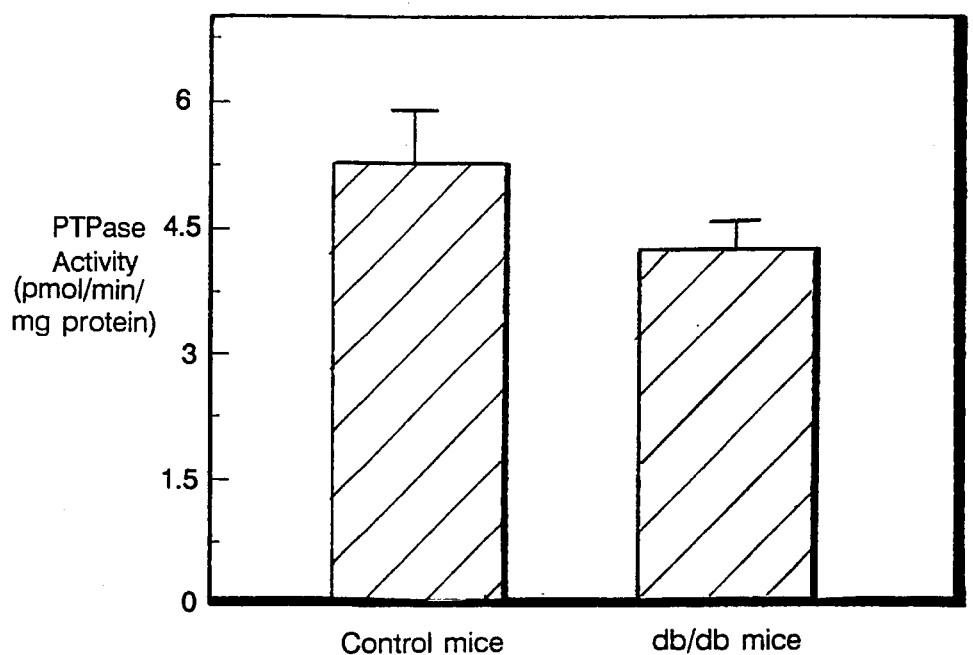
FIG. 9 is a comparison of the PTPase activity in the particulate fraction from the livers of db/db and control mice.

The vanadate treatment also lowered the blood glucose level of the db/+ mice from 126±2 to 81±1 mg/dl. There was no difference in body weight gain treatment with vanadate or with saline for either the db/db or the db/+ groups (Table IV). The effect of vanadate was reversible, and 25 days after 8 shows activity in cytosolic fractions and FIG. 9 shows activity in particulate fractions from db/db mice livers. PTPase activity was assayed in cytosolic and in particulate fractions. Liver fractionation and PTPase assay methods were as described in FIG. 3. *=<0.2.

Figure 10:
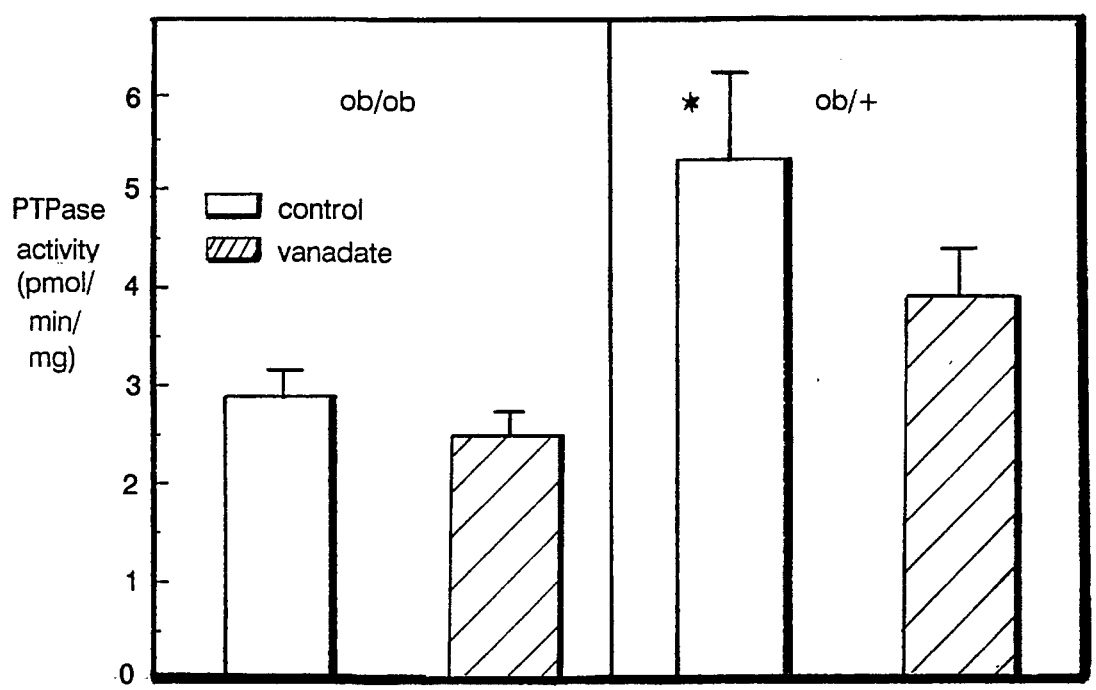
FIG. 10 is graph of the effects of vanadate treatment on PTPase activity in particulate fractions from ob/ob mouse livers.

After 9 weeks of treatment, vanadate did not significantly alter particulate PTPase activity in the 17 week old ob/ob mice compared to the age-matched untreated ob/ob mice, FIG. 10.

FIG. 10 shows the effects of vanadate treatment on PTPase activity in particulate fractions from ob/ob mice liver. Left panel; ob/ob mice, right panel; ob/1$^+$ mice. Forty-seven days after oral administration of vanadate (hatched bars) or solution (empty bars). Particulate PTPase activity from the ob/ob mice livers was assayed as described in FIGS. 6 and 7. The results represent mean±S.E.M. of five mice in each group assayed in duplicate. *=p <0.02.

The specific activity of the PTPase activity in the particulate fraction of the ob/ob mice was 55% of ob/+ (2.93 ±0.4 U/mg versus 5.3±0.9 U/mg, p<0.02), FIG. 10. Vanadate treatment did result in a decrease in PTPase activity in the ob/+ mice (3,9±0.5 U/mg in the treated versus 5.3±0.5 in the control animals); however, the change was not statistically significant, FIG. 10. No significant differences in cytosolic PTPase activity were observed in this age groups (data not shown).

Effect of Vanadate Treatment on Phosphorylation of 95 kDa and 185 kDa

To determine whether administration of vanadate produced insulinomimetic metabolic effects in the liver of ob/ob through increased tyrosine phosphorylation of the insulin receptor β-subunit or other cellular substrates of the insulin receptor kinase, such as pp185, the phosphotyrosyl proteins in intact mice liver were analyzed by immunoblotting with anti-phosphotyrosine antibodies before and after acute insulin stimulation in vivo.

In these experiments ob/ob and control mice were treated for 9 weeks with vanadate or control solutions. Phosphotyrosyl proteins from the liver were isolated as described in above. Briefly, mice were anesthetized, the abdominal wall was incised to expose the viscera. Normal saline or 10$^{-6}$M insulin was infused for 20 seconds, after when the liver excised and homogenized in 1% SDS, 100 mM HEPES pH 7.5 50 nM DTT at 100° C. for 5 min. The denatured proteins were precipitate with TCA, and immunoprecipitated with polyclonal anti-phosphotyrosine antibodies. The immunoprecipitated phosphotyrosyl proteins were resolved on 6% SDS-polyacrylamide gels, transferred to nitrocellulose and detected with anti-phosphotyrosine antibodies and [I$^{125}$]- Protein A and subject to autoradiography. The experiment was preformed twice with similar results.

In the absence of insulin, only a single, major constitutive phosphotyrosyl protein at Mr=120 kDa was present in all animals. The identity and function of this protein is not known, and its phosphotyrosine content is not altered by vanadate or insulin treatment. After insulin infusion into the portal vein, the insulin receptor β-subunits (Mr=95 kDa) become tyrosine phosphorylated. The extent of receptor autophosphorylation is similar in all animals. Vanadate treatment did not significantly increase receptor autophosphorylation. Insulin infusion also induced tyrosine phosphorylation of the endogenous substrate of the insulin receptor, or protein with an Mr about 185 kDa. The phosphorylation level of the putative endogenous substrate of the insulin receptor, pp185, was markedly decreased in the ob/ob compared to the ob/+. Vanadate treatment significantly augmented pp185 phosphorylation in control mice, however, vanadate did not increase the phosphorylation of the pp185 in the ob/ob mice. There were no new phosphotyrosyl proteins detected in the vanadate treated mice compared with control treated mice.

Materials and methods

[γ-$^{32}$P]ATP (3000 Ci/mmol) was obtained from New England Nuclear (Boston, Mass.); wheat germ agglutinin agarose (WGA) was from Vector Laboratories (Burlingame, Calif.); sodium orthovanadate was from Aldrich Chemical Company, Inc. (Milwaukee, Wis.). Streptozotocin, HEPES, phenylmethylsulfonyl fluoride (PMSF), N$^\alpha$-P-tosyl-L-lysine chlormethyl ketone (TLCK), N$^\alpha$-tosyl-l-phenylalanine chlormethyl ketone (TPCK), aprotinin, N-acetyl-D-glucosamine were from Sigma Chemical (St. Louis, Mo.). Silicotungstic acid was from J. T. Baker Chemical Co. (Phillipsburg, N.J.). Dithiothreitol (DTT), Coomassie blue Triton X-100 and AG 1-X2 acetate were purchased from Bio-Rad Laboratories, (Richmond, Calif.). The synthetic peptide, Thr-Arg-Asp-Ile-Tyr-Glu-Thr-Asp-Tyr-Tyr-Arg-Lys (SEQ ID NO:24), which contains the amino acid sequence between residues 1142–1153 of the insulin receptor β-subunits, Ullrich et al., 1985, Nature, 313:756– 761, hereby incorporated by reference; was purchased from Dr. David Coy, Tulane University (New Orleans, La.). 3-[(3-cholamidopropyl) dimethylammonio]-2 hydroxyl-1propanesulfonate (CHAPSO) was purchased from Pierce Chemicals (Rockford, Ill.).

Female obese-hyperglycemic mice (C57B1/6J ob/ob) and the obese diabetic mice (C57B1/KsJ db/db) and their lean matched controls (ob/+) and (db/+) were purchased from Jackson Laboratory (Bar Harbor, Me.) and used at 6–8 weeks of age. Mice were fed ad libitum a standard laboratory chow. The fed mice were anesthetized by ether and then bled through the orbital venous plexus. Venous blood and liver sample were taken between 9–11 a.m. As noted in the figure legends and text, some mice were treated with vanadate (0.25 mg/ml) included in the drinking water. 80 mM NaCl was also included to reduce vanadate toxicity, as previously described, Heyliger et al., 1985, supra; Meyerovitch et al., 1987, supra. For these experiments, control mice were treated with 80 mM NaCl alone.

$^{32}$P-labelled peptide 1142–1153 was prepared as follows. Wheat germ agglutinin purified insulin receptor, Kasuga et al., 1984, Methods Enzymol., 109:609–621, hereby incorporated by reference; was incubated with 100 nM insulin for 30 minutes at 4° C. after which 100 μM [v-$^{32}$P]ATP (specific activity 14.2 Ci/mol), 5 mM Mn$^{2+}$ and 2 mM 1142–1153 peptide were incubated with the receptor overnight at 4° C. $^{32}$P-peptide was separated from $^{32}$P-ATP by chromatography on AG1-X2 acetate column (29) and on a C-18 SEP-PAK cartridge (Waters Associates, Milford, Mass.) and lyophilized.

Tissue extractions were performed as follows. Mice were sacrificed by cervical dislocation, and livers were rapidly removed. All tissue extractions were performed at 4° C. Livers were homogenized using a Potter-Elvejhem type homogenizer rotating at 1300 rpm for 20 seconds in three columns of buffer A (20 mM Tris-HCL, pH 7.5, 50 mM 2-mercaptoethanol, 250 mM sucrose, 2 mM EDTA, 10 mM EDTA, aprotinin 10 μg/ml, leupeptin 25 μg/ml, 0.1 mM TLCK, 0.1 mM TPCK, 0.5 mM benzamidine, 0.2 mM phenylmethylsulfonyl fluoride and 5 μg/ml each of pepstatin A, antipain and chymostatin). Homogenates were centrifuged at 10,000×g for 20 minutes, and the supernatant was further centrifuged at 100,000×g for 45 minutes. The final supernatant was designated the cytosolic fraction. The pellet resulting from the 100,000×g spin was solubilized using a Potter-Elvejhem type homogenizer rotating at 1300 rpm for 5 minutes in buffer A containing 1% (W/V) CHAPSO and was then centrifuged 45 minutes at 100,000×g to remove insoluble material. The solubilized material in the supernatant was designated the particulate fraction. In some experiments, this fraction was further fractionated by chromatography on WGA-agarose columns. After application, the column was washed with 50 bed volumes of 10 mM HEPES buffer, pH 7.6, 0.1% (v/v) Triton 100, 5 mM EDTA, 0.5 mM benzamidine and 0.2 mM PMSF and 2 mercaptoethanol 0.1% (v/v) (buffer B) and eluted with two bed volumes with 0.3M N-acetyl glucosamine in buffer B. The WGA purified fractions were designated the glucoprotein-enriched fractions. All preparations were stored at −70° C. prior to use.

PTPase assays were performed as follows. The dephosphorylation reaction was carried out at 30° C. in a final volume of 50 µl of 50 mM HEPES, pH 7.0, 2 mM EDTA and 1 mM DTT, and was terminated by the addition of 30 µl 10% trichloroacetic acid and 20 µl 1% (w/v) bovine serum albumin (BSA). Following incubation at 4° C. for 10 minutes and centrifugation to remove precipitated proteins, $^{32}P_i$ released from $^{32}P$-peptide was measured using organic extraction of $P_i$, Shacter, 1984, Anal. Biochem, 138:416–420, hereby incorporated by reference. Reaction rates were linear when under 20% of the phosphate was released from the peptide; therefore, the extent of dephosphorylation was kept within this limit. Concentrations of phosphotyrosyl peptide were calculated from the $^{32}P$ content and the specific activity of $[v-^{32}P]ATP$. One unit of PTPase was defined as the amount of enzyme hydrolyzing 1 pMol of phosphate per minute.

$^{125}I$-insulin binding to solubilized insulin receptor was assayed as follows. An insulin receptor preparation was prepared as previously described, Kasuga et al., 1984, supra; and diluted in 50 mM HEPES, pH 7.6, 0.1% Triton X-100. Aliquots (5–9 µg protein) of wheat germ agglutinin eluate were incubated with 125I-insulin (0.1 ng/ml, 2,000 Ci/mmol) in the absence or presence of 1 µmol unlabeled insulin at 4° C. for 10 hours in a medium of 150 mM NaCl and 50 mM HEPES at pH 7.4 containing 0.1% BSA. Separation of receptor-bound and free insulin was performed by the polyethylene glycol method using bovine gamma globulin as carrier protein, Desbuquois et al., 1971, J. Clin. Endocrinol. Metab., 33:732–738, hereby incorporated by reference.

Hepatic phosphotyrosine containing proteins were identified in vivo as follows. A recently developed procedure was employed to measure in vivo phosphorylation involving the analytical isolation of phosphotyrosine containing proteins which appear in response to hormonal stimulation of intact tissues. Mice were anesthetized with sodium amobarbital (200 mg/kg body weight, intraperitoneal). The abdominal wall was incised to expose the viscera. Normal saline with or without $10^{-6}M$ insulin (Humulin R, Eli Lilly) was infused into the portal vein for 20 seconds at a rate of 0.2 ml/minutes. The entire liver was than excised and homogenized in 1% sodium dodecyl sulfate, 50 mM dithiothreitol, 100 mM HEPES, 2mM EDTA, pH 7.5 at 100° C. for 5 minutes. The denatured proteins were precipitated with TCA (10% w/v). The TAC was removed using 3 washings with 1:1 (v/v) ether: ethanol. The proteins were resuspended in 50 mM TRIS buffer, pH 7.5, and immunoprecipitated with rabbit polyclonal anti-phosphotyrosine antibodies. Immunoprecipitated phosphotyrosyl proteins were resolved on 6% SDS polyacrylamide gels, transferred to nitrocellulose and [$^{125}I$]-Protein A. The nitrocellulose membranes were then subjected to autoradiography.

Electron microscopy was as follows. After cervical dislocation, the right lobe of the liver was rapidly excised, minced in cold 2.5% glutaraldehyde, 0.1M phosphate buffer, pH 7.4 and fixed in fresh fixative at 4° C. overnight. Tissue was rinsed in the same buffer, fixed with osmium, dehydrated in graded alcohols and embedded in Araldite. Ultrathin sections were picked up on copper grids and stained with uranyl acetate and lead citrate. Areas adjacent to portal triads were viewed using a Phillips 301 electron microscope.

Analytic methods were as follows. Blood glucose levels were determined using ACCU-CHEC II (Boehringer Mannheim Diagnostics Division, Indianapolis, Ind.). Plasma immunoreactive insulin concentration was determined by radioimmunoassay using the polyethylene glycol method, Desbuquois et al., 1971, supra. Serum concentrations of vanadate were determined by flameless atomic absorption spectroscopy, Stoop et al., 1982, supra. The lower limit of detection was 7 nM concentration. Protein concentrations were determined by the method of Bradford, Bradford, 1976, Anal. Biochem., 72:248–254, hereby incorporated by reference; using IgG immunoglobulin as a standard.

Data are presented as mean±S.E.M. The unpaired student's t-test (two tailed) was used to compare two groups, and analysis of variance was used to compare more than two groups.

The Molecule Structure of the Insulin Receptor or Substrate

Partial amino acid sequence of IRS-1 and preparation of cDNA probes

Phosphotyrosine-containing proteins were partially purified from extracts of basal or insulin-stimulated rat liver by affinity chromatography on immobilized anti-phosphotyrosine antibodies, as described above. The eluted proteins were separated by 1-dimensional SDS-PAGE and transferred to nitrocellulose, from which the pp185 band was excised and digested with trypsin. Tryptic peptides eluted from the nitrocellulose were separated by reverse-phase HPLC, as described above. Several peptide fractions were subjected to amino acid sequence analysis revealing two classes of peptide sequences. Class I peptides were found only in the insulin-stimulated extracts, whereas Class II peptides were found in both the basal and insulin-stimulated extracts. Based on a search of the translated Genebank, the Class I peptide sequences were unique and attributed to the insulin receptor substrates in the pp185 band, whereas Class II peptide sequences were identical to rat liver carbamyl phosphate synthase which apparently binds non-specifically to the affinity matrix. It was assumed provisionally that the Class I peptides were derived from a single 175 kDa phosphotyrosine-containing substrate in the pp185 band which termed IRS-1; however, the actual relationship between each peptide was unknown.

Figure 11:
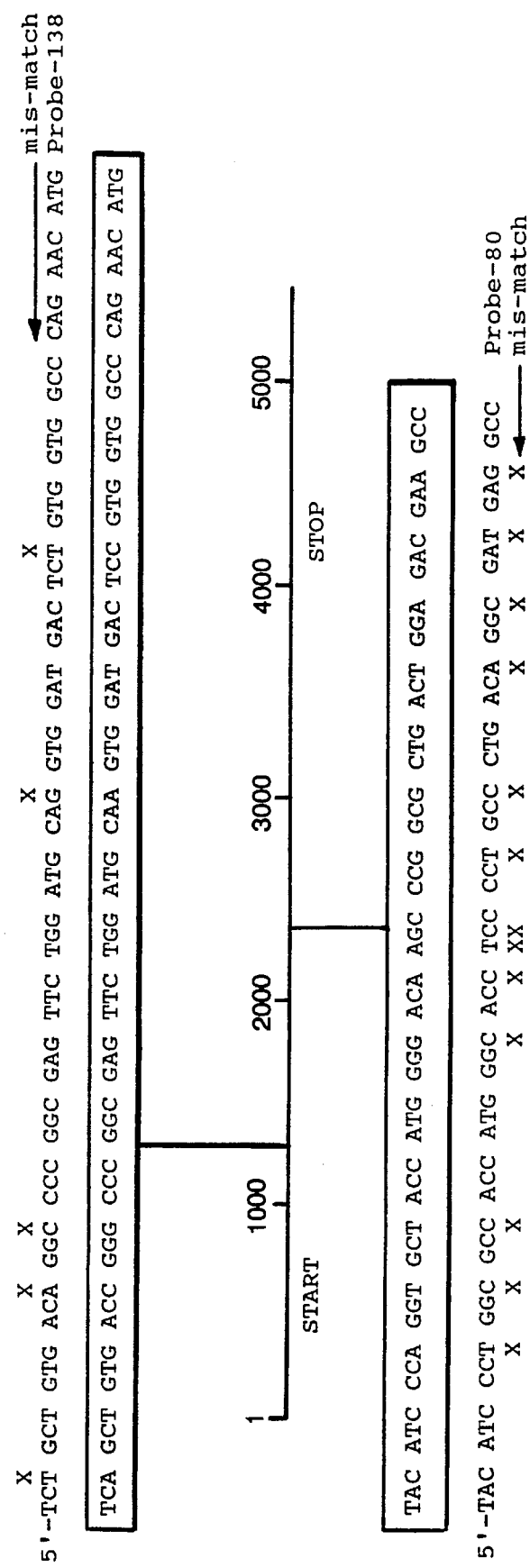
FIG. 11 is a map of probes 138 (SEQ ID NO: 2) and 80 (SEQ ID NO: 3).

The unique Class I peptide sequences obtained from the tryptic digest of the pp185 band are listed in Table I. Pep-80 and Pep-138 were the longest and most reliable amino acid sequences obtained, and they were used to prepare two long "optimal" cDNA probes according to the rules for codon usage developed by Lathe, 1985 J. Mol. Biol. 183:1, hereby incorporated by reference. The nucleotide sequence of each probe is shown in FIG. 11. Double-stranded [$^{32}P$]phosphate-labeled probes were prepared by synthesizing partially overlapping complementary oligonucleotides corresponding to each sequence, and then filling the 3'-overhanging ends with Klenow using high specific activity [$\alpha$-$^{32}P$]dCTP and [$\alpha$-$^{32}P$]dGTP. The resulting radioactive double-stranded probes (2 mCi/pmol) were used simultaneously to detect cognate coding sequences in rat liver cDNA libraries.

Isolation of the cDNA for IRS-1

Figure 13:
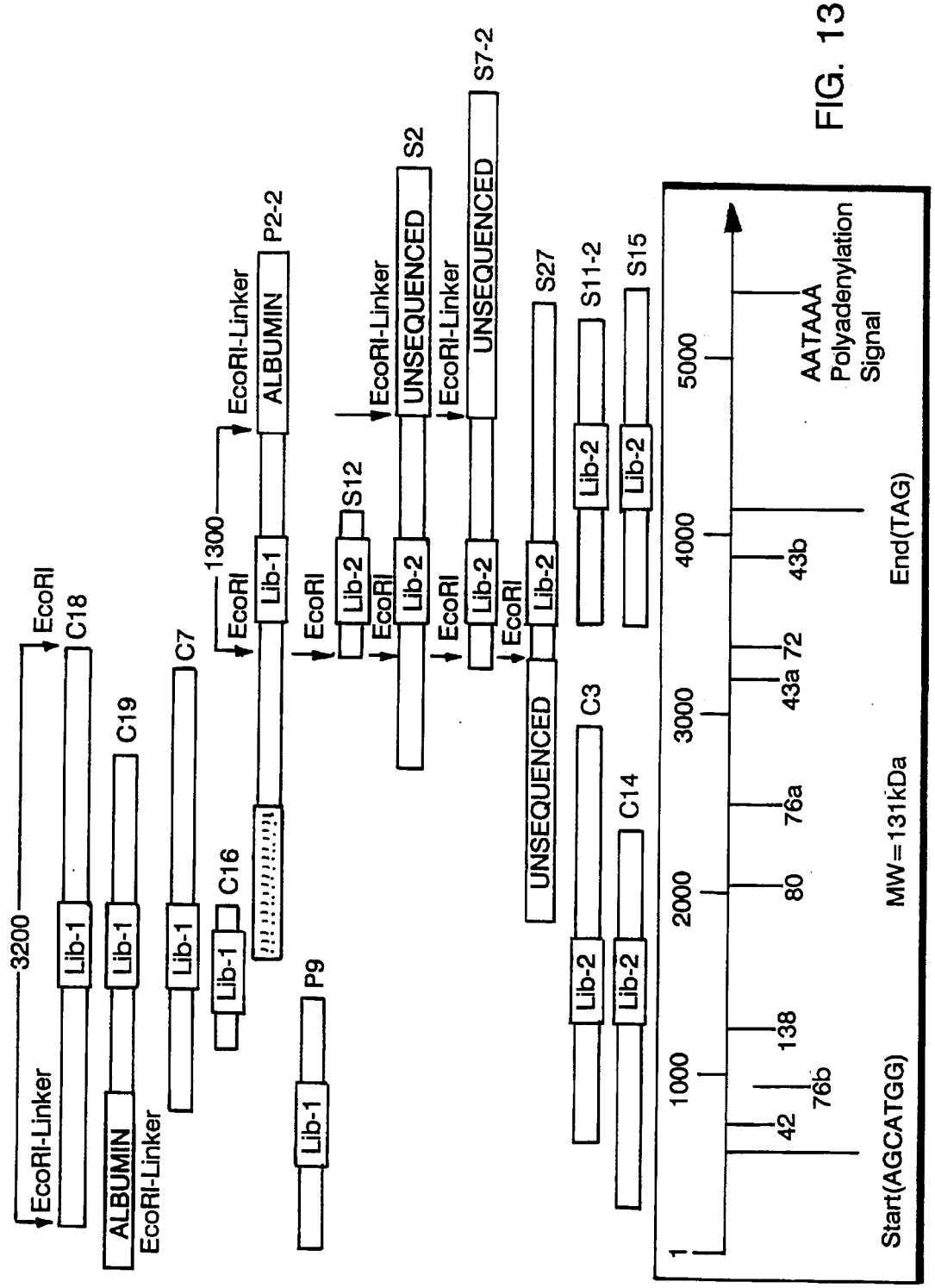
FIG. 13 is a diagram of overlapping cDNA inserts from two rat liver cDNA libraries.

The complete cDNA sequence of rat liver IRS-1 is shown in FIG. 12. It was constructed from overlapping cDNA fragments obtained from two rat liver cDNA libraries (Lib-1, Stratagene #936507 and Lib-2, Stratagene #936512, see below). Approximately $1.5 \times 10^6$ clones from Lib-1 were screened with the oligonucleotide probes (FIG. 11). Two positive recombinant phages were identified and labeled C18 and C19 (FIG. 13). (FIG. 13 is a diagram of overlapping cDNA inserts obtained from the rat liver cDNA libraries. The first two inserts obtained from Lib-1, C-18 and C-19, were identified with probe-138 (see FIG. 11). The remaining fragments were identified by two additional screenings of Lib-1 and Lib-2 using specific cDNA probes prepared with the 3200 bp ECoRI insert of C-18, or the 1300 bp EcoRI fragment from P2-2. The overlapping fragments define a contiguous piece of cDNA indicated in the black box. The cDNA is 5365 bp long and contains an open reading frame which extends from nucleotide 589 to 4293. The start and end of translation is indicated, and the relative locations of the tryptic peptides listed in Table I are shown. EcoRI sites used during the analysis are shown; only the EcoRI site at the end of the C-18 insert and in the overlapping region of the other fragments is actually found in the cDNA.)

The phages were purified, the Bluescript vector containing the cDNA insert was excised, and the inserts were characterized by EcoRI digestion and Southern blot hybridization (data not shown). C18 contained a single EcoRI insert of 3200 bp which hybridized with probe-138, but not with probe-80. The structure of C19 is shown in FIG. 13. A fragment from the C19 insert hybridized during Southern analysis with probe-138, whereas no fragment from of C19 hybridized with probe-80. Thus, probe-138 identified 2 cDNA molecules, whereas probe-80 identified none.

Nucleotide sequence analysis revealed that more than half of the C19 insert overlapped C18 (FIG. 13). However, the sequence of the 5'-end of the C19 insert corresponded to rat albumin up to the EcoRI polylinker; beyond this site, the sequence corresponded exactly to the C18 insert as indicated (FIG. 13). The C18 insert contained an open reading frame beginning with an ATG codon which matched Kozak's criteria for a translation initiation site Kozak, 1985, J. Mol. Biol. 183:1, hereby incorporated by reference; moreover, three in frame stop codons exist on the 5'-side of the ATG (FIG. 12). The amino acid sequence of both Pep-80 and Pep-138 were found in the open reading frame, even though probe-138, but not probe-80, hybridize with the cDNA. Comparison of the probe sequences with the actual cDNA sequence revealed that the "optimal" sequence of probe-80 contained 13 errors and no long stretches of identity, whereas probe-138 contained only 5 mismatches and two stretches of at least 18 matching nucleotides (FIG. 11).

Four other class I tryptic peptides attributed to a major component of the pp185 band were found in the open reading frame encoded by the C18 insert, including Pep-42, Pep-43a, Pep-76a and Pep-76b (FIG. 13). However, several peptides were not found, and no inframe stop codons were present, suggesting that only a partial cDNA clone of IRS-1 was obtained from the first screening. Lib-1 was replated and screened with the 3200 bp EcoRI fragment from C18 as the probe. Additional clones were identified (C16, C7), but these fragments overlapped entirely with the sequence of C18, and did not extend the sequence in the 3' direction (FIG. 13). A third plating and screening of Lib-1 identified two additional clones with unique inserts, $P_9$ and P2-2 (FIG. 13). The insert of P9 overlapped with that of C18, confirming the putative initiation codon. In addition, this clone extended the sequence in the 5'-untranslated region. The P2-2 insert contained two internal EcoRI sites, which yielded three fragments, see FIG. 13. Sequence analysis of the entire P2-2 insert demonstrated that it contained three regions: 1: a non-overlapping sequence at the 5'-end that did not contain an open reading frame, nor did it encode Pep-80 as predicted by the sequences of C18 and C19; 2) a region which overlapped with the 3'-end of C18 fragment and contained a 1300 bp EcoRI fragment which extended the cDNA clone of IRS-1 in the 3'-direction to an inframe stop codon, TAG; and 3) the partial sequence of rat albumin that began at a junction between EcoRI polylinkers used for the library construction, indicating that it was a likely artifact and unrelated to IRS-1 (FIG. 13).

Inframe translation of the 1300 bp EcoRI fragment from P2-2-cDNA revealed the presence of two additional tryptic peptides, Pep-72 and Pep-43b, before a stop codon (FIG. 13). The EcoRI site at the 5'-end this open reading frame was not due to polylinkers used for library construction, suggesting that it is a real site in the cDNA of IRS-1. Thus, all of the class I peptide sequences (Table I), except 2 peptides with poor quality sequence (Pep-98b and Pep-98c) were found in a contiguous cDNA molecule, suggesting that the pp185 band from rat liver contains a single insulin receptor substrate, IRS-1.

The open reading frame encoded by the unique overlapping inserts of C18, C19 and P2-2 encodes a 131 kDa protein (FIG. 13). The complete deduced amino acid sequence is shown in FIG. 12. To verify that neither some intervening sequence, nor the true start site, were missed, an additional rat liver cDNA library, Lib-2, was screened. Nine additional overlapping clones were obtained from over 2 million plaques which confirmed the original cDNA sequence (FIG. 13). In addition, these clones extended the cDNA sequence in the 3'-direction and revealed 13 inframe stop codons preceding a polyadenylation signal (AATAAA); sequencing was not extended to locate the poly-A tail. Furthermore, a consensus sequence, ATTTA, was identified three times in the 3'-untranslated region that is thought to play a role in destabilization of mRNA. This may be partially responsible for the low level of the IRS-1 in cells.

cDNA cloning was performed as follows. Two bacteriophage cDNA libraries, Stratagene #936507, or #936512, prepared with oligo dT and random primed cDNA synthesized from rat liver mRNA and inserted into the λ-Zap-II vector using EcoRI linkers were screened with optimal oligonucleotide probes. Approximately $10^6$ plaques were plated at a density of 30,000 plaques per 150 mm plate, transferred to nylon filters (New England Nuclear), and screened with an equimolar mixture of probe-80 and probe-138 ($2–6 \times 10^8$ cpm/pg). Hybridizations were performed in solutions containing 30% formamide, 10% dextran sulfate, 5×NaCl/citrate (1×NaCl/citrate is 0.15M NaCl/0.015M trisodium citrate), 2×Denhardt's solution, and 1% SDS at 42° C. The filters were washed with 0.2% SDS, 0.5×NaCl/citrate at 42° C. and exposed to Kodak XAR-5 film with a Quanta 111 intensifying screen at −60° C. The Bluescript KS⁻ plasmid containing the cDNA inserts that remained positive after plaque purification were liberated from the λ-Zap-II vector by in vivo excision as described in the manufacturer's instructions (Stratagene, Inc.). The inserts were sequenced on both strands as described previously (Williams and Birnbaum, 1989), and aligned into contiguous sequence. The sequence was confirmed by sequencing the coding strand of independent cDNA inserts which contained all the translated sequences. The sequences were aligned and analyzed using the EUGENE and SAM (Molecular Biology Computing Research Resource, Dana Farber Cancer Institute and Harvard School of Public Health).

[$^{32}$P]Phosphate, [λ-$^{32}$P]ATP (3000 Ci/mmol), [α-$^{32}$P] dCTP (3000 Ci/mmol), [α-$^{32}$P]UTP (800 Ci/mmol), and [$^{125}$I]protein A were from New England Nuclear (Boston, Mass.). Restriction enzymes and other DNA modifying enzymes were purchased from either New England Biolabs (Beverly, Mass.) or United States Biochemicals (USB, Cleveland, Ohio). Other common materials were commercial products of the highest grade available.

Identification of the mRNA for IRS-1

Northern blot hybridization analysis using poly(A)$^+$ RNA from the liver of normal and streptozotosin-induced diabetic rats revealed a faint doublet band about 9.5 kbp in length. The doublet was detected with two probes, one derived from the C18 insert and encoding the 5'-end of the cDNA, and the other derived from the 1300 bp EcoRI fragment of the P2-2 insert which encodes the 3'-end of the cDNA. Although other bands were also detected with each probe, a 9.5 kbp doublet was common to both probes suggesting that it was the major species encoding IRS-1. The smaller species may represent degradation products that are differentially recognized, as the 1.3 kbp and 2.0 kbp fragments are too small to encode IRS-1.

RNA analysis was performed as follows. Total RNA was isolated by guanidinium isothiocyanate-cesium chloride centrifugation. For Northern blot analysis, RNA was denatured with 6% formaldehyde, size-fractionated by I% agarose gel electrophoresis, and transferred to a Nytran membrane (Schleicher & Schuell) (Sambrook et al., 1989, Molecular Cloning, a Laboratory Manual, Cold Spring Harbor Press, Cold Spring Harbor, hereby incorporated by reference). The integrity and relative amounts of RNA were assessed by visualization of the ribosomal RNA by UY shadowing. Hybridizations were performed as above except that the formamide concentration was 50%, and the blots were washed in 0.2% SOS, 0.1×NaCl/citrate at 51° C. The probes used were either the full-length brain glucose transporter cDNA. (Birnbaum et al., 1986) or the 2.5 kb insert from pSMll-I. The Nytran membranes were exposed to Kodak XAR-5 lilm overnight at −80° C. with a Quanta 111 intensifying screen.

Figure 14:
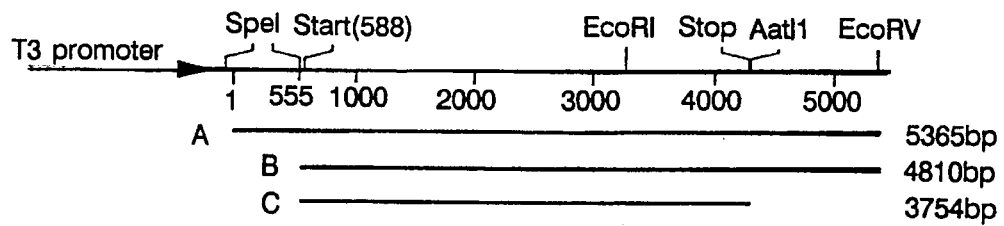
FIG. 14 is a map of three mRNA molecules.

The 131 kDa open reading frame of IRS-1 migrates as a 165 kDa protein during SDS-PAGE The molecular size of IRS-1, 131 kDA, was somewhat smaller than expected for a protein that migrates near 180 kDa during SDS-PAGE. To determine whether the cDNA for the entire protein was obtained, a full length cDNA encoding IRS-1 was constructed from several fragments, as described below, and inserted the contiguous cDNA into pBSII producing pBSII/IRS-1. The mRNA was transcribed in vitro using the t3 promoter, and the mRNA was translated in vitro in a reticulocyte lysate. Three different mRNA species were produced to test the validity of the 131 kDa open reading frame, FIG. 14. A full length mRNA molecule (5365 bp) was synthesized from the pBSII/IRS-1 plasmid that was linearized beyond the 3' end with EcoRV. A shorter mRNA (4810 bp) was transcribed from a modified plasmid linearized with EcoRV that lacked a 555 bp Spel fragment from the 5'-untranslated region. The shortest mRNA molecule which contained the open reading frame (3754 bp) was transcribed from the plasmid lacking the 555 bp Spel fragment but linearized slightly beyond the first stop codon with AatII.

In the absence of added mRNA, no [$^{35}$S]methionine-labeled proteins were detected. Translation of the 4810 bp mRNA-B produced a 162 kDa protein. In contrast, the full length mRNA, which included three inframe stop codons prior to the Kozac initiation site, produced very little of this protein product. Thus, the open reading frame most likely begins at nucleotide 589, FIG. 12. Moreover, deletion of 800 bp from the 3'-end of the cDNA had no effect on the size of the translation product, suggesting that the actual stop site occurs at nucleotide 4392. Anti-peptide antibody, αPep80, immunoprecipitated the major [$^{35}$S]methionine-labeled translation products, confirming that these protein were IRS-1.

Structural features of IRS-1

The amino acid sequence of IRS-1 shows no significant identity to known sequences in the translated Genebank. Serine is its most abundant residue (14.66%), followed by glycine (10.45%), proline (9.55%), and then alanine (7.69%). IRS-1 is largely hydrophilic containing 41.78% polar residues, and nearly twice as many based (14.41%) as acidic (8.83%) residues. It contains a few hydrophobic stretches, but none long enough to qualify as potential transmembrane spanning regions, FIG. 15A. (In FIG. 15A the hydrophathicity of the deduced sequence of IRS-1 was analyzed by the Kyte-Doolittle algorigm.) This result is consistent with the presumed cytoplasmic location of the pp185 band, Daniel et al, 1987, J. Biol. Chem. 262:9778, hereby incorporated by reference. IRS-1 contains 5 consensus sequences for asparagine-linked glycosylation (Asn-Xxx-Ser/Thr), although there is no evidence that IRS-1 is glycosylated.

The consensus sequence for a nucleotide binding site, Gly-X-Gly-X-X-Gly (SEQ ID No: 25), is found 8 times in IRS-1 (FIG. 15B). This conserved sequence is proposed to join a β-sheet with an α-helix, forming an elbow around the nucleotide with the first glycine in contact with the ribose moiety and the second lying near the pyrophosphate, Wierenga et al., 1983, Nature 302:842 hereby incorporated by reference. This motif occurs once in IRS-1 beginning at $Gly_{137}$ and ending at $Lys_{156}$, which is located 14 amino acids beyond $Gly_{142}$, FIG. 15B. $Lys_{156}$ exists in the motif, Ala-X-LYs-$_{156}$-X-Val, which is frequently found in protein kinases.

IRS-1 contains many potential phosphorylation sites, FIG. 15C. Based on typical motifs for cAMP-dependent protein kinase ([R,K]-[R,K]-X-[S,T], protein kinase C ([S,T]-X-[R,K]) and casein kinase ([S,T]-X-X-[E,D]), 33 putative Ser/Thr phosphorylation sites are distributed throughout the protein. In addition, at least 10 potential tyrosine phosphorylation sites can be identified, FIG. 15C. These sites were located by the presence of negatively charged amino acids adjacent to tyrosine residues, Kemp, et al., 1990, TIBS 15:342, hereby incorporated by reference. Moreover, six of these putative tyrosine phosphorylation sites are located in the central region of the protein and contain the motif, YMXM (SEQ ID NO:1), and one site has the sequence EYYE (SEQ ID NO:26), FIG. 16.

To test the validity of the YMXM (SEQ ID NO:1) motif as a phosphorylation site for the insulin receptor, synthetic peptides were prepared containing the sequence of $Tyr_{46}$ (KK-$Y_{46}$-1), $Tyr_{608}$ (KK-$Y_{608}$-1) and $Tyr_{727}$ (KK-$Y_{658}$1). The phosphorylation of these peptides by the partially purified insulin receptor was compared to the phosphorylation of these peptides by the partially purified insulin receptor was compared to the phosphorylation of peptide IR1150, which includes the amino acid sequence around the major autophosphorylation sites of the insulin receptor, $Y_{1146}$, $Y_{1150}$ and $Y_{1151}$, FIG. 17). The KK-$Y_{46}$-1 peptide (open circles) was a very poor substrate for the insulin receptor compared to the control IR1150 peptide. In contrast, the YMXM-containing peptides, KK-$Y_{608}$-1 (solid rectangles) and KK-$Y_{658}$-1, were at least as good as the IR1150 peptide. In each case, the YMXM peptides displayed $V_{max}$ values twice as high as the IR1150 peptide, but they had slightly higher $K_m$ values. Although the phosphorylation sites actually used by the insulin receptor in the intact cell have not yet been identified, these results suggest that IRS-1 contains several candidate sites with the interesting YMXM motif.

In vitro kinase assays were performed as follows. The synthetic peptide substrate ($IR_{1150}$), composed of amino acids 1143–1152 of the human insulin receptor (numbered as per Ullrich et al., 1984, Nature 309:418, hereby incorporated by reference, was purchased from Dr. David Coy, Tulane University, New Orleans, La. Lectin-purified insulin receptors, normalized to insulin binding activity, were incubated for various periods of time in a final volume of 50 μl containing 50 mM HEPES pH 7.5, 0.1% Triton X-100, 5 mM $MnCl_2$, and the absence or presence of 100 nM insulin. Substrate phosphorylation was initiated by the addition of varying concentrations of peptide for 5 min at 22° C. Reactions were terminated by the sequential addition of 20 μl 1% bovine serum albumin (BSA) and 50 μl 10% trichloroacetic acid (TCA). Precipitated protein was removed by centrifugation, and the supernatant, containing the phosphorylated peptide, was applied to a 1×1 inch piece of phosphocellulose paper (Whatman). The papers were washed with 4 changes (1 liter each) of 75 mM phosphoric acid, and the retained radioactivity was measured by Cerenkov counting.

Phosphorylation of IRS-1 by the wild-type and mutant insulin receptor in CHO cells CHO cells expressing the wild-type human insulin receptor were labeled with [$^{32}$P]orthophosphate for 2 h, and then stimulated with 100 nM insulin for 1 min. This time interval was chosen because in previous experiments, the pp185 band showed maximal phosphorylation after 20 s of insulin stimulation. In the absence of insulin, the anti-phosphotyrosine antibody (αPY) immunoprecipitated several proteins which were also detected after insulin stimulation. However, insulin stimulated the tyrosine phosphorylation of 2 additional protein bands, the β-subunit of the insulin receptor (95 kDa) and pp185. The pp185 band from CHO cells was previously shown to migrate at 175 kDa during SDS-PAGE, Bjorge et al., 1990, Proc. Natl. Acad. Sci. (USA) 87, 3816–3820, hereby incorporated by reference.

Phosphoproteins from an equal portion of control and insulin-stimulated cell extract were immunoprecipitated with an antibody against Pep-80 (αPep80). In the absence of insulin, the major phosphoprotein migrated at 165 kDa. Other minor proteins were also detected at 120 kDa, 100 kDa, and 55 kDa. Interestingly, these protein were also detected in the αPY immunoprecipitate and may constitute non-specific binding; however, the 165 kDa protein, IRS-1, was the major phosphoprotein present in the αPep80 immunoprecipitate. After insulin stimulation, the phosphorylation of IRS-1 protein increased about 2-fold and it migrated at a slightly higher molecular weight (170 kDa), consistent with insulin-stimulated phosphorylation occurring within 1 min. However, IRS-1 clearly migrated below the center of the pp185 band immunoprecipitated with the αPY.

As pp185 is a phosphotyrosine-containing protein, qualitative phosphoamino acid analysis was carried out. Before insulin stimulation, IRS-1 immunoprecipitated with the αPep80 contained predominantly Ser(P) with a small amount of Thr(P), but no Tyr(P) was detectable; however, insulin stimulated the appearance of Tyr(P) in IRS-1. The corresponding analysis of the pp185 band immunoprecipitated with αPY revealed Ser(P), Thr(P) and a small amount of Tyr(P) in the basal state, and a larger increase in Try(P) after insulin stimulation. The difference in the amount of Tyr(P) in the IRS-1 and the pp185 band after insulin stimulation is unknown.

It has previously been demonstrated that mutation of the insulin receptor in the juxtamembrane region of the β-subunit blocked the ability of insulin to stimulate tyrosine phosphorylation of pp185, whereas autophosphorylation of the mutant receptor was normal, White et al., 1988, Cell 54:641, hereby incorporated by reference. CHO cells expressing the wild-type human insulin receptor (CHO/$HIR_c$), and mutant receptors containing point mutations (CHO/$IR_{F960}$) or a partial deletion ($IR_{\Delta960}$) of the juxtamembrane region were labeled with [$^{32}$P]orthophosphate. Insulin stimulated the tyrosine phosphorylation of the β-subunit of each receptor as shown by immunoprecipitation with the αPY. In contrast, the pp185 band was strongly phosphorylated only by the wild-type insulin receptor, whereas the $IR_{F960}$ and $IR_{\Delta960}$ showed no phosphorylation of the pp185 band. Similarly, immunoprecipitation of an equal amount of these cell extracts with αPep80 showed insulin-stimulated phosphorylation of the IRS-1 in the CHO/HIRc cells; insulin had no effect on the phosphorylation of IRS-1 in the CHO/$IR_{F960}$ and CHO/$IR_{\Delta960}$. Thus the mutant receptors were not stimulating the phosphorylation or molecular weight shift of IRS-1 suggesting that IRS-1 interacts with the wild-type and mutant insulin receptor in a similar fashion to the components of the pp185 band. Based on these results, we conclude that IRS-1 is a substrate of the insulin receptor and is a component of the pp185 band.

In vivo phosphorylation and phosphoamino acid analysis were performed as follows. CHO cells were grown in 10 cm dishes in F12 medium containing 10% fetal bovine serum (Gibco). Subconfluent CHO cells ($10^6$) were transfected by calcium phosphate precipitation with 1 μg pSVEneo alone or together with 10 μg of pCVSVHIRc, pCVSVHIRc/F960, or pCVSVHIRc/Δ960 as previously described (10–11). After 72 h, 800 μg/ml of geneticin (GIBCO) was added to the medium to select for neomycin-resistant cells. Surviving cells were cultured in the presence of geneticin to amplify the cell line. CHO cells that expressed high levels of surface insulin receptors were selected by fluorescence-activated cell sorting (13), and clonal cell lines were obtained by plating at limiting dilution.

Insulin receptor mutants were constructed, using oligonucleotide-directed mutagenesis, in which Tyr960 was substituted with phenylalanine ($IR_{F960}$) or 12 amino acids (A954-D965) were deleted from the juxtamembrane region ($IR_{\Delta960}$). CHO/neo cells, expressing only pSVEneo, contained about 3,000 hamster insulin receptors. Following transfection and selection by fluorescence-activated cell sorting, clonal lines of CHO/IR cells and mutant CHO/$IR_{F960}$, and CHO/$IR_{\Delta960}$ cells were obtained which expressed approximately 80,000 receptors/cell. Scatchard analysis of CHO/$IR_{F960}$ and CHO/$IR_{\Delta960}$ cells has been previously described, and indicated that binding was normal (10–11). The insulin dose response of in vitro autophosphorylation by partially purified receptors from CHO/IR, CHO/$_{F960}$ and CHO/$_{\Delta960}$ cells was identical; a half-maximal response was obtained at approximately 3 nM insulin for all three lines, identical to the insulin binding affinity of the receptors. Thus, despite mutations near the transmembrane domain, the coupling of insulin binding to receptor autophosphorylation was normal in the $IR_{F960}$ and $IR_{\Delta960}$.

Confluent monolayers of transfected CHO cells in 10 or 15 cm dishes (Nunc) at 37° C. were labeled for 2 h with 0.5 mCi/ml with [$^{-32}$P]phosphate (New England Nuclear) as previously described (Backer et al., 1990). The cells were incubated for additional periods of time in the presence of 100 nM insulin, rapidly frozen with liquid nitrogen, and solubilized in 100 mM Tris, pH 8.2, containing 2 mM sodium vanadate, 3.4 mg/ml PMSF, 100 µg/ml aprotinin, 1 µg/ml leupeptin, and 1% Triton-X-100. Tyr(P)-containing proteins were immunoprecipitated with anti-phosphotyrosine antibody (αPY); precipitated proteins were reduced with dithiothreitol and analyzed by SDS-PAGE. Immunoprecipitated proteins were identified by autoradiography and the radioactivity in the insulin receptor subunits was quantified by liquid scintillation counting.

Immunoprecipitates of IRS-1 contain phosphatidyl inositol 3-kinase activity

The phosphatidyl inositol 3-kinase (PtdIns 3-kinase) is activated by several growth factor receptor tyrosine kinases and is thought to be involved in the regulation of DNA synthesis, Kaplan et al., 1987, Cell 50:1021, hereby incorporated by reference. Several reports suggest that it is a 85 kDa protein which undergoes tyrosine phosphorylation or associates tightly with phosphotyrosine-containing proteins, Kaplan et al., 1987, supra. However, it is not clear whether direct tyrosine phosphorylation of the PtdIns 3-kinase or its association with Tyr(P)-containing proteins is required for its activation.

Insulin stimulated the PtdIns 3-kinase was detected in αPY immunoprecipitates and in anti-insulin receptor immunoprecipitates as, Ruderman et al., 1990, Proc. Natl. Acad. Sci. (USA), 87:1411, hereby incorporated by reference, and Endemann et al., 1990, J. Biol. Chem 265:396, hereby incorporated by reference. Extracts from basal or insulin-stimulated CHO/HIRc cells were incubated with αPY, two preparations of anti-insulin receptor antibody (B2 or K-14), and αPep80. The PtdIns 3-kinase activity was measured in each immunoprecipitate. FIG. 18 shows the insulin stimulation of phosphatidyl inositol 3-kinase. CHO/IR cells were stimulated with insulin (100 nM) for 10 min and extracts were prepared. The PtdIns 3-kinase activity was assay in immuncomplexes prepared with αPY (Tyr(P)), two anti-insulin receptor antibodies (B2 and K-14) and αPep80.

Phosphatidyl inositol 3-kinase activity was assayed as follows. In vitro phosphorylation of phosphatidylinositol was measured as previously described (Ruderman et al., 1990, supra). Subconfluent CHO cells grown in 100 mm dishes were made quiescent by an overnight incubation in F-12 medium containing 0.5% BSA. The cells were then incubated in the absence or presence of insulin (100 nM) for 10 min, and washed once with ice cold PBS and twice with 20 mM Tris (pH 7.5) containing 137 mM NaCl, 1 mM $MgCl_2$, 1 mM $CaCl_2$, and 100 µM $Na_3VO_4$ (Buffer A). The cells were solubilized in 1 ml Buffer A containing 1% NP-40 (Sigma) and 10% glycerol, and insoluble material was removed by centrifugation at 13,000×g for 10 min. Tyrosyl phosphoproteins were immunoprecipitated from the supernatant with αPY and protein A-sepharose (Pharmacia). Alternatively, anti-insulin receptor or control antibodies were used as described in the text. The immunoprecipitates were washed successively in PBS containing 1% NP-40 and 100 µM $Na_3VO_4$ (3 times), and 10 mM Tris (pH 7.5) containing 100 mM NaCl, 1 mM EDTA and 100 µM $Na_3VO_4$ (2 times). The pellets were resuspended in 50 µl of 10 mM Tris (pH 7.5) containing 100 mM NaCl and 1 mM EDTA. To each pellet was added 10 µl 100 mM $MnCl_2$ and 10 µl of phosphatidylinositol (2 µg/µl) sonicated in 10 mM Tris (pH 7.5)/1 mM EGTA. The reaction was started by the addition of 10 µl of 440 µM ATP containing 30° Ci [$^{32}$P]ATP. After 10 min at 22° C., the reaction was stopped by the addition of 20 µl 8N HCl and 160 βl $CHCl_3$: methanol (1:1). The samples were centrifuged, and the lower organic phase was removed and applied to a silica gel TLC plate (Merck) which had been coated with 1% potassium oxalate. TLC plates were developed in $CHCl_3$:$CH_3OH$:$H_2O$: $NH_4OH$ (60:47:11.3:2), dried and visualized by autoradiography. The radioactivity in spots which co-migrated with PtdIns-4P standard (Sigma) was measured by Cerenkov counting as previously described (Ruderman et al., 1990).

Structure and Function of IRS-1

Insulin stimulates tyrosine phosphorylation of IRS-1 in CHO cells expressing wild-type human insulin receptor. This leads to a slight retardation of its migration during SDS-PAGE, which is a typical finding following protein phosphorylation. Moreover, most of the immunoprecipitated IRS-1 migrates more slowly after 1 min of insulin stimulation, suggesting the cellular IRS-1 reacts quickly and completely with the insulin receptor. Thus IRS-1 is expected to be a physiologically relevant substrate of the insulin receptor. Phosphoamino acid analysis reveals that both IRS-1 and the pp185 band contain Ser(P) and a small amount of Thr(P) before and after insulin stimulation. In addition, the pp185 band contains a small amount of Tyr(P) before insulin stimulation. The amount of Tyr(P) in IRS-1 is detectable only after insulin stimulation, and is relatively low compared to the Tyr(P) in the pp185 band following insulin stimulation. This disparity is consistent with the presence of additional Tyr(P)-containing proteins in the pp185 band, or the inability of αPep80 to recognize the highly tyrosine phosphorylated form of the IRS-1. Expression of the IRS-1 cDNA in CHO cells and the preparation of other antibodies will be necessary to resolve this question.

Several structural feature of the insulin receptor are required for tyrosine phosphorylation of the pp185 band in CHO cells including a functional ATP binding site, an intact regulatory region which contains the major autophosphorylation sites, and a normal juxtamembrane region. Point mutations or a deletion of a portion of the juxtamembrane region inhibits insulin signal transmission and phosphorylation of the pp185 band, without altering autophosphorylation of the insulin receptor. Two insulin receptor molecules containing juxtamembrane mutations, $IR_{F960}$ and $IR_{A960}$, did not phosphorylate IRS-1 during insulin stimulation of transfected CHO cells. Thus, IRS-1 shows a similar dependance on an intact juxtamembrane region of the insulin receptor for insulin-stimulated phosphorylation. These results demonstrate that IRS-1 has the expected characteristics of a pp185 component.

IRS-1 mRNA is in very low abundance. The 0.5 kbs doublet detected during Northern analysis is difficult to observe and required several day exposure with a probe of high specific activity. Based on parallel blots with rat liver insulin receptor probes, it is estimated that IRS-1 is about 5% as abundant as the insulin receptor. IRS-1 mRNA may be unstable, because the 3'-untranslated region containing the sequence motif ATTTA which has been implicated as a destablizing motif in other mRNA molecules. Northern analysis of mRNA from rat liver, muscle, spleen, brain and kidney indicates that IRS-1 is found in all of these cell types, suggesting that it may play an essential role of insulin signaling in all tissues. This is consistent with results with αPY in previous studies which indicate the pp185 band is found in all cell types evaluated, Rosen, 1987, Science 237:1452, hereby incorporated by reference. Partial sequence analysis of IRS-1 from a human muscle cDNA library indicates the IRS-1 is extremely well conserved between rat liver and human skeletal muscle. These results support the hypothesis that IRS-1 plays an essential and conserved role in cellular regulation by insulin.

The deduced amino acid sequence of IRS-1 is unique, which hampers attempts to deduce its function by comparison with homologous proteins. IRS-1 is a hydrophilic protein with no stretch of hydrophobic residues long enough to provide a transmembrane spanning region. It contains an abundance of glycine and proline residues which leads frequently to the motif Gly-Pro-Y, which leads to a weak alignment between IRS-1 and collagen; however, the proteins are clearly distinct. Several structural motifs are found in IRS-1 which may provides clues regarding its role in insulin action including, 8 nucleotide binding motifs, a kinase-like ATP-binding site, tyrosine phosphorylation sites with the motif YMXM, multiple serine and threonine phosphorylation sites, and a run of 10 glutamine residues.

Insulin action is thought to be mediated through a cascade of protein phosphorylation and dephosphorylation. Whether IRS-1 plays a direct role in this mechanism as a protein kinase is unknown. Our previous attempts to label the components of the pp185 band with ATP affinity reagents have been unsuccessful. However, one of the eight nucleotide binding motifs in IRS-1 has the clear appearance of a ATP binding site. The nucleotide binding component has the structure $Gly_{137}$-Val-Gly-Glu-Ala-Gly (SEQ ID NO:27) and 14 amino acids away is the essential catalytic $lys_{156}$. In addition, the lysine reside is in an Ala-Xxx-Lys-Ile- (SEQ ID NO:28) motif, which is conserved among many protein kinases, Hanks et al., 1990, Science 241:42, hereby incorporated by reference. None of the other nucleotide binding motifs show this additional homology. Hanks et al. recently described 11 conserved subdomains commonly found in protein kinase catalytic domains. The ATP binding site is located in region I, and all protein kinases evaluated contain a glutamic acid residue in region II, 13 to 42 residues down-stream from the catalytic lysine residue of region I. Consistent with this model, IRS-1 contains $Clu_{194}$ 38 residues away from $Lys_{156}$. Region III of kinase catalytic domains contains a conserved leucine or isoleucine 10 to 17 residues away from the conserved glutamic acid of region II; IRS-1 has $Ile_{206}$, 11 residues beyond $Glu_{194}$. However, IRS-1 lacks the Asp-Phe-Gly motif of region VII, and the Ala-Pro-Glu motif of region VIII, which are absolutely predictive of a protein kinase. The Ala-Pro-Glu motif is essential for catalytic activity in $pp60^{c-src}$ and is located about 20 residues down-stream from the autophosphorylation sites in protein kinases. The absence of these motifs from IRS-1 rules out the possibility that the IRS-1 is a typical protein kinase.

Tyrosine phosphorylation links IRS-1 to this insulin receptor. At least 10 potential tyrosine phosphorylation sites were detected by eye in the deduced sequence, as any Tyr residue with an Asp or Glu residue nearby was considered a possibility. Interestingly six of these Tyr residues resided in a YMXM motif, which is also found in the polyoma middle T antigen (MTag), Carmichael et al., 1980, J. Biol. Chem, 255:230, hereby incorporated by reference, and receptor tyrosine kinases for PDGF, Yarden et al., 1986, Nature 323,226–232, hereby incorporated by reference, CSF-1, Sherr et al., 1985, Cell, 41, 665–676, hereby incorporated by reference, and EGF, Yarden et al., 1986, Nature, 323, 226–232, hereby incorporated by reference; Ullrich et al., 1984, Nature, 309, 418–425, hereby incorporated by reference. IRS-1 synthetic peptides containing the YMXM motif are good substrates for the insulin receptor as their $K_m$ values are nearly the same as insulin receptor peptide4. Although we have no information about in vivo sites, all of the YMXM motifs look like good possibilities. In contrast, the motif Glu-Tyr-Tyr-Glu, is not phosphorylated well by the insulin receptor, suggesting that the presence of a Tyr in the YMXM motif with adjacent negatively charged amino acids may define the preferred substrate of the insulin receptor tyrosine kinase.

Recently, tyrosine phosphorylation sites in MTag and various growth factor receptors, in particular the PDGF and EGF receptors, have been shown to bind specifically to the src homology-2 (SH2) domain in certain signal transduction proteins, including phosphoinositide-specific phospholipase C (PLC 1), GTPase activating protein (GAP), phosphatidyl inositol 3-kinase (PtdIns 3'-kinase) and $p74^{raf}$, Anderson et al., 1990, Nature, 250,979–982, hereby incorporated by reference. The SH2 domain was first identified in nonreceptor protein tyrosine kinases like Src and Fps, by its apparent ability to interact with the kinase domain and phosphorylated substratesy. Several motifs are highly conserved within the SH2 domain which typically begins with the sequence W-(Y/F)-(H/F)-G-K. Bacterially expressed SH2 domains from PLC 1 or GAP immobilized on Sepharose precipitate the PDGF and EGF receptor, suggesting that ligand-stimulated tyrosine phosphorylation may regulate the interaction between the receptor and cellular protein. Thus, tyrosine phosphorylation enable certain proteins to bind to cellular protein containing SH2 domains and potentially altering their activity.

Although the insulin receptor contains Tyr(P), it has not been shown to bind PLC 1, GAP, and $p74^{raf}$. Although insulin activates PtdIns 3'-kinase which is found in αPY immunoprecipitates, the IR weakly binds PtdIns 3'-kinase {}. This suggests that all Tyr(P) residues are not in the proper configuration to interact with SH2 domains; moreover, the insulin receptor does not contain any tyrosine phosphorylation sites in the YMXM motif, which appears to be strongly recognized by SH2 domains. Thus, IRS-1, which contains 6 tyrosine phosphorylation sites in YMXM motifs may serve as a link between the insulin receptor and cellular proteins involved in the regulation of growth and metabolism. This conclusion is supported by the strong immunoprecipitations of PtdIns 3'-kinase from insulin stimulation cells with our relatively weak IRS-1 antibodies. Thus, IRS-1 may serve as a cytoplasmic ligand that links the insulin receptor to SH2 domain-containing enzymes involved in cellular regulation.

The regulation of IRS-1 phosphorylation is potentially very complex. IRS-1 contains many potential serine and threonine phosphorylation sites, and it is serine phosphorylated in the basal state. The pp185 band in Fao hepatoma cells undergoes serine/threonine phosphorylation during stimulation with TPA, which inhibits partially the stimulation of DNA and glycogen synthesis by insulin. Moreover, IRS-1 contains 8 putative nucleotide binding sites which could provide additional regulation through other mechanisms. Thus IRS-1 provides a common intermediate through which multiple protein kinases and other signal transduction systems may communicate.

IRS-1 contains a run of 10 glutamine residues beginning at $Gln_{871}$. Glutamine-rich regions have been found in amino acid sequences of several eukaryotic regulatory proteins including the androgen receptor Lubahn et. al., 1988, Mol. Endocrin. 2:1265, hereby incorporated by reference, mineralocorticoid receptor Arriza et. al., 1987, Science 237:268, hereby incorporated by reference, glucocorticoid receptor Hollenberg et. al., 1991, Nature 318:635, hereby incorporated by reference, human c-myc oncogene Rabbitts et. al., 1983, Nature 306:760, hereby incorporated by reference, the transcription factor $SP_1$ Courey et. al., 1988, Cell 55:887, hereby incorporated by reference, Drosophila zeste gene which binds and activates the Ubx promoter Pirrotta et. al., 1987, EMBO J. 6:791, hereby incorporated by reference, and products of the homoeobox containing genes such as Antp and Cut. The sequence similarity is limited at most to the run of glutamines and a few adjacent amino acids. However, the role and specificity of the glutamine residues is unclear Courey et. al., 1988, Cell 55:887, hereby incorporated by reference. IRS-1 lacks other characteristics suggestive of a DNA binding protein.

In summary, IRS-1 may provide a molecular link between the insulin receptor and cellular enzymes involved in regulation of cellular growth and metabolism. The amino acid deduced sequence of IRS-1 does not contain any obvious enzymatic function; however, its low abundance, general distribution, and the presence of several common motifs in the sequence suggest that it may play an important role in insulin action. Provisionally, we propose that IRS-1 acts a molecular link between the insulin receptor and cellular proteins which contain the SH2 domain. Other tyrosine kinases may also phosphorylated IRS-1, and other signaling systems such as serine/threonine kinases and nucleotides may regulate the signal flux.

Human IRS-1

Human IRS-1 encoding DNA can be obtained by the methods of the invention or, preferably, by homology to DNA encoding rat IRS-1, by methods known to those skilled in the art, e.g., by probing a human genomic or cDNA library, preferably a liver cDNA library, with nucleic acid encoding rat IRS-1.

Human IRS-1 can be obtained by the protein purification methods described herein, or more preferably, by expression from recombinant human DNA encoding IRS-1, by methods known to those skilled in the art.

Use

Dosages of tyrosine kinase inhibiting substances and other therapeutic substance will vary, depending on factors such as, the disease being treated, the half life of the substance, potency, route of administration, and the condition of the patent.

Other Embodiments

Other embodiments are within the following claims, e.g., the molecules and methods of the invention can be used to diagnose insulin related diseases, e.g., diseases characterized by insulin resistance, e.g., Type II diabetes. These diagnostic tests can be based on the use of antibodies to IRS-1 to determine the levels of IRS-1 in a tissue sample taken from a patient. Alternatively they can measure some other significant aspect of IRS-1 metabolism expression or action, e.g., the extent of IRS-1 phosphorylation, or the cellular or intracellular distribution of IRS-1. Cloned DNA homologous to DNA that encodes IRS-1 can also be used to measure levels of IRS-1 expression, e.g., by measuring levels of IRS-1 encoding mRNA. Levels of any of these parameters that deviate significantly from normal are diagnostic of disease. Normal and disease state levels of IRS-1, IRS-1 RNA, IRS-1 phosphorylation, or other significant parameters of IRS-1 metabolism expression, or action, can be determined by methods known to those skilled in the art.

Insulin related-disease states, e.g., insulin-resistant diseases, e.g., Type II diabetes, that are caused by a structural defect in the insulin receptor substrate gene can be diagnosed by using DNA homologous to the IRS-1 gene to discover the structural defect. Structural defects in a gene can be discovered by methods known to those skilled in the art, e.g., by restriction fragment length polymorphism or DNA sequence analysis.

What is claimed is:

1. A purified preparation of IRS-1, of sufficient purity to allow protein sequencing, said IRS-1 having the following properties:
   (a) a molecular weight, as determined by SDS-PAGE, of about 165 kDa;
   (b) phosphatidylinositol (PI) 3-kinase activity;
   (c) it is phosphorylated in response to insulin binding to the insulin receptor;
   (d) it is a substrate for the insulin receptor.

2. The purified preparation of claim 1, said IRS-1 further having the following additional properties:
   (a) it has a Gly-X-Gly-X-X-Gly motif;
   (b) it has a kinase-like ATP binding site;
   (c) it has a YMXM phosphorylation motif; and
   (d) it has an Asn-Xxx-Ser/Thr site for asparagine-linked glycosylation.

3. The purified preparation of claim 1, wherein said protein can be found in the cytoplasm.

4. The purified preparation of claim 1, wherein said protein is expressed from a purified nucleic acid.

* * * * *

UNITED STATES PATENT AND TRADEMARK OFFICE
CERTIFICATE OF CORRECTION

PATENT NO. : 5,621,075 Page 1 of 1
DATED : April 15, 1997
INVENTOR(S) : Kahn et al.

It is certified that error appears in the above-identified patent and that said Letters Patent is hereby corrected as shown below:

Column 1,
Line 7, before BACKGROUND OF INVENTION, insert the following paragraph:

-- STATEMENT REGARDING FEDERALLY SPONSORED RESEARCH
This invention was made with support from the U.S. government under grant number DK33201 awarded by the National Institutes of Health. The government has certain rights in the invention. --.

Signed and Sealed this

Eighteenth Day of February, 2003

JAMES E. ROGAN
*Director of the United States Patent and Trademark Office*